(12) United States Patent
Merchiers et al.

(10) Patent No.: US 7,429,459 B2
(45) Date of Patent: Sep. 30, 2008

(54) METHODS FOR IDENTIFYING A COMPOUND THAT INHIBITS THE PROCESSION OF AMYLOID-BETA PROTEIN PRODUCTION IN A MAMMALIAN CELL EXPRESSING APP AND OVEREXPRESSING A G-PROTEIN COUPLED RECEPTOR IN THE CELL

(75) Inventors: Pascal Gerard Merchiers, Tielen (BE); Marcel Hoffmann, Uithoorn (NL); Koenraad Frederik Florentina Spittaels, Puurs (BE)

(73) Assignee: Galapagos N.V., Mechelen (BE)

( * ) Notice: Subject to any disclaimer, the term of this patent is extended or adjusted under 35 U.S.C. 154(b) by 0 days.

(21) Appl. No.: 11/110,274

(22) Filed: Apr. 20, 2005

(65) Prior Publication Data

US 2005/0266502 A1   Dec. 1, 2005

Related U.S. Application Data

(60) Provisional application No. 60/563,661, filed on Apr. 20, 2004.

(51) Int. Cl.
*G01N 33/53*   (2006.01)
*G01N 33/542*   (2006.01)
*G01N 33/566*   (2006.01)
*C12P 21/06*   (2006.01)
*C12P 21/04*   (2006.01)

(52) U.S. Cl. ............... 435/7.1; 435/69.1; 435/7.21; 435/7.9; 435/70.3

(58) Field of Classification Search ............... None
See application file for complete search history.

(56) References Cited

U.S. PATENT DOCUMENTS

| 5,998,164 A | 12/1999 | Li et al. |
| 6,090,575 A | 7/2000 | Li et al. |
| 6,653,086 B1 | 11/2003 | Behan et al. |
| 7,163,800 B2 | 1/2007 | Oakley et al. |
| 2002/0082412 A1 | 6/2002 | Brennand et al. |
| 2003/0044898 A1 | 3/2003 | Li et al. |
| 2003/0113798 A1 | 6/2003 | Burmer et al. |
| 2004/0093626 A1 | 5/2004 | Brennand et al. |
| 2005/0118639 A1 * | 6/2005 | Hinuma et al. ............... 435/7.1 |

FOREIGN PATENT DOCUMENTS

| WO | WO0190128 | * | 11/2001 |
| WO | 02/068579 A2 | | 9/2002 |
| WO | WO03097795 | * | 11/2003 |
| WO | 2004/042405 A2 | | 5/2004 |

OTHER PUBLICATIONS

Kostenis et al. Trends in Pharmacological Science 2005. 26: 595-602.*
Fortini Nat. Rev. Cell Biol.2002.3: 673-684.*

* cited by examiner

*Primary Examiner*—Christine J Saoud
*Assistant Examiner*—Chang-Yu Wang
(74) *Attorney, Agent, or Firm*—Synnestvedt & Lechner LLP

(57) ABSTRACT

A method for identifying compounds that inhibit amyloidal-beta precursor protein processing in cells, comprising contacting a test compound with a GPCR polypeptide, or fragment thereof, and measuring a compound-GPCR property related to the production of amyloidal-beta peptide. Cellular assays of the method measure indicators including second messenger and/or amyloid beta peptide levels. Therapeutic methods, and pharmaceutical compositions including effective amyloidal-beta precursor processing-inhibiting amounts of GPCR expression inhibitors, are useful for treating conditions involving cognitive impairment such as Alzheimers Disease.

11 Claims, 7 Drawing Sheets

Fig 3:
A
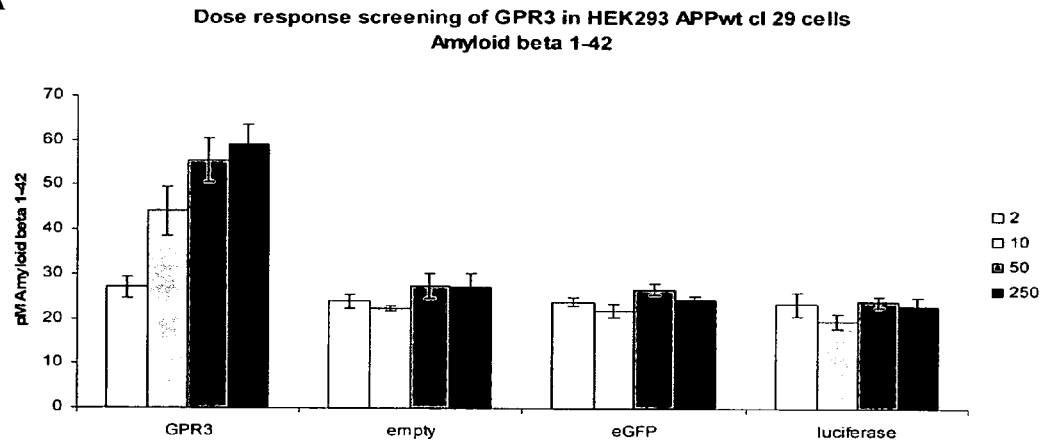
B
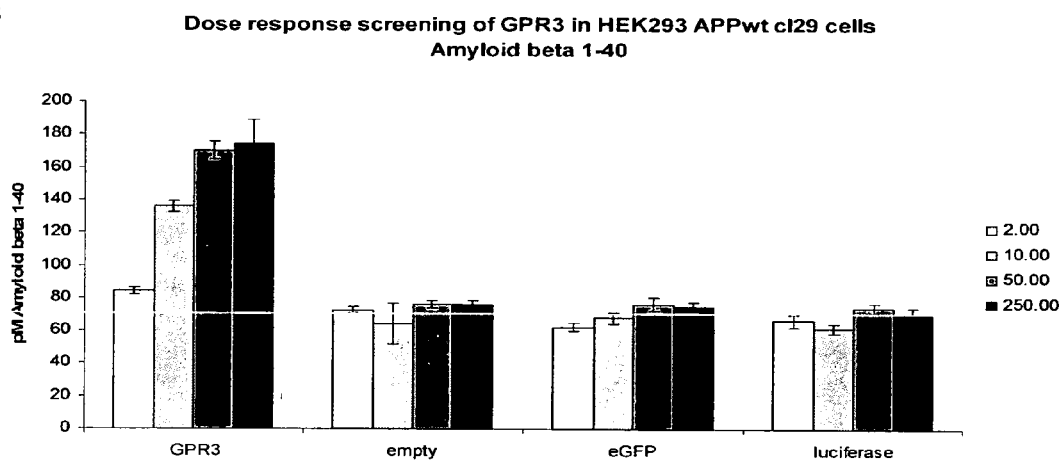
C
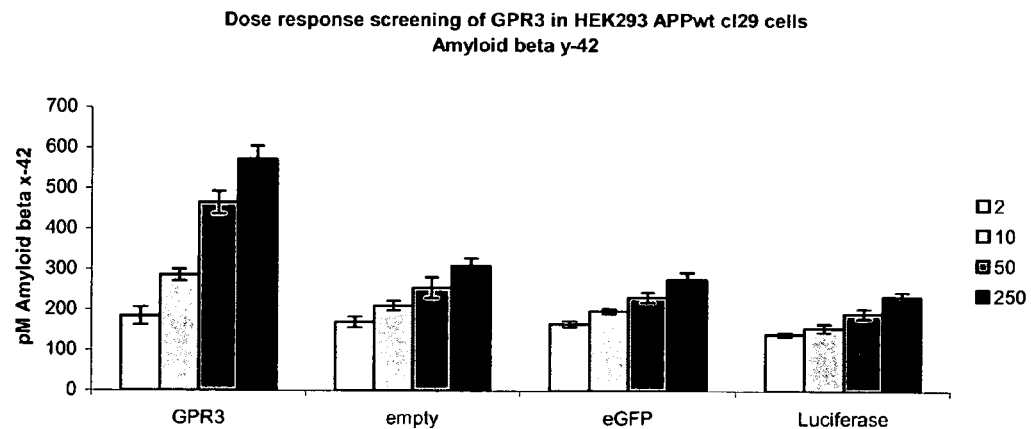

Fig 3(cont.):
D
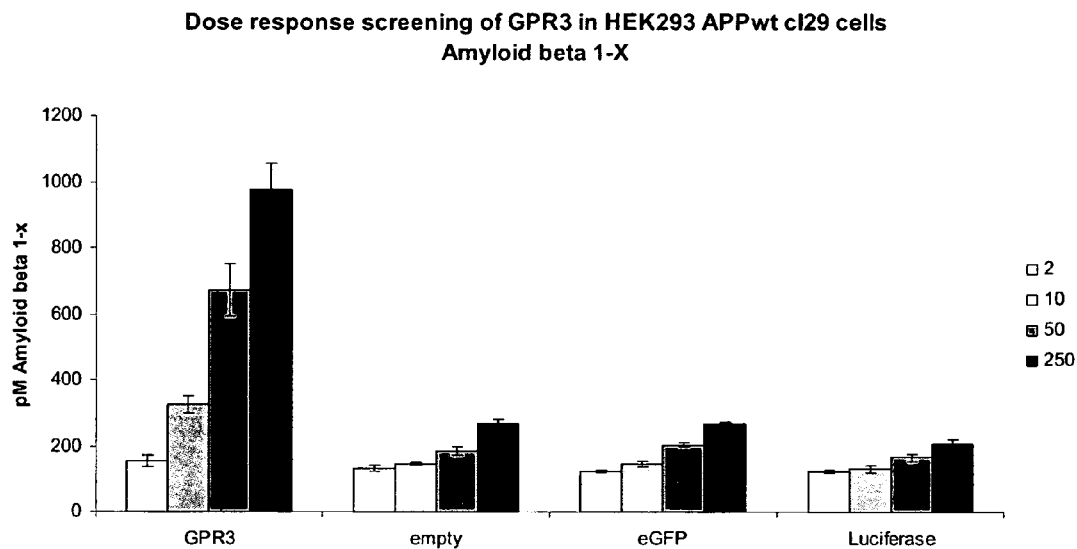
E
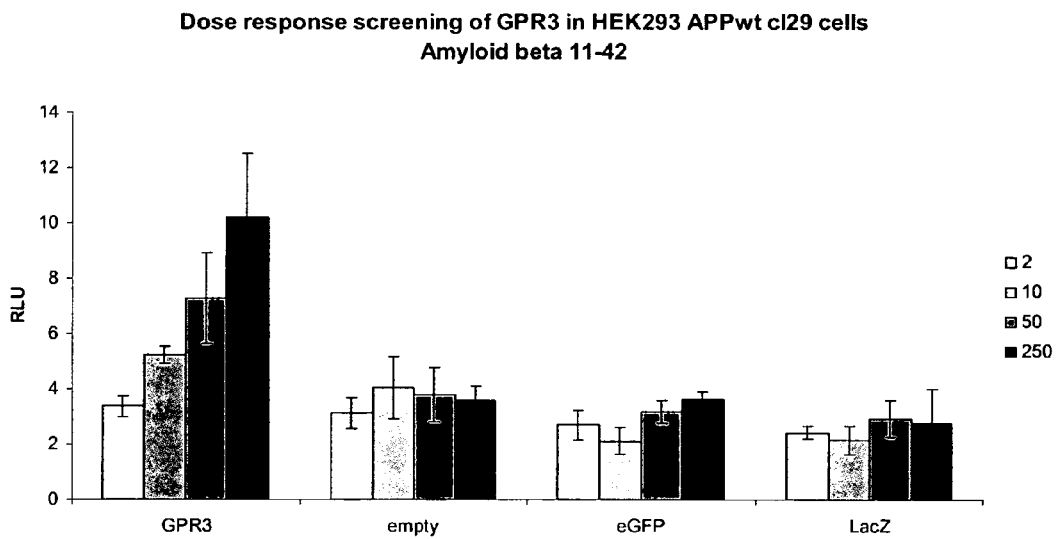

Fig 5:

Essential multiple sequence parameters :

Algorithm: ClustalW
Substitution matrix : Blossum62
Gap open penalty: 10
Gap extension penalty : 0.05

```
                *         20          *         40          *         60          *         80
GPR3   : ------------MMWGAGSPLAWLSAGS-----GNVNVSSVGPAEGPTG----------PAAPLPSPKAWDVLLC :  48
GPR6   : MNASAASLNDSQVVVAAEGAAAATAAGGPDTGEWGPPAAAALGAGGANGSLELSSQLSAGPPGLLLPAVNPWDVLLC :  80
GPR12  : --------MNEDIKVNLSGLERDYLDAAA-----AENISAVSSRVPAVE----------PEPEL-VNEWDIVLC :  52
                                                            P   Lp vnpWD66lC

*        100          *        120          *        140          *        160
GPR3   : ISGTLVSCENALVVAIIVGTPAFRAPMFLLVGSLAVADLLAGLVLHFAAVECIGSAEMSLVLVGVMAMAFTASIGSLL : 128
GPR6   : VSGTVIAGENALVVAIVALIASTPAIRTPMFVLVGSLATADLLAGCGLILHFVEQYIVPSETVSLLVGFLVASFAASVSSLL : 160
GPR12  : TSGTLISCENAIVLIFHNPSLRAPMFLLIGSLALADLLAGIGLITNEVEAVILQSEATKLVILGIIVASFSASVCSLL : 132
         SGT66scENA6VVa6I  tPalRaPMF6L6GSLa ADLLAG GL6lhFvf 5l6  Se  sl6t6G 6vasF AS6  SLL

*        180          *        200          *        220          *        240
GPR3   : AITVDRYLSLYNALTYMSETTVRTYVMIALVWGGALGLGLLPVLAWNCIDGLTTCGVVYPISKNHIVVLIAIAFFMVFGI : 208
GPR6   : AITVDRYLSLYNALTYMSRRTILGVHLLIAATWTVSLGIGLPVLGWNCIAERAACSVVRPIARSHVALISAAFFMVFGI : 240
GPR12  : AITVDRYLSLYALTYHSERTVFTYVMIVMLWGTSICLGLILPVMGWNCIRDESTICSVVRPLLKNNAAILSVSFLFMFAL : 212
         AITVDRYLSLYnALTYySerT6t ty66la  Wg s6gLGLLPV6gWNCL     tCsVVrPL 4nh a6Ls aFfm6Fg6

*        260          *        280          *        300          *        320
GPR3   : MLQLYAQICRIVCRHAQQIALQRHLLPASHYVATRKGIATLAVVLGAFAAQWLPFTVYCLLGDAHSPPLYTYLTLLPATY : 288
GPR6   : MHLYMRICQVVWRHAHQIALQQHCIAPPHLAATRKGVGTLAVVLGTHGASWLPFAIYCVVGSHEDPAVYTYATLLPATY : 320
GPR12  : MLQLYHQICKIVMRHAHQIALQHHFLATSHYVTTRKGVSTLAILILGLHEFAACWMPFFLYSLLADYTYPSIYTYATLLPATY : 292
         MLqly qIC 6V  RHAhQIALQ H  La  sHyvaTRKG6 TLA66LGt FaAcW6PFt6Yc66gd    P 6YTYaTLLPATY

*        340          *        360
GPR3   : NSMINPIIYAFRNQDVQKVLWAVCCCSSSKIPFRSRSPSDV : 330
GPR6   : NSMINPIIYAFRNQEIQRALWLLCGGCFQSKVPERSRSPSEV : 362
GPR12  : NSINPVIYAFRNQEIQKALCIICCGIPSSLAQRARSPSDV : 334
         NS6INP6IYAFRNQe6Q4aLwl6cCgC Sk6pfRsRSPSdv
```

METHODS FOR IDENTIFYING A COMPOUND THAT INHIBITS THE PROCESSION OF AMYLOID-BETA PROTEIN PRODUCTION IN A MAMMALIAN CELL EXPRESSING APP AND OVEREXPRESSING A G-PROTEIN COUPLED RECEPTOR IN THE CELL

CROSS-REFERENCE TO RELATED APPLICATIONS

This application claims priority to U.S. Provisional Application No. 60/563,661, filed Apr. 20, 2004, the disclosure of which is incorporated herein by reference.

FIELD OF THE INVENTION

This invention relates to the field of mammalian neuronal cell disorders, and in particular, to methods for identifying effective compounds, and therapies and compositions using such compounds, useful for the prevention and treatment of diseases associated with progressive loss of intellectual capacities in humans.

The neurological disorder that is most widely known for its progressive loss of intellectual capacities is Alzheimer's disease (AD). Worldwide, about 20 million people suffer from Alzheimer's disease. AD is clinically characterized by the initial loss of memory, followed by disorientation, impairment of judgment and reasoning, which is commonly referred to as cognitive impairment, and ultimately by full dementia. AD patients finally lapse into a severely debilitated, immobile state between four and twelve years after onset of the disease.

The key pathological evidence for AD is the presence of extracellular amyloid plaques and intracellular tau tangles in the brain, which are associated with neuronal degeneration (Ritchie and Lovestone (2002)). The extracellular amyloid plaques are believed to result from an increase in the insoluble amyloid beta peptide 1-42 produced by the metabolism of amyloid-beta precursor protein (APP). Following secretion, these amyloid beta 1-42 peptides form amyloid fibrils more readily than the amyloid beta 1-40 peptides, which are predominantly produced in healthy people. It appears that the amyloid beta peptide is on top of the neurotoxic cascade: experiments show that amyloid beta fibrils, when injected into the brains of P301L tau transgenic mice, enhance the formation of neurofibrillary tangles (Gotz et al. (2001)). In fact, a variety of amyloid beta peptides have been identified as amyloid beta peptides 1-42, 1-40, 1-39, 1-38, 1-37, which can be found in plaques and are often seen in cerebral spinal fluid.

The amyloid beta peptides are generated (or processed) from the membrane anchored APP, after cleavage by beta secretase and gamma secretase at position 1 and 40 or 42, respectively (FIG. 1A)(Annaert and De Strooper (2002)). In addition, high activity of beta secretase results in a shift of the cleavage at position 1 to position 11. Cleavage of amyloid-beta precursor protein by alpha secretase activity at position 17 and gamma secretase activity at 40 or 42 generates the non-pathological p3 peptide. Beta secretase was identified as the membrane anchored aspartyl protease BACE, while gamma secretase is a protein complex comprising presenilin 1 (PS1) or presenilin 2 (PS2), nicastrin, Anterior Pharynx Defective 1 (APH1) and Presenilin Enhancer 2 (PEN2). Of these proteins, the presenilins are widely thought to constitute the catalytic activity of the gamma secretase, while the other components play a role in the maturation and localization of the complex. The identity of the alpha secretase is still illustrious, although some results point towards the proteases ADAM10 and TACE, which could have redundant functions.

A small fraction of AD cases (mostly early onset AD) are caused by autosomal dominant mutations in the genes encoding presenilin 1 and 2 (PS1; PS2) and the amyloid-beta precursor protein (APP), and it has been shown that mutations in APP, PS1 and PS2 alter the metabolism of amyloid-beta precursor protein leading to such increased levels of amyloid beta 1-42 produced in the brain. Although no mutations in PS1, PS2 and amyloid-beta precursor protein have been identified in late onset AD patients, the pathological characteristics are highly similar to the early onset AD patients. These increased levels of amyloid beta peptide could originate progressively with age from disturbed amyloid-beta precursor protein processing (e.g. high cholesterol levels enhance amyloid beta peptide production) or from decreased amyloid beta peptide catabolism. Therefore, it is generally accepted that AD in late onset AD patients is also caused by aberrant increased amyloid peptide levels in the brains. The level of these amyloid beta peptides, and more particularly amyloid-beta peptide 1-42, is increased in Alzheimer patients compared to the levels of these peptides in healthy persons. Thus, reducing the levels of these amyloid beta peptides is likely to be beneficial for patients with cognitive impairment.

Reported Developments

The major current AD therapies are limited to delaying progressive memory loss by inhibiting the acetylcholinesterase enzyme, which increases acetylcholine neurotransmitter levels, which fall because the cholinergic neurons are the first neurons to degenerate during AD. This therapy does not halt the progression of the disease.

Therapies aimed at decreasing the levels of amyloid beta peptides in the brain, are increasingly being investigated and focus on the perturbed amyloid-beta precursor protein processing involving the beta- or gamma secretase enzymes.

The present invention is based on the discovery that certain known polypeptides are factors in the up-regulation and/or induction of amyloid beta precursor processing in neuronal cells, and that the inhibition of the function of such polypeptides are effective in reducing levels of amyloid beta peptides.

SUMMARY OF THE INVENTION

The present invention relates to the relationship between the function of the G-protein coupled receptor(s) ("GPCR(s)") and amyloid-beta precursor protein processing in mammalian cells.

One aspect of the present invention is a method for identifying a compound that inhibits the processing of amyloid-beta precursor protein in a mammalian cell, comprising (a) contacting a compound with a polypeptide comprising an amino acid sequence selected from the group consisting of SEQ ID NO: 4-6, 289-333; and (b) measuring a compound-polypeptide property related to the production of amyloid-beta protein.

Aspects of the present method include the in vitro assay of compounds using polypeptide domains of a GPCR, and cellular assays wherein GPCR inhibition is followed by observing indicators of efficacy, including second messenger levels and/or amyloid beta peptide levels.

Another aspect of the invention is a method of treatment or prevention of a condition involving cognitive impairment, or a susceptibility to the condition, in a subject suffering or susceptible thereto, by administering a pharmaceutical composition comprising an effective amyloid-beta precursor processing-inhibiting amount of a GPCR antagonist or inverse agonist.

A further aspect of the present invention is a pharmaceutical composition for use in said method wherein said inhibitor comprises a polynucleotide selected from the group of an antisense polynucleotide, a ribozyme, and a small interfering RNA (siRNA), wherein said agent comprises a nucleic acid sequence complementary to, or engineered from, a naturally occurring polynucleotide sequence encoding a polypeptide comprising an amino acid sequence selected from the group consisting of SEQ ID NO: 4-6.

Another further aspect of the present invention is a pharmaceutical composition comprising a therapeutically effective amyloid-beta precursor processing-inhibiting amount of a GPCR antagonist or inverse agonist or its pharmaceutically acceptable salt, hydrate, solvate, or prodrug thereof in admixture with a pharmaceutically acceptable carrier. The present polynucleotides and GPCR antagonist and inverse agonist compounds are also useful for the manufacturing of a medicament for the treatment of Alzheimer's disease.

BRIEF DESCRIPTION OF THE DRAWINGS

FIG. 3: Involvement of GPR3 in APP processing: HEK293 APPwt cells are transduced with Ad5/GPR3 and with negative control viruses (Ad5/empty, Ad5/LacZ, Ad5/eGFP and Ad5/luciferase) at different MOIs (2, 10, 50, 250). Resulting amyloid beta 1-42, 1-40, 11-42, x-42 and 1-x peptides were measured with the appropriate ELISAs. Data are represented in pM or as relative light units (rlu), which correlates to pM of amyloid beta.

FIG. 5: ClustalW protein sequence alignment of GPR3, GPR6 and GPR12.

DETAILED DESCRIPTION

Figure 1A:
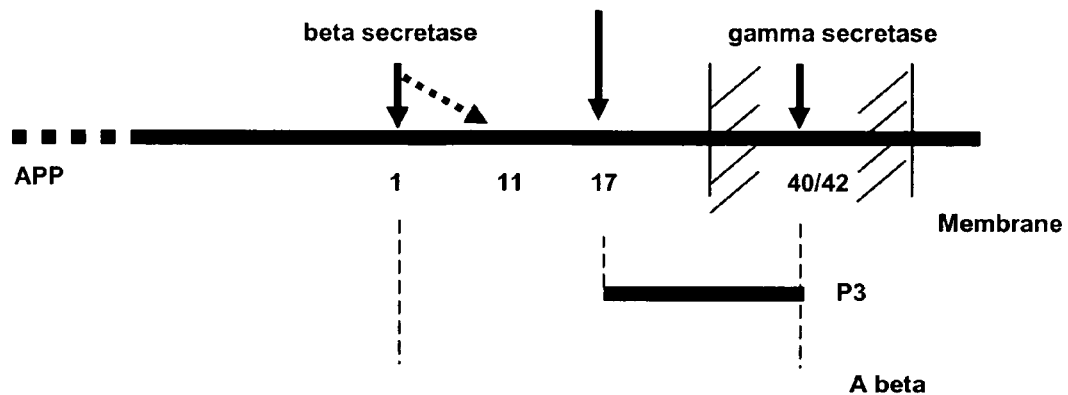
FIG. 1A: APP processing: The membrane anchored amyloid precursor protein (APP) is processed by two pathways: the amyloidogenic and non amyloidogenic pathway. In the latter pathway, APP is cleaved first by alpha secretase and then by gamma secretase, yielding the p3 peptides (17-40 or 17-42). The amyloidogenic pathway generates the pathogenic amyloid beta peptides (A beta) after cleavage by beta- and gamma-secretase respectively. The numbers depicted are the positions of the amino acids comprising the A beta sequences.

The following terms are intended to have the meanings presented therewith below and are useful in understanding the description of and intended scope of the present invention.

Definitions:

The term "agonist" refers to a ligand that activates the intracellular response of the receptor to which the agonist binds.

The term "amyloid beta peptide" means amyloid beta peptides processed from the amyloid beta precursor protein (APP). The most common peptides include amyloid beta peptides 1-40, 1-42, 11-40 and 11-42. Other species less prevalent amyloid beta peptides are described as y-42, whereby y ranges from 2-17, and 1-x whereby x ranges from 24-39 and 41.

The term "antagonist" means a moiety that bind competitively to the receptor at the same site as the agonists but which do not activate the intracellular response initiated by the active form of the receptor, and can thereby inhibit the intracellular responses by agonists. Antagonists do not diminish the baseline intracellular response in the absence of an agonist or partial agonist.

The term "carrier" means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannosek, or dextrins; chelating agents such as EDTA; sugar alcohols such as mannitol or sorbitol; salt-forming counter ions such as sodium; and/or nonionic surfactants such as TWEEN.TM., polyethylene glycol (PEG), and PLURONIC-S.TM.

The term "compound" is used herein in the context of a "test compound" or a "drug candidate compound" described in connection with the assays of the present invention. As such, these compounds comprise organic or inorganic compounds, derived synthetically or from natural sources. The compounds include inorganic or organic compounds such as polynucleotides, lipids or hormone analogs that are characterized by relatively low molecular weights. Other biopolymeric organic test compounds include peptides comprising from about 2 to about 40 amino acids and larger polypeptides comprising from about 40 to about 500 amino acids, such as antibodies or antibody conjugates.

The term "constitutive receptor activation" means stabilization of a receptor in the active state by means other than binding of the receptor with its endogenous ligand or a chemical equivalent thereof.

The term "contact" or "contacting" means bringing at least two moieties together, whether in an in vitro system or an in vivo system.

The term "condition" or "disease" means the overt presentation of symptoms (i.e., illness) or the manifestation of abnormal clinical indicators (e.g., biochemical indicators), resulting from defects in one amyloid beta protein precursor processing. Alternatively, the term "disease" refers to a genetic or environmental risk of or propensity for developing such symptoms or abnormal clinical indicators.

The term "endogenous" shall mean a material that a mammal naturally produces. Endogenous in reference to, for example and not limitation, the term "receptor" shall mean that which is naturally produced by a mammal (for example, and not limitation, a human) or a virus. In contrast, the term non-endogenous in this context shall mean that which is not naturally produced by a mammal (for example, and not limitation, a human) or a virus. For example, and not limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and not a limitation, in a screening approach, the endogenous or non-endogenous receptor may be in reference to an in vitro screening system. As a further example and not limitation, where the genome of a mammal has been manipulated to include a non-endogenous constitutively activated receptor, screening of a candidate compound by means of an in vivo system is viable.

The term "expression" comprises both endogenous expression and overexpression by transduction.

The term "expressible nucleic acid" means a nucleic acid coding for a proteinaceous molecule, an RNA molecule, or a DNA molecule.

The term "hybridization" means any process by which a strand of nucleic acid binds with a complementary strand through base pairing. The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed). The term "stringent conditions" refers to conditions that permit hybridization between polynucleotides and the claimed polynucleotides. Stringent conditions can be defined by salt concentration, the concentration of organic solvent, e.g., formamide, temperature, and other conditions well known in the art. In particular, reducing the concentration of salt, increasing the concentration of formamide, or raising the hybridization temperature can increase stringency.

The term "inhibit" or "inhibiting", in relationship to the term "response" means that a response is decreased or prevented in the presence of a compound as opposed to in the absence of the compound.

The term "inverse agonist" mean a moiety that binds the endogenous form of the receptor, and which inhibits the baseline intracellular response initiated by the active endogenous form of the receptor below the normal base level of activity that is observed in the absence of the endogenous ligand, or agonists, or decrease GTP binding to membranes. Preferably, the baseline intracellular response is decreased in the presence of the inverse agonist by at least 30%, more preferably by at least 50%, and most preferably by at least 75%, as compared with the baseline response in the absence of the inverse agonist.

The term "ligand" means an endogenous, naturally occurring molecule specific for an endogenous, naturally occurring receptor.

The term "pharmaceutically acceptable prodrugs" as used herein means the prodrugs of the compounds useful in the present invention, which are, within the scope of sound medical judgment, suitable for use in contact with the tissues of patients with undue toxicity, irritation, allergic response commensurate with a reasonable benefit/risk ratio, and effective for their intended use of the compounds of the invention. The term "prodrug" means a compound that is transformed in vivo to yield an effective compound useful in the present invention or a pharmaceutically acceptable salt, hydrate or solvate thereof. The transformation may occur by various mechanisms, such as through hydrolysis in blood. The compounds bearing metabolically cleavable groups have the advantage that they may exhibit improved bioavailability as a result of enhanced solubility and/or rate of absorption conferred upon the parent compound by virtue of the presence of the metabolically cleavable group, thus, such compounds act as prodrugs. A thorough discussion is provided in Design of Prodrugs, H. Bundgaard, ed., Elsevier (1985); Methods in Enzymology; K. Widder et al, Ed., Academic Press, 42, 309-396 (1985); A Textbook of Drug Design and Development, Krogsgaard-Larsen and H. Bandaged, ed., Chapter 5; "Design and Applications of Prodrugs" 113-191 (1991); Advanced Drug Delivery Reviews, H. Bundgard, 8, 1-38, (1992); J. Pharm. Sci., 77, 285 (1988); Chem. Pharm. Bull., N. Nakeya et al, 32, 692 (1984); Pro-drugs as Novel Delivery Systems, T. Higuchi and V. Stella, 14 A.C.S. Symposium Series, and Bioreversible Carriers in Drug Design, E. B. Roche, ed., American Pharmaceutical Association and Pergamon Press, 1987, which are incorporated herein by reference. An example of the prodrugs is an ester prodrug. "Ester prodrug" means a compound that is convertible in vivo by metabolic means (e.g., by hydrolysis) to an inhibitor compound according to the present invention. For example an ester prodrug of a compound containing a carboxy group may be convertible by hydrolysis in vivo to the corresponding carboxy group.

The term "pharmaceutically acceptable salts" refers to the non-toxic, inorganic and organic acid addition salts, and base addition salts, of compounds of the present invention. These salts can be prepared in situ during the final isolation and purification of compounds useful in the present invention.

The term "polynucleotide" means a polynucleic acid, in single or double stranded form, and in the sense or antisense orientation, complementary polynucleic acids that hybridize to a particular polynucleic acid under stringent conditions, and polynucleotides that are homologous in at least about 60 percent of its base pairs, and more preferably 70 percent of its base pairs are in common, most preferably 90 percent, and in a special embodiment 100 percent of its base pairs. The polynucleotides include polyribonucleic acids, polydeoxyribonucleic acids, and synthetic analogues thereof. The polynucleotides are described by sequences that vary in length, that range from about 10 to about 5000 bases, preferably about 100 to about 4000 bases, more preferably about 250 to about 2500 bases. A preferred polynucleotide embodiment comprises from about 10 to about 30 bases in length. A special embodiment of polynucleotide is the polyribonucleotide of from about 10 to about 22 nucleotides, more commonly described as small interfering RNAs (siRNAs). Another special embodiment are nucleic acids with modified backbones such as peptide nucleic acid (PNA), polysiloxane, and 2'-O-(2-methoxy)ethylphosphorothioate, or including non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection.

The term "polypeptide" relates to proteins, proteinaceous molecules, fractions of proteins (such as kinases, proteases, GPCRs), peptides and oligopeptides.

The term "solvate" means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

The term "subject" includes humans and other mammals.

The term "effective amount" or "therapeutically effective amount" means that amount of a compound or agent that will elicit the biological or medical response of a subject that is being sought by a medical doctor or other clinician. In particular, with regard to treating an neuronal disorder, the term "effective amount" is intended to mean that effective amyloid-beta precursor processing inhibiting amount of an compound or agent that will bring about a biologically meaningful decrease in the levels of amyloid beta peptide in the subject's brain tissue.

The term "treating" means an intervention performed with the intention of preventing the development or altering the pathology of, and thereby alleviating a disorder, disease or condition, including one or more symptoms of such disorder or condition. Accordingly, "treating" refers to both therapeutic treatment and prophylactic or preventative measures. Those in need of treating include those already with the disorder as well as those in which the disorder is to be prevented. The related term "treatment," as used herein, refers to the act of treating a disorder, symptom, disease or condition, as the term "treating" is defined above.

The background of the present inventors' discovery is described briefly below.

Background of the G-Protein Couple Receptors:

In 1994, Marchese and co-workers cloned the GPR3 gene (Marchese et al., 1994) and one year later, it was found that a single exon encoded this receptor protein of 330 amino acids, also called adenylate cyclase constitutive activator (ACCA). Based on the amino acid sequence, GPR3 can be classified in the same sub-family as GPR6 and GPR12: GPR3 and GPR6 exhibit 58% identity, and GPR3 and GPR12 57% (FIG. 5).

Figure 1B:
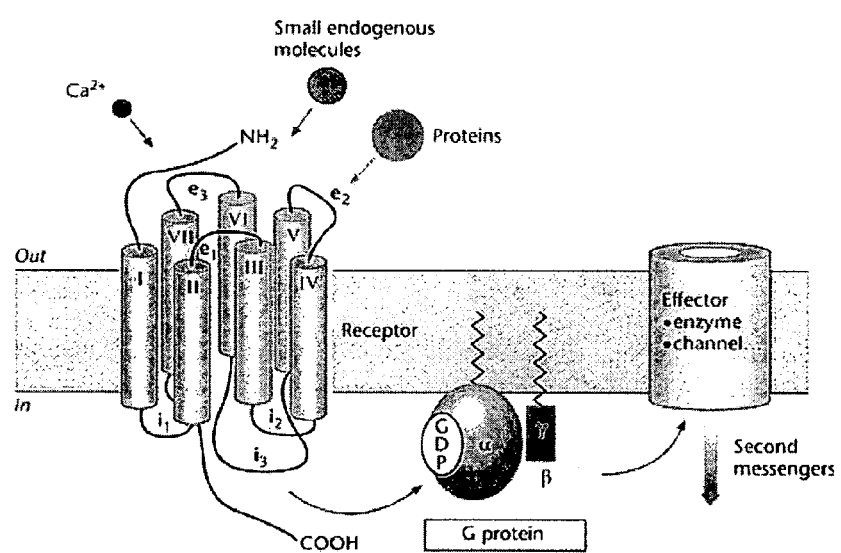
FIG. 1B: Pictorial representation of transmembrane structure of GPCR proteins.

G protein-coupled receptors (GPCR) share a common structural motif. All these receptors have seven sequences of between 22 to 24 hydrophobic amino acids that form seven alpha helices, each of which spans the membrane forming 7 transmembrane domains, an extracellular N-terminus and an intracellular C-terminus. The transmembrane helices are joined by strands of amino acids having a larger loop between the fourth and fifth transmembrane helix on the extracellular side of the membrane. Another larger loop, composed primarily of hydrophilic amino acids, joins transmembrane helices five and six on the intracellular side of the membrane. See FIG. 1B.

Under physiological conditions, GPCRs exist in the cell membrane in equilibrium between two different states or conformations: an "inactive" state and an "active" state. A receptor in an inactive state is unable to link to the intracellular transduction pathway to produce a biological response. Changing the receptor conformation to the active state allows linkage to the transduction pathway and produces a biological response. A receptor may be stabilized in an active state by an endogenous ligand or an exogenous agonist ligand. Recent discoveries, including but not exclusively limited to, modifications to the amino acid sequence of the receptor, provide alternative mechanisms other than ligands to stabilize the active state conformation. These approaches effectively stabilize the receptor in an active state by simulating the effect of a ligand binding to the receptor. Stabilization by such ligand-independent approaches is termed "constitutive receptor activation."

The major signal transduction cascades activated by GPCRs are initiated by the activation of heterotrimeric G-proteins, built from three different proteins; the $G_\alpha$, $G_\beta$ and $G_\gamma$ subunits. It is believed that the loop joining helices five and six, as well as the carboxy terminus, interact with the G protein. Uhlenbrock and colleagues (2002) showed that GPR3, GPR6 and GPR12 all confer constitutive activation of G(a)(s) and G(a)(i/o), and, recently, sphingosine-1-phosphate (SIP) and dihydrosphingosine 1-phosphate (DHS1P) have been identified as bioactive lipid ligands for GPR3, GPR6 and GPR12 (Uhlenbrock et al., 2002). The GPR3, GPR6 and GPR12 expression profile is also similar: they are all primary expressed in brain tissue.

The signal transduction cascade starts with the activation of the receptor by an agonist. Transformational changes in the receptor are then translated down to the G-protein. The G-protein dissociates into the $G_\alpha$ subunit and the $G_{\beta\gamma}$ subunit. Both subunits dissociate from the receptor and are both capable of initiating different cellular responses. Best known are the cellular effects that are initiated by the $G_\alpha$ subunit. It is for this reason that G-proteins are categorized by their $G_\alpha$ subunit. The G-proteins are divided into four groups: $G_s$, $G_{i/o}$, $G_q$ and $G_{12/13}$. Each of these G-proteins is capable of activating an effector protein, which results in changes in second messenger levels in the cell. The changes in second messenger level are the triggers that make the cell respond to the extracellular signal in a specific manner. The activity of a GPCR can be measured by measuring the activity level of the second messenger.

The two most important second messengers in the cell are cAMP and $Ca^{2+}$. The α-subunit of the $G_s$ class of G-proteins is able to activate adenylyl cyclase, resulting in an increased turnover from ATP to cAMP. The α-subunit of $G_{i/o}$ G-proteins does exactly the opposite and inhibits adenylyl cyclase activity resulting in a decrease of cellular cAMP levels. Together, these two classes of G-proteins regulate the second messenger cAMP. $Ca^{2+}$ is regulated by the α-subunit of the $G_q$ class of G-proteins. Through the activation of phospholipase C phosphatidylinositol 4,5-bisphosphate (PIP2) from the cell membrane are hydrolyzed to inositol 1,4,5-trisphosphate and 1,2-diacylglycerol, both these molecules act as second messengers. Inositol 1,4,5-trisphosphate binds specific receptors in the endoplasmatic reticulum, resulting in the opening of $Ca^{2+}$ channels and release of $Ca^{2+}$ in the cytoplasm.

No clear functions have been assigned to the GPCRs. The expression level of GPR3 and of GPR12 is increased in human umbilical vein endothelial cells after shear stress (Uhlenbrock et al., 2003). Since sphingosine-1-phosphate is a ligand for GPR3 and GPR12, the above data suggest a role for both GPCRs in sphingosine-1-phosphate-mediated intracellular signaling in human endothelial cells. As the expression of GPR3 and GPR6 is also differentially regulated in rodent obesity models, both GPCRs (+GPR12) are considered as putative drug targets in appetite, hunger and satiety control.

GPR12, on the other hand, seems to be involved in the differentiation and maturation of post mitotic neurons (Ignatov et al., 2003).

REFERENCES

Annaert, W. and B. De Strooper (2002). "A cell biological perspective on Alzheimer's disease." Annu Rev Cell Dev Biol 18: 25-51.

Gotz, J., F. Chen, et al. (2001). "Formation of neurofibrillary tangles in P301l tau transgenic mice induced by Abeta 42 fibrils." Science 293(5534): 1491-5.

Ignatov, A.; Lintzel, J.; Hermans-Borgmeyer, I.; Kreienkamp, H.-J., Joost, P.; Thomsen, S.; Methner, A. And Schaller, H. C. (2003). Role of the G-protein-coupled receptor GPR12 as high-affinity receptor for sphingosylphosphorylcholine and its expression and function in brain development. J. Neurosci. 23, 3: 907-914.

Lipinski, C. A., Lombardo, F., Dominy, B. W., and Feeney, P. J. Adv. Drug. Deliv. Rev., 23, 3-25, 1997

Marchese, A.; Docherty, J M.; Nguyen, T.; Heiber, M.; Cheng, R.; Heng, H H.; Tsui, L C.; Shi, X.; George S R. and O'Dowd, B F. (1994). Cloning of human genes encoding novel G protein-coupled receptors. Genomics, 23, 3: 609-618.

Marinissen, M. J. and J. S. Gutkind (2001). "G-protein-coupled receptors and signaling networks: emerging paradigms." Trends Pharmacol Sci 22(7): 368-76.

Ritchie, K. and S. Lovestone (2002). "The dementias." Lancet 360(9347): 1759-66.

Uhlenbrock, K.; Gassenhuber, H. And Kostenis, E. (2002). Sphingosine-1-phosphate is a ligand of the human GPR3, GPR6 and GPR12 family of constitutively active G protein-coupled receptors. Cell Signal, 14, 11: 941-953.

Uhlenbrock, K.; Huber, J.; Ardati, A.; Bush, A E. And Kostenis, E. (2003). Fluid shear stress differentially regulates GPR3, GPR6 and GPR12 expression in human umbilical vein endothelial cells. Cell Physiol. Biochem. 13, 2: 75-84.

Wess, J. (1998). "Molecular basis of receptor/G-protein-coupling selectivity." Pharmacol Ther 80(3): 231-64.

Applicants' Invention Based on GPCR Relationship to Amyloid Beta Peptides

As noted above, the present invention is based on the present inventors' discovery that the G-protein coupled receptor(s) ("GPCR(s)") are factors in the up-regulation and/or induction of amyloid beta precursor processing in mammalian, and principally, neuronal cells, and that the inhibition of the function of such polypeptides is effective in reducing levels of amyloid beta protein peptides.

The present inventors are unaware of any prior knowledge linking GPCRs, and more particularly GPR3, and amyloid beta peptide formation and secretion. As discussed in more detail in the Experimental section below, the present inventors demonstrate that the overexpression of GPR3 increases, and the knockdown of GPR3 reduces, amyloid beta 1-42 in the conditioned medium of transduced cells. The present invention is based on these findings and the recognition that the GPCRs are putative drug targets for Alzheimer's disease, since the predominant expression of GPR3, GPR6 and GPR12 is in the tissue of the central nervous system.

One aspect of the present invention is a method based on the aforesaid discovery for identifying a compound that inhibits the processing of amyloid-beta precursor protein in a mammalian cell, and may therefore be useful in reducing amyloid beta peptide levels in a subject. The present method comprises contacting a drug candidate compound with a GPCR polypeptide, or a fragment of said polypeptide, and measuring a compound-polypeptide property related to the production of amyloid-beta protein. The "compound-polypeptide property" is a measurable phenomenon chosen by the person of ordinary skill in the art, and based on the recognition that GPCR activation and deactivation is a causative factor in the activation and deactivation, respectively, of amyloid beta protein precursor processing, and an increase and decrease, respectively, of amyloid beta peptide levels. The measurable property may range from the binding affinity for a peptide domain of the GPCR polypeptide, to the level of any one of a number of "second messenger" levels resulting from the activation or deactivation of the GPCR, to a reporter molecule property directly linked to the aforesaid second messenger, and finally to the level of amyloid beta peptide secreted by the mammalian cell contacted with the compound.

Depending on the choice of the skilled artisan, the present assay method may be designed to function as a series of measurements, each of which is designed to determine whether the drug candidate compound is indeed acting on the GPCR to amyloid beta peptide pathway. For example, an assay designed to determine the binding affinity of a compound to the GPCR, or fragment thereof, may be necessary, but not sufficient, to ascertain whether the test compound would be useful for reducing amyloid beta peptide levels when administered to a subject. Nonetheless, such binding information would be useful in identifying a set of test compounds for use in an assay that would measure a different property, further down the biochemical pathway. Such second assay may be designed to confirm that the test compound, having binding affinity for a GPCR peptide, actually down-regulates or inhibits, as an agonist or inverse agonist, GPCR function in a mammalian cell. This further assay may measure a second messenger that is a direct consequence of the activation or deactivation of the GPCR, or a synthetic reporter system responding to the messenger. Measuring a different second messenger, and/or confirming that the assay system itself is not being affected directly and not the GPCR pathway may further validate the assay. In this latter regard, suitable controls should always be in place to insure against false positive readings.

The order of taking these measurements is not believed to be critical to the practice of the present invention, which may be practiced in any order. For example, one may first perform a screening assay of a set of compounds for which no information is known respecting the compounds' binding affinity for GPCR. Alternatively, one may screen a set of compounds identified as having binding affinity for a GPCR peptide domain, or a class of compounds identified as being agonist or inverse agonists of a GPCR. It is not essential to know the binding affinity for GPCR due to the possible compound interaction in the intra-membrane domain of the GPCR polypeptide, which domain conformation may not be possible to reproduce in an affinity experiment. However, for the present assay to be meaningful to the ultimate use of the drug candidate compounds, a measurement of the second messenger(s), or the ultimate amyloid beta peptide levels, is necessary. Validation studies including controls, and measurements of binding affinity to GPCR are nonetheless useful in identifying a compound useful in any therapeutic or diagnostic application.

The present assay method may be practiced in vitro, using one or more of the GPCR proteins, or fragments thereof, or membrane preparations made from cells transduced with vectors over-expressing the GPCR polypeptides. The amino acid sequences of the GPCRs, and useful fragments thereof are found in SEQ ID NO: 4-6, 289-333. The binding affinity of the compound with the polypeptide can be measured by methods known in the art, such as using surface plasmon resonance biosensors (Biacore), by saturation binding analysis with a labeled compound (e.g. Scatchard and Lindmo analysis), by differential UV spectrophotometer, fluorescence polarization assay, Fluorometric Imaging Plate Reader (FLIPR®) system, Fluorescence resonance energy transfer, and Bioluminescence resonance energy transfer. The binding affinity of compounds can also be expressed in dissociation constant (Kd) or as IC50 or EC50. The IC50 represents the concentration of a compound that is required for 50% inhibition of binding of another ligand to the polypeptide. The EC50 represents the concentration required for obtaining 50% of the maximum effect in any assay that measures receptor function. The dissociation constant, Kd, is a measure of how well a ligand binds to the polypeptide, it is equivalent to the ligand concentration required to saturate exactly half of the binding-sites on the polypeptide. Compounds with a high affinity binding have low Kd, IC50 and EC50 values, i.e. in the range of 100 nM to 1 pM; a moderate to low affinity binding relates to a high Kd, IC50 and EC50 values, i.e. in the micromolar range.

The present assay method may also be practiced in a cellular assay. A host cell expressing a GPCR polypeptide can be a cell with endogenous expression of the polypeptide or a cell over-expressing the polypeptide e.g. by transduction. When the endogenous expression of the polypeptide is not sufficient to determine a baseline that can easily be measured, one may use using host cells that over express GPCR. Overexpression has the advantage that the level of the second messenger is higher than the activity level by endogenous expression. Accordingly, measuring such levels using presently available techniques is easier. In such cellular assay, the biological activity of the GPCR may be measured using a second messenger, such as cyclic AMP or Ca2+, cyclic GMP, inositol triphosphate ($IP_3$) and/or diacylglycerol (DAG). Cyclic AMP or Ca2+ are preferred second messengers to measure. Second messenger activation may be measured by several different techniques, either directly by ELISA or radioactive technologies or indirectly by reporter gene analysis, discussed below. Preferably the method further comprises contacting the host cell with an agonist for GPCR before determining the baseline level. The addition of an agonist further stimulates GPCR, thereby further increasing the activity level of the second messenger. Several such agonists (ligands) are known in the art; preferentially the agonist is spingosine-1-phosphate or dihydrosphingosine-1-phosphate. The GPCR polypeptides, when over expressed or activated the level of secreted amyloid beta peptides.

The present invention further relates to a method for identifying a compound that inhibits amyloid-beta precursor protein processing in a mammalian cell comprising:
(a) contacting a compound with a polypeptide comprising an amino acid sequence selected from the group consisting of SEQ ID NO: 4-6,
(b) determining the binding affinity of the compound to the polypeptide,
(c) contacting a population of mammalian cells expressing said polypeptide with the compound that exhibits a binding affinity of at least 10 micromolar, and
(d) identifying the compound that inhibits the amyloid-beta precursor protein processing in the cells.

A further embodiment of the present invention relates a method to identify a compound that inhibits the amyloid-beta precursor protein processing in a cell, wherein the activity level of the GPCR polypeptide is measured by determining the level of one or more second messengers, wherein the level of the one or second messenger is determined with a reporter controlled by a promoter, which is responsive to the second messenger. The reporter is a reporter gene under the regulation of a promoter that responds to the cellular level of second messengers. Such preferred second messengers are Cyclic AMP or Ca2+. The reporter gene should have a gene product that is easily detected, and that may be stably infected in the host cell. Such methods are well known by any person with ordinary skill in the art.

The reporter gene may be selected from alkaline phosphatase, green fluorescent protein (GFP), enhanced green fluorescent protein (eGFP), destabilized green fluorescent protein (dGFP), luciferase, beta-galactosidase among others. The reporter is preferably luciferase or beta-galactosidase, which are readily available and easy to measure over a large range The promoter in the reporter construct is preferably a cyclic AMP-responsive promoter, an NF-KB responsive promoter, or a NF-AT responsive promoter. The cyclic-AMP responsive promoter is responsive to the cyclic-AMP levels in the cell. The NF-AT responsive promoter is sensitive to cytoplasmic $Ca^{2+}$-levels in the cell. The NF-KB responsive promoter is sensitive for activated NF-κB levels in the cell.

A further embodiment of the present invention relates a method to identify a compound that inhibits the amyloid-beta precursor protein processing in a cell, wherein the activity level of the GPCR polypeptide is measured by determining the level of amyloid beta peptides. The levels of these peptides may be measured with specific ELISAs using antibodies specifically recognizing the different amyloid beta peptide species (see e.g. Example 1). Secretion of the various amyloid beta peptides may also be measured using antibodies that bind all peptides. Levels of amyloid beta peptides can also be measured by Mass spectrometry analysis.

For high-throughput purposes, libraries of compounds may be used such as antibody fragment libraries, peptide phage display libraries, peptide libraries (e.g. LOPAP™, Sigma Aldrich), lipid libraries (BioMol), synthetic compound libraries (e.g. LOPAC™, Sigma Aldrich) or natural compound libraries (Specs, TimTec).

Preferred drug candidate compounds are low molecular weight compounds. Low molecular weight compounds, i.e. with a molecular weight of 500 Dalton or less, are likely to have good absorption and permeation in biological systems and are consequently more likely to be successful drug candidates than compounds with a molecular weight above 500 Dalton (Lipinski et al. (1997)). Peptides comprise another preferred class of drug candidate compounds, since peptides are known GPCRs antagonists. Peptides may be excellent drug candidates and there are multiple examples of commercially valuable peptides such as fertility hormones and platelet aggregation inhibitors. Natural compounds are another preferred class of drug candidate compound. Such compounds are found in and extracted from natural sources, and which may thereafter be synthesized. The lipids are another preferred class of drug candidate compound. Lipids may be antagonists of the GPCRs listed in Table 2 (SEQ ID NO: 1-3, 4-6).

Another preferred class of drug candidate compounds is an antibody. The present invention also provides antibodies directed against the extracellular domains of the GPCR. These antibodies should specifically bind to one or more of the extra-cellular domains of the GPCRs, or as described further below, engineered to be endogenously produced to bind to the intra-cellular GPCR domain. These antibodies may be monoclonal antibodies or polyclonal antibodies. The present invention includes chimeric, single chain, and humanized antibodies, as well as FAb fragments and the products of a FAb expression library, and Fv fragments and the products of an Fv expression library.

In certain embodiments, polyclonal antibodies may be used in the practice of the invention. The skilled artisan knows methods of preparing polyclonal antibodies. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. Antibodies may also be generated against the intact GPCR protein or polypeptide, or against a fragment such as its extracellular domain peptides, derivatives including conjugates, or other epitope of the GPCR protein or polypeptide, such as the GPCR embedded in a cellular membrane, or a library of antibody variable regions, such as a phage display library.

It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). One skilled in the art without undue experimentation may select the immunization protocol.

In some embodiments, the antibodies may be monoclonal antibodies. Monoclonal antibodies may be prepared using methods known in the art. The monoclonal antibodies of the present invention may be "humanized" to prevent the host from mounting an immune response to the antibodies. A "humanized antibody" is one in which the complementarity determining regions (CDRs) and/or other portions of the light and/or heavy variable domain framework are derived from a non-human immunoglobulin, but the remaining portions of the molecule are derived from one or more human immunoglobulins. Humanized antibodies also include antibodies characterized by a humanized heavy chain associated with a donor or acceptor unmodified light chain or a chimeric light chain, or vice versa. The humanization of antibodies may be accomplished by methods known in the art (see, e.g. Mark and Padlan, (1994) "Chapter 4. Humanization of Monoclonal Antibodies", The Handbook of Experimental Pharmacology Vol. 113, Springer-Verlag, New York). Transgenic animals may be used to express humanized antibodies.

Human antibodies can also be produced using various techniques known in the art, including phage display libraries (Hoogenboom and Winter, (1991) J. Mol. Biol. 227:381-8; Marks et al. (1991). J. Mol. Biol. 222:581-97). The techniques of Cole, et al. and Boerner, et al. are also available for the preparation of human monoclonal antibodies (Cole, et al. (1985) Monoclonal Antibodies and Cancer Therapy, Alan R. Liss, p. 77; Boerner, et al (1991). J. Immunol., 147(1):86-95).

Techniques known in the art for the production of single chain antibodies can be adapted to produce single chain antibodies to the GPCR polypeptides and proteins of the present invention. The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively; the relevant cysteine residues are substituted with another amino acid residue or are deleted so as to prevent cross-linking.

Bispecific antibodies are monoclonal, preferably human or humanized, antibodies that have binding specificities for at least two different antigens and preferably for a cell-surface protein or receptor or receptor subunit. In the present case, one of the binding specificities is for one extracellular domain of the GPCR, the other one is for another extracellular domain of the same or different GPCR.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, (1983) Nature 305:537-9). Because of the random assortment of immunoglobulin heavy and light chains, these hybridomas (quadromas) produce a potential mixture of ten different antibody molecules, of which only one has the correct bispecific structure. Affinity chromatography steps usually accomplish the purification of the correct molecule. Similar procedures are disclosed in Trauneeker, et al. (1991) EMBO J. 10:3655-9.

According to another preferred embodiment, the assay method comprise using a drug candidate compound identified as having a binding affinity for GPCRs, and/or has already been identified as having down-regulating activity such as antagonist or inverse agonist activity vis-à-vis one or more GPCR. Examples of such compounds are the aryloxydithiourea compounds disclosed in U.S. Pat. No. 6,420,563 (WO 01/62765), hereby incorporated by reference with respect to the active inverse agonists disclosed therein.

Another aspect of the present invention relates to a method for reducing amyloid-beta precursor protein processing in a mammalian cell, comprising by contacting said cell with an expression-inhibiting agent that inhibits the translation in the cell of a polyribonucleotide encoding a GPCR polypeptide. A particular embodiment relates to a composition comprising an polynucleotide including at least one antisense strand that functions to pair the agent with the target GPCR mRNA, and thereby down-regulate or block the expression of GPCR polypeptide. The inhibitory agent preferably comprises antisense polynucleotide, a ribozyme, and a small interfering RNA (siRNA), wherein said agent comprises a nucleic acid sequence complementary to, or engineered from, a naturally occurring polynucleotide sequence encoding a polypeptide comprising an amino acid sequence selected from the group consisting of SEQ ID NO: 4-6.

A special embodiment of the present invention relates to a method wherein the expression-inhibiting agent is selected from the group consisting of antisense RNA, antisense oligodeoxynucleotide (ODN), a ribozyme that cleaves the polyribonucleotide coding for SEQ ID NO: 4-6, a small interfering RNA (siRNA) that is sufficiently homologous to a portion of the polyribonucleotide corresponding to SEQ ID NO: 4-6 such that the siRNA interferes with the translation of the GPCR polyribonucleotide to the GPCR polypeptide.

Another embodiment of the present invention relates to a method wherein the expression-inhibiting agent is a nucleic acid expressing the antisense RNA, antisense oligodeoxynucleotide (ODN), a ribozyme that cleaves the polyribonucleotide coding for SEQ ID NO: 4-6, a small interfering RNA (siRNA) that is sufficiently homologous to a portion of the polyribonucleotide corresponding to SEQ ID NO: 4-6 such that the siRNA interferes with the translation of the GPCR polyribonucleotide to the GPCR polypeptide. Preferably the expression-inhibiting agent is an antisense RNA, ribozyme, antisense oligodeoxynucleotide, or siRNA comprising a nucleotide sequence selected from the group consisting of SEQ ID NO: 7-287 and 340-620.

The down regulation of gene expression using antisense nucleic acids can be achieved at the translational or transcriptional level. Antisense nucleic acids of the invention are preferably nucleic acid fragments capable of specifically hybridizing with all or part of a nucleic acid encoding a GPCR polypeptide or the corresponding messenger RNA. In addition, antisense nucleic acids may be designed which decrease expression of the nucleic acid sequence capable of encoding a GPCR polypeptide by inhibiting splicing of its primary transcript. Any length of antisense sequence is suitable for practice of the invention so long as it is capable of down-regulating or blocking expression of a nucleic acid coding for a GPCR. Preferably, the antisense sequence is at least about 17 nucleotides in length. The preparation and use of antisense nucleic acids, DNA encoding antisense RNAs and the use of oligo and genetic antisense is known in the art.

One embodiment of expression-inhibitory agent is a nucleic acid that is antisense to a nucleic acid comprising SEQ ID NO: 1-3. For example, an antisense nucleic acid (e.g. DNA) may be introduced into cells in vitro, or administered to a subject in vivo, as gene therapy to inhibit cellular expression of nucleic acids comprising SEQ ID NO: 1-3. Antisense oligonucleotides preferably comprise a sequence containing from about 17 to about 100 nucleotides and more preferably the antisense oligonucleotides comprise from about 18 to about 30 nucleotides. Antisense nucleic acids may be prepared from about 10 to about 30 contiguous nucleotides selected from the sequences of SEQ ID NO: 1-3, expressed in the opposite orientation.

The antisense nucleic acids are preferably oligonucleotides and may consist entirely of deoxyribo-nucleotides, modified deoxyribonucleotides, or some combination of both. The antisense nucleic acids can be synthetic oligonucleotides. The oligonucleotides may be chemically modified, if desired, to improve stability and/or selectivity. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its target site, the RNA-DNA duplex activates the endogenous enzyme ribonuclease (RNase) H, which cleaves the mRNA component of the hybrid molecule.

In addition, antisense oligonucleotides with phosphoramidite and polyamide (peptide) linkages can be synthesized. These molecules should be very resistant to nuclease degradation. Furthermore, chemical groups can be added to the 2' carbon of the sugar moiety and the 5 carbon (C-5) of pyrimidines to enhance stability and facilitate the binding of the antisense oligonucleotide to its target site. Modifications may include 2'-deoxy, O-pentoxy, O-propoxy, O-methoxy, fluoro, methoxyethoxy phosphorothioates, modified bases, as well as other modifications known to those of skill in the art.

Another type of expression-inhibitory agent that reduces the levels of GPCRs are ribozymes. Ribozymes are catalytic RNA molecules (RNA enzymes) that have separate catalytic and substrate binding domains. The substrate binding sequence combines by nucleotide complementarity and, possibly, non-hydrogen bond interactions with its target sequence. The catalytic portion cleaves the target RNA at a specific site. The substrate domain of a ribozyme can be engineered to direct it to a specified mRNA sequence. The ribozyme recognizes and then binds a target mRNA through complementary base-pairing. Once it is bound to the correct target site, the ribozyme acts enzymatically to cut the target mRNA. Cleavage of the mRNA by a ribozyme destroys its ability to direct synthesis of the corresponding polypeptide. Once the ribozyme has cleaved its target sequence, it is released and can repeatedly bind and cleave at other mRNAs.

Ribozyme forms include a hammerhead motif, a hairpin motif, a hepatitis delta virus, group I intron or RNaseP RNA (in association with an RNA guide sequence) motif or Neurospora VS RNA motif. Ribozymes possessing a hammerhead or hairpin structure are readily prepared since these catalytic RNA molecules can be expressed within cells from eukaryotic promoters (Chen, et al. (1992) Nucleic Acids Res. 20:4581-9). A ribozyme of the present invention can be expressed in eukaryotic cells from the appropriate DNA vector. If desired, the activity of the ribozyme may be augmented by its release from the primary transcript by a second ribozyme (Ventura, et al. (1993) Nucleic Acids Res. 21:3249-55).

Ribozymes may be chemically synthesized by combining an oligodeoxyribonucleotide with a ribozyme catalytic domain (20 nucleotides) flanked by sequences that hybridize to the target mRNA after transcription. The oligodeoxyribonucleotide is amplified by using the substrate binding sequences as primers. The amplification product is cloned into a eukaryotic expression vector.

Ribozymes are expressed from transcription units inserted into DNA, RNA, or viral vectors. Transcription of the ribozyme sequences are driven from a promoter for eukaryotic RNA polymerase I (pol (I), RNA polymerase II (pol II), or RNA polymerase III (pol III). Transcripts from pol II or pol III promoters will be expressed at high levels in all cells; the levels of a given pol II promoter in a given cell type will depend on nearby gene regulatory sequences. Prokaryotic RNA polymerase promoters are also used, providing that the prokaryotic RNA polymerase enzyme is expressed in the appropriate cells (Gao and Huang, (1993) Nucleic Acids Res. 21:2867-72). It has been demonstrated that ribozymes expressed from these promoters can function in mammalian cells (Kashani-Sabet, et al. (1992) AntisenseRes. Dev. 2:3-15).

A particularly preferred inhibitory agent is a small interfering RNA (siRNA). siRNAs mediate the post-transcriptional process of gene silencing by double stranded RNA (dsRNA) that is homologous in sequence to the silenced RNA. siRNA according to the present invention comprises a sense strand of 17-25 nucleotides complementary or homologous to a contiguous 17-25 nucleotide sequence selected from the group of sequences described in SEQ ID NO: 1-3 and an antisense strand of 17-23 nucleotides complementary to the sense strand. The most preferred siRNA comprises sense and anti-sense strands that are 100 percent complementary to each other and the target polynucleotide sequence. Preferably the siRNA further comprises a loop region linking the sense and the antisense strand.

A self-complementing single stranded siRNA molecule polynucleotide according to the present invention comprises a sense portion and an antisense portion connected by a loop region linker. Preferably, the loop region sequence is 4-30 nucleotides long, more preferably 5-15 nucleotides long and most preferably 8 nucleotides long. In a most preferred embodiment the linker sequence is UUGCUAUA (SEQ ID NO: 288). Self-complementary single stranded siRNAs form hairpin loops and are more stable than ordinary dsRNA. In addition, they are more easily produced from vectors.

Analogous to antisense RNA, the siRNA can be modified to confirm resistance to nucleolytic degradation, or to enhance activity, or to enhance cellular distribution, or to enhance cellular uptake, such modifications may consist of modified internucleoside linkages, modified nucleic acid bases, modified sugars and/or chemical linkage the SiRNA to one or more moieties or conjugates. The nucleotide sequences are selected according to siRNA designing rules that give an improved reduction of the target sequences compared to nucleotide sequences that do not comply with these siRNA designing rules (For a discussion of these rules and examples of the preparation of siRNA, WO2004094636, published Nov. 4, 2004, and UA20030198627, are hereby incorporated by reference.

The present invention also relates to compositions, and methods using said compositions, comprising a DNA expression vector capable of expressing a polynucleotide capable of inhibiting amyloid beta protein precursor processing and described hereinabove as an expression inhibition agent.

A special aspect of these compositions and methods relates to the down-regulation or blocking of the expression of a GPCR polypeptide by the induced expression of a polynucleotide encoding an intracellular binding protein that is capable of selectively interacting with the GPCR polypeptide. An intracellular binding protein includes any protein capable of selectively interacting, or binding, with the polypeptide in the ceii in which it is expressed and neutralizing the function of the polypeptide. Preferably, the intracellular binding protein is a neutralizing antibody or a fragment of a neutralizing antibody having binding affinity to an intra-cellular domain of the GPCR polypeptide of SEQ ID NO: 4-6. More preferably, the intracellular binding protein is a single chain antibody.

A special embodiment of this composition comprises the expression-inhibiting agent selected from the group consisting of antisense RNA, antisense oligodeoxynucleotide (ODN), a ribozyme that cleaves the polyribonucleotide coding for SEQ ID NO: 4-6, and a small interfering RNA (siRNA) that is sufficiently homologous to a portion of the polyribonucleotide corresponding to SEQ ID NO: 4-6 such that the siRNA interferes with the translation of the GPCR polyribonucleotide to the GPCR polypeptide, The polynucleotide expressing the expression-inhibiting agent or the encoding an intracellular binding protein is preferably included within a vector. The polynucleic acid is operably linked to signals enabling expression of the nucleic acid sequence and is introduced into a cell utilizing, preferably, recombinant vector constructs, which will express the antisense nucleic acid once the vector is introduced into the cell. A variety of viral-based systems are available, including adenoviral, retroviral, adeno-associated viral, lentiviral, herpes simplex viral or a sendaviral vector systems, and all may be used to introduce and express polynucleotide sequence for the expression-inhibiting agents in target cells.

Preferably, the viral vectors used in the methods of the present invention are replication defective. Such replication defective vectors will usually lack at least one region that is necessary for the replication of the virus in the infected cell. These regions can either be eliminated (in whole or in part), or be rendered non-functional by any technique known to a person skilled in the art. These techniques include the total removal, substitution, partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome, which are necessary for encapsidating, the viral particles.

In a preferred embodiment, the viral element is derived from a adenovirus. Preferably, the vehicle includes an adenoviral vector packaged into an adenoviral capsid, or a functional part, derivative, and/or analogue thereof. Adenovirus biology is also comparatively well known on the molecular level. Many tools for adenoviral vectors have been and continue to be developed, thus making an adenoviral capsid a preferred vehicle for incorporating in a library of the invention. An adenovirus is capable of infecting a wide variety of cells. However, different adenoviral serotypes have different preferences for cells. To combine and widen the target cell population that an adenoviral capsid of the invention can enter in a preferred embodiment, the vehicle includes adenoviral fiber proteins from at least two adenoviruses.

In a preferred embodiment, the nucleic acid derived from an adenovirus includes the nucleic acid encoding an adenoviral late protein or a functional part, derivative, and/or analogue thereof. An adenoviral late protein, for instance an adenoviral fiber protein, may be favorably used to target the vehicle to a certain cell or to induce enhanced delivery of the vehicle to the cell. Preferably, the nucleic acid derived from an adenovirus encodes for essentially all adenoviral late proteins, enabling the formation of entire adenoviral capsids or functional parts, analogues, and/or derivatives thereof. Preferably, the nucleic acid derived from an adenovirus includes the nucleic acid encoding adenovirus E2A or a functional part, derivative, and/or analogue thereof. Preferably, the nucleic acid derived from an adenovirus includes the nucleic acid encoding at least one E4-region protein or a functional part, derivative, and/or analogue thereof, which facilitates, at least in part, replication of an adenoviral derived nucleic acid in a cell. The adenoviral vectors used in the examples of this application are exemplary of the vectors useful in the present method of treatment invention.

Certain embodiments of the present invention use retroviral vector systems. Retroviruses are integrating viruses that infect dividing cells, and their construction is known in the art. Retroviral vectors can be constructed from different types of retrovirus, such as, MoMuLV ("murine Moloney leukemia virus" MSV ("murine Moloney sarcoma virus"), HaSV ("Harvey sarcoma virus"); SNVu ("spleen necrosis virus"); RSV ("Rous sarcoma virus") and Friend virus. Lentiviral vector systems may also be used in the practice of the present invention. Retroviral systems and herpes virus system may be preferred vehicles for transfection of neuronal cells.

In other embodiments of the present invention, adeno-associated viruses ("AAV") are utilized. The AAV viruses are DNA viruses of relatively small size that integrate, in a stable and site-specific manner, into the genome of the infected cells. They are able to infect a wide spectrum of cells without inducing any effects on cellular growth, morphology or differentiation, and they do not appear to be involved in human pathologies.

In the vector construction, the polynucleotide agents of the present invention may be linked to one or more regulatory regions. Selection of the appropriate regulatory region or regions is a routine matter, within the level of ordinary skill in the art. Regulatory regions include promoters, and may include enhancers, suppressors, etc.

Promoters that may be used in the expression vectors of the present invention include both constitutive promoters and regulated (inducible) promoters. The promoters may be prokaryotic or eukaryotic depending on the host. Among the prokaryotic (including bacteriophage) promoters useful for practice of this invention are lac, lacZ, T3, T7, lambda P.sub.r, P.sub.1, and trp promoters. Among the eukaryotic (including viral) promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells, or Flt and Flk promoters active in endothelial cells), including animal transcriptional control regions, which exhibit tissue specificity and have been utilized in transgenic animals: elastase I gene control region which is active in pancreatic acinar cells (Swift, et al. (1984) Cell 38:639-46; Ornitz, et al. (1986) Cold Spring Harbor Symp. Quant. Biol. 50:399-409; MacDonald, (1987) Hepatology 7:425-515); insulin gene control region which is active in pancreatic beta cells (Hanahan, (1985) Nature 315:115-22), immunoglobulin gene control region which is active in lymphoid cells (Grosschedl, et al. (1984) Cell 38:647-58; Adames, et al. (1985) Nature 318:533-8; Alexander, et al. (1987) Mol. Cell. Biol. 7:1436-44), mouse mammary tumor virus control region which is active in testicular, breast, lymphoid and mast cells (Leder, et al. (1986) Cell 45:485-95), albumin gene control region which is active in liver (Pinkert, et al. (1987) Genes and Devel. 1:268-76), alpha-fetoprotein gene control region which is active in liver (Krumlauf, et al. (1985) Mol. Cell. Biol., 5:1639-48; Hammer, et al. (1987) Science 235:53-8), alpha 1-antitrypsin gene control region which is active in the liver (Kelsey, et al. (1987) Genes and Devel., 1: 161-71), beta-globin gene control region which is active in myeloid cells (Mogram, et al. (1985) Nature 315: 338-40; Kollias, et al. (1986) Cell 46:89-94), myelin basic protein gene control region which is active in oligodendrocyte cells in the brain (Readhead, et al. (1987) Cell 48:703-12), myosin light chain-2 gene control region which is active in skeletal muscle (Sani, (1985) Nature 314.283-6), and gonadotropic releasing hormone gene control region which is active in the hypothalamus (Mason, et al. (1986) Science 234:1372-8).

Other promoters which may be used in the practice of the invention include promoters which are preferentially activated in dividing cells, promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters.

The vectors may also include other elements, such as enhancers, repressor systems, and localization signals. A membrane localization signal is a preferred element when expressing a sequence encoding an intracellular binding protein, which functions by contacting the intracellular domain of the GPCR and is most effective when the vector product is directed to the inner surface of the cellular membrane, where its target resides. Membrane localization signals are well known to persons skilled in the art. For example, a membrane localization domain suitable for localizing a polypeptide to the plasma membrane is the C-terminal sequence CaaX for farnesylation (where "a" is an aliphatic amino acid residue, and "X" is any amino acid residue, generally leucine), for example, Cysteine-Alanine-Alanine-Leucine, or Cysteine-Isoleucine-Valine-Methionine. Other membrane localization signals include the putative membrane localization sequence from the C-terminus of Bcl-2 or the C-terminus of other members of the Bcl-2 family of proteins.

Additional vector systems include the non-viral systems that facilitate introduction of polynucleotide agents into a patient. For example, a DNA vector encoding a desired sequence can be introduced in vivo by lipofection. Synthetic cationic lipids designed to limit the difficulties encountered with liposome-mediated transfection can be used to prepare liposomes for in vivo transfection of a gene encoding a marker (Felgner, et. al. (1987) Proc. Natl. Acad. Sci. USA 84:7413-7); see Mackey, et al. (1988) Proc. Natl. Acad. Sci. USA 85:8027-31; Ulmer, et al. (1993) Science 259:1745-8). The use of cationic lipids may promote encapsulation of negatively charged nucleic acids, and also promote fusion with negatively charged cell membranes (Felgner and Ringold, (1989) Nature 337:387-8). Particularly useful lipid compounds and compositions for transfer of nucleic acids are described in International Patent Publications WO 95/18863 and WO 96/17823, and in U.S. Pat. No. 5,459,127. The use of lipofection to introduce exogenous genes into the specific organs in vivo has certain practical advantages and directing transfection to particular cell types would be particularly advantageous in a tissue with cellular heterogeneity, for example, pancreas, liver, kidney, and the brain. Lipids may be chemically coupled to other molecules for the purpose of targeting. Targeted peptides, e.g., hormones or neurotransmitters, and proteins for example, antibodies, or non-peptide molecules could be coupled to liposomes chemically. Other molecules are also useful for facilitating transfection of a nucleic acid in vivo, for example, a cationic oligopeptide (e.g., International Patent Publication WO 95/21931), peptides derived from DNA binding proteins (e.g., International Patent Publication WO 96/25508), or a cationic polymer (e.g., International Patent Publication WO 95/21931).

It is also possible to introduce a DNA vector in vivo as a naked DNA plasmid (see U.S. Pat. Nos. 5,693,622, 5,589,466 and 5,580,859). Naked DNA vectors for therapeutic purposes can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wilson, et al. (1992) J. Biol. Chem. 267:963-7; Wu and Wu, (1988) J. Biol. Chem. 263: 14621-4; Hartmut, et al. Canadian Patent Application No. 2,012,311, filed Mar. 15, 1990; Williams, et al (1991). Proc. Natl. Acad. Sci. USA 88:2726-30). Receptor-mediated DNA delivery approaches can also be used (Curiel, et al. (1992) Hum. Gene Ther. 3:147-54; Wu and Wu, (1987) J. Biol. Chem. 262:4429-32).

The present invention also provides biologically compatible compositions comprising the compounds identified as antagonists and/or inverse agonists of GPCR, and the expression-inhibiting agents as described hereinabove.

A biologically compatible composition is a composition, that may be solid, liquid, gel, or other form, in which the compound, polynucleotide, vector, and antibody of the invention is maintained in an active form, e.g., in a form able to effect a biological activity. For example, a compound of the invention would have inverse agonist or antagonist activity on the GPCR; a nucleic acid would be able to replicate, translate a message, or hybridize to a complementary mRNA of a GPCR; a vector would be able to transfect a target cell and expression the antisense, antibody, ribozyme or siRNA as described hereinabove; an antibody would bind a GPCR polypeptide domain.

A preferred biologically compatible composition is an aqueous solution that is buffered using, e.g., Tris, phosphate, or HEPES buffer, containing salt ions. Usually the concentration of salt ions will be similar to physiological levels. Biologically compatible solutions may include stabilizing agents and preservatives. In a more preferred embodiment, the biocompatible composition is a pharmaceutically acceptable composition. Such compositions can be formulated for administration by topical, oral, parenteral, intranasal, subcutaneous, and intraocular, routes. Parenteral administration is meant to include intravenous injection, intramuscular injection, intraarterial injection or infusion techniques. The composition may be administered parenterally in dosage unit formulations containing standard, well known non-toxic physiologically acceptable carriers, adjuvants and vehicles as desired.

A particularly preferred embodiment of the present composition invention is a cognitive-enhancing pharmaceutical composition comprising a therapeutically effective amount of an expression-inhibiting agent as described hereinabove, in admixture with a pharmaceutically acceptable carrier. Another preferred embodiment is a pharmaceutical composition for the treatment or prevention of a condition involving cognitive impairment or a susceptibility to the condition, comprising an effective amyloid beta peptide inhibiting amount of a GPCR antagonist or inverse agonist its pharmaceutically acceptable salts, hydrates, solvates, or prodrugs thereof in admixture with a pharmaceutically acceptable carrier. A particularly preferred class of such compositions comprise an aryloxydithiourea compound.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical compositions for oral use can be prepared by combining active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate. Dragee cores may be used in conjunction with suitable coatings, such as concentrated sugar solutions, which may also contain gum arabic, talc, polyvinyl-pyrrolidone, carbopol gel, polyethylene glycol, and/or titanium dioxide lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Preferred sterile injectable preparations can be a solution or suspension in a non-toxic parenterally acceptable solvent or diluent. Examples of pharmaceutically acceptable carriers are saline, buffered saline, isotonic saline (e.g. monosodium or disodium phosphate, sodium, potassium; calcium or magnesium chloride, or mixtures of such salts), Ringer's solution, dextrose, water, sterile water, glycerol, ethanol, and combinations thereof 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The composition medium can also be a hydrogel, which is prepared from any biocompatible or non-cytotoxic homo- or hetero-polymer, such as a hydrophilic polyacrylic acid polymer that can act as a drug absorbing sponge. Certain of them, such as, in particular, those obtained from ethylene and/or propylene oxide are commercially available. A hydrogel can be deposited directly onto the surface of the tissue to be treated, for example during surgical intervention.

Embodiments of pharmaceutical compositions of the present invention comprise a replication defective recombinant viral vector encoding the polynucleotide inhibitory agent of the present invention and a transfection enhancer, such as poloxamer. An example of a poloxamer is Poloxamer 407, which is commercially available (BASF, Parsippany, N.J.) and is a non-toxic, biocompatible polyol. A poloxamer impregnated with recombinant viruses may be deposited directly on the surface of the tissue to be treated, for example during a surgical intervention. Poloxamer possesses essentially the same advantages as hydrogel while having a lower viscosity.

The active expression-inhibiting agents may also be entrapped in microcapsules prepared, for example, by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1980) 16th edition, Osol, A. Ed.

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™. (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37.degree. C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

The present invention also provides methods of inhibiting the processing of amyloid-beta precursor protein in a subject suffering or susceptible to the abnormal processing of said protein, which comprise the administration to said subject a therapeutically effective amount of an expression-inhibiting agent of the invention. Another aspect of the present method invention is the treatment or prevention of a condition involving cognitive impairment or a susceptibility to the condition. A special embodiment of this invention is a method wherein the condition is Alzheimer's disease.

As defined above, therapeutically effective dose means that amount of protein, polynucleotide, peptide, or its antibodies, agonists or antagonists, which ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The pharmaceutical compositions according to this invention may be administered to a subject by a variety of methods. They may be added directly to target tissues, complexed with cationic lipids, packaged within liposomes, or delivered to target cells by other methods known in the art. Localized administration to the desired tissues may be done by catheter, infusion pump or stent. The DNA, DNA/vehicle complexes, or the recombinant virus particles are locally administered to the site of treatment. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery. Examples of ribozyme delivery and administration are provided in Sullivan et al. WO 94/02595.

Antibodies according to the invention may be delivered as a bolus only, infused over time or both administered as a bolus and infused over time. Those skilled in the art may employ different formulations for polynucleotides than for proteins. Similarly, delivery of polynucleotides or polypeptides will be specific to particular cells, conditions, locations, etc.

As discussed hereinabove, recombinant viruses may be used to introduce DNA encoding polynucleotide agents useful in the present invention. Recombinant viruses according to the invention are generally formulated and administered in the form of doses of between about $10^4$ and about $10^{14}$ pfu. In the case of AAVs and adenoviruses, doses of from about $10^6$ to about $10^{11}$ pfu are preferably used. The term pfu ("plaque-forming unit") corresponds to the infective power of a suspension of virions and is determined by infecting an appropriate cell culture and measuring the number of plaques formed. The techniques for determining the pfu titre of a viral solution are well documented in the prior art.

Still another aspect or the invention relates to a method for diagnosing a pathological condition involving cognitive impairment or a susceptibility to the condition in a subject, comprising determining the amount of polypeptide comprising an amino acid sequence selected from the group consisting of SEQ ID NO: 4-6 in a biological sample, and comparing the amount with the amount of the polypeptide in a healthy subject, wherein an increase of the amount of polypeptide compared to the healthy subject is indicative of the presence of the pathological condition.

EXPERIMENTAL SECTION

Example 1

GPR3 Increases Amyloid Beta 1-42 Levels

To identify novel drug targets that change the APP processing, a stable cell line over expressing APP is generated. This stable cell line is made by transfecting HEK293 cells with APP770wt cDNA cloned into pcDNA3.1, followed by selection with G418 for 3 weeks. At this time point colonies are picked and stable clones are expanded and tested for their secreted amyloid-beta peptide levels. One clone that secretes amyloid-beta at a high level, HEK293 APPwt, is selected for experiments to identify drug targets. This is accomplished by transducing HEK293 APPwt with adenoviral cDNA libraries and measuring changes to the resulting amyloid beta 1-42 levels via ELISA.

Cells seeded in collagen-coated plates at a cell density of 15000 cells/well (384 well plate) in DMEM (10% FBS), are infected 24 h later with 1 µl or 0.2 µl of adenovirus (corresponding to an average multiplicity of infection (MOI) of 120 and 24 respectively). The following day, the virus is washed away and DMEM (25 mM Hepes; 10% FBS) is added to the cells. Amyloid-beta peptides are allowed to accumulate during 24 h. The ELISA plate is prepared by coating with a capture antibody (JRF/cAbeta42/26) (obtained from M Mercken, Johnson and Johnson Pharmaceutical Research and Development, B-2340 Beerse, Belgium) overnight in buffer 42 (Table 1) at a concentration of 2.5 µg/ml. The excess capture antibody is washed away the next morning with PBS and the ELISA plate is then blocked overnight with casein buffer (see Table 1) at 4° C. Upon removal of the blocking buffer, 30 µl of the sample is transferred to the ELISA plate and incubated overnight at 4° C. After extensive washing with PBS-Tween20 and PBS, 30 µl of the horseradish peroxidase (HRP) labeled detection antibody (Peroxidase Labeling Kit, Roche), JRF/AbetaN/25-HRP (obtained from M Mercken, Johnson and Johnson Pharmaceutical Research and Development, B-2340 Beerse, Belgium) is diluted 1/5000 in buffer C (see Table 1) and added to the wells for another 2 h. Following the removal of excess detection antibody by a wash with PBS-Tween20 and PBS, HRP activity is detected via addition of luminol substrate (Roche), which is converted into a chemiluminescent signal by the HRP enzyme.

TABLE 1

| buffers and solutions used for ELISA | |
| --- | --- |
| Buffer 42 | 30 mM $NaHCO_3$, 70 mM $Na_2CO_3$, 0.05% $NaN_3$, pH 9.6 |
| Casein buffer | 0.1% casein in PBS 1× |

TABLE 1-continued buffers and solutions used for ELISA

| | |
|---|---|
| EC Buffer | 20 mM sodium phosphate, 2 mM EDTA, 400 mM NaCl, 0.2% BSA, 0.05% CHAPS, 0.4% casein, 0.05% NaN$_3$, pH 7 |
| Buffer C | 20 mM sodium phosphate, 2 mM EDTA, 400 mM NaCl, 1% BSA, pH 7 |
| PBS 10× | 80 g NaCl + 2 g KCl + 11.5 g Na$_2$HPO$_4$.7H$_2$O + 2 g KH$_2$PO$_4$ in 1 l milli Q, pH 7.4 |
| PBST | PBS 1× with 0.05% Tween 20 |

Figure 2:
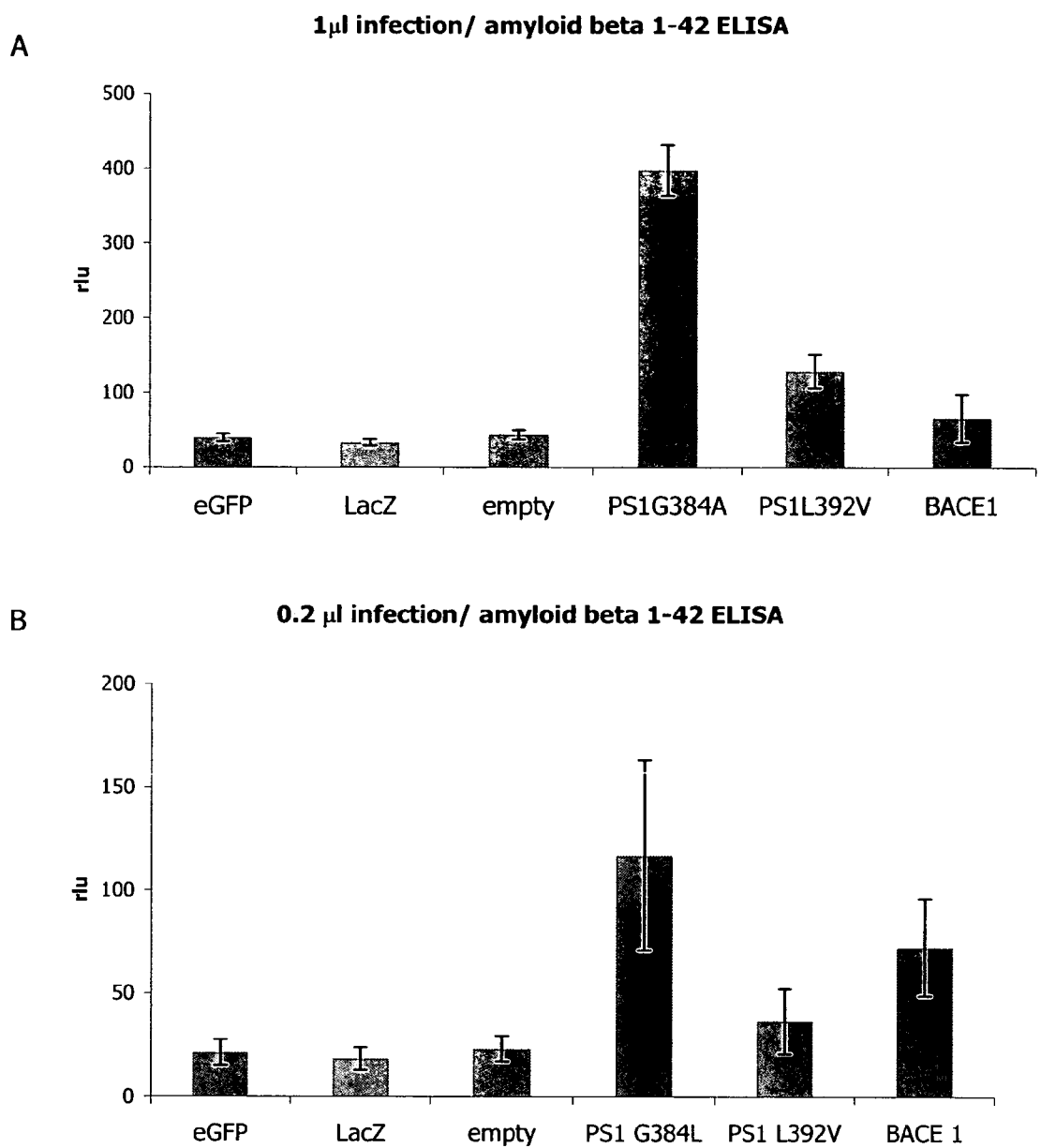
FIG. 2: Evaluation of the APP processing assay: Positive (PS1G384L; PS1L392V and BACE1) and negative (eGFP, LacZ and empty) control viruses are infected in Hek293APPwt at random MOI, mimicking a screening. A and B: Transduction is performed respectively with 1 and 0.2 µl of virus and amyloid beta 1-42 levels are performed. Data are represented as relative light units and correlate to pM of amyloid beta 1-42.

In order to validate the assay, the effect of adenoviral over expression with random titer of two clinical PS1 mutants and BACE on amyloid beta 1-42 production is evaluated in the HEK293 APPwt cells. As is shown in FIG. 2, all PS1 and BACE constructs induce amyloid beta 1-42 levels as expected.

An adenoviral GPCR cDNA library was constructed as follows. DNA fragments covering the full coding region of the GPCRs, are amplified by PCR from a pooled placental and fetal liver cDNA library (InvitroGen). All fragments are cloned into an adenoviral vector as described in U.S. Pat. No. 6,340,595, the contents of which are herein incorporated by reference, and subsequently adenoviruses are made harboring the corresponding cDNAs. During the screening of the adenoviral GPCR library in the HEK293 APPwt cells, over expression of GPR3 lead to increased levels of amyloid beta 1-42 peptides in the conditioned medium of HEK293 APPwt cells. These results indicate that GPR3 was identified as a modulator of APP processing.

The stimulatory effect of GPR3 is confirmed upon re-screening of the viruses with a known titer (viral particles/ml), as determined by quantitative real time PCR. GPR3 virus is infected at MOIs ranging from 2 to 250 and the experiment is performed as described above. Amyloid beta 1-42 levels are 2 fold higher compared to the negative controls for Ad5/GPR3 (FIG. 3A). In addition, the effect of GPR3 on amyloid beta 1-40, 11-42, 1-x and y-42 levels are checked under similar conditions as above (FIG. 3B-3E). The respective ELISAs are performed as described above, except that the following antibodies were used: for the amyloid beta 1-40 ELISA, the capture and detection antibody are respectively JRF/cAbeta40/10 and JRF/AbetaN/25-HRP (obtained from M Mercken, Johnson and Johnson Pharmaceutical Research and Development, B-2340 Beerse, Belgium), for the amyloid beta 11-42 ELISA, the capture and detection antibody are respectively JRF/cAbeta42/26 and JRF/hAb11/1 (obtained from M Mercken, Johnson and Johnson Pharmaceutical Research and Development, B-2340 Beerse, Belgium), for the amyloid beta y-42 ELISA (y ranges from 1-17), the capture and detection antibody are respectively JRF/cAbeta42/26 and 4G8-HRP (obtained respectively from M Mercken, Johnson and Johnson Pharmaceutical Research and Development, B-2340 Beerse, Belgium and from Signet, USA) while for the amyloid beta 1-x ELISA (x ranges from 24-42) the capture and detection antibodies are JRF/AbetaN/25 and 4G8-HRP, respectively (obtained respectively from M Mercken, Johnson and Johnson Pharmaceutical Research and Development, B-2340 Beerse, Belgium and from Signet, USA). The amyloid beta 1-x ELISA is used for the detection of amyloid peptides with a variable C-terminus (amyloid beta 1-37; 1-38; 1-39; 1-40; 1-42). The results of these experiments clearly show an increase of amyloid beta 1-40, 11-42, y-42 and 1-x species upon transduction of GPR3 (FIG. 3B-3E). The same procedure is used for the analysis of APP processing by GPR6 and GPR12.

Example 2

Identification of Homologues of GPR3

The amino acid sequence of the human GPR3 receptor was used as query in a BLAST search against all the human GPCRs in order to find its closest homologues. Table 2 (SEQ ID NO: 5-6) shows the 2 closest homologues of the GPR3 receptor. Using ClustalW an alignment was constructed showing the degree of homology between the GPR3 and its closest homologues, the GPR6 and GPR12 (FIG. 5).

TABLE 2

GPCRs involved in APP processing (SEQ ID NO: 1-3; 4-6), Sequences for expression-inhibiting agent (SEQ ID NO: 7-287), the hairpin loop sequence of the RNAi (SEQ ID NO: 288), and the domains of GPR3, GPR6, and GPR 12 (SEQ ID NO: 289-333):

| SEQ ID NO | Galapagos ID | Accession | Sequence | | Type |
|---|---|---|---|---|---|
| 1 | 1772 | NM_005281 | | GPR3 | DNA |
| 2 | 1780 | NM_005284 | | GPR6 | DNA |
| 3 | 1763 | NM_005288 | | GPR12 | DNA |
| 4 | 1772 | NP_005272 | | GPR3 | Protein |
| 5 | 1780 | NP_005275 | | GPR6 | Protein |
| 6 | 1763 | NP_005279 | | GPR12 | Protein |
| 7 | NM_005281_idx127 | NM_005281 | TGGGATGTGGTGCTCTGCATC | GPR3 | DNA |
| 8 | NM_005281_idx129 | NM_005281 | GGATGTGGTGCTCTGCATCTC | GPR3 | DNA |
| 9 | NM_005281_idx172 | NM_005281 | AATGCGCTAGTGGTGGCCATC | GPR3 | DNA |
| 10 | NM_005281_idx280 | NM_005281 | GTCCTGCACTTTGCTGCTGTC | GPR3 | DNA |

TABLE 2-continued

GPCRs involved in APP processing (SEQ ID NO: 1-3; 4-6), Sequences for expression-inhibiting agent (SEQ ID NO: 7-287), the hairpin loop sequence of the RNAi (SEQ ID NO: 288), and the domains of GPR3, GPR6, and GPR 12 (SEQ ID NO: 289-333):

| SEQ ID NO | Galapagos ID | Accession | Sequence | | Type |
|---|---|---|---|---|---|
| 11 | NM_005281_idx283 | NM_005281 | CTGCACTTTGCTGCTGTCTTC | GPR3 | DNA |
| 12 | NM_005281_idx286 | NM_005281 | CACTTTGCTGCTGTCTTCTGC | GPR3 | DNA |
| 13 | NM_005281_idx289 | NM_005281 | TTTGCTGCTGTCTTCTGCATC | GPR3 | DNA |
| 14 | NM_005281_idx294 | NM_005281 | TGCTGTCTTCTGCATCGGCTC | GPR3 | DNA |
| 15 | NM_005281_idx297 | NM_005281 | TGTCTTCTGCATCGGCTCAGC | GPR3 | DNA |
| 16 | NM_005281_idx342 | NM_005281 | CGTGCTGGCAATGGCCTTTAC | GPR3 | DNA |
| 17 | NM_005281_idx343 | NM_005281 | GTGCTGGCAATGGCCTTTACC | GPR3 | DNA |
| 18 | NM_005281_idx352 | NM_005281 | ATGGCCTTTACCGCCAGCATC | GPR3 | DNA |
| 19 | NM_005281_idx370 | NM_005281 | ATCGGCAGTCTACTGGCCATC | GPR3 | DNA |
| 20 | NM_005281_idx376 | NM_005281 | AGTCTACTGGCCATCACTGTC | GPR3 | DNA |
| 21 | NM_005281_idx379 | NM_005281 | CTACTGGCCATCACTGTCGAC | GPR3 | DNA |
| 22 | NM_005281_idx380 | NM_005281 | TACTGGCCATCACTGTCGACC | GPR3 | DNA |
| 23 | NM_005281_idx390 | NM_005281 | CACTGTCGACCGCTACCTTTC | GPR3 | DNA |
| 24 | NM_005281_idx392 | NM_005281 | CTGTCGACCGCTACCTTTCTC | GPR3 | DNA |
| 25 | NM_005281_idx397 | NM_005281 | GACCGCTACCTTTCTCTGTAC | GPR3 | DNA |
| 26 | NM_005281_idx402 | NM_005281 | CTACCTTTCTCTGTACAATGC | GPR3 | DNA |
| 27 | NM_005281_idx403 | NM_005281 | TACCTTTCTCTGTACAATGCC | GPR3 | DNA |
| 28 | NM_005281_idx404 | NM_005281 | ACCTTTCTCTGTACAATGCCC | GPR3 | DNA |
| 29 | NM_005281_idx406 | NM_005281 | CTTTCTCTGTACAATGCCCTC | GPR3 | DNA |
| 30 | NM_005281_idx408 | NM_005281 | TTCTCTGTACAATGCCCTCAC | GPR3 | DNA |
| 31 | NM_005281_idx409 | NM_005281 | TCTCTGTACAATGCCCTCACC | GPR3 | DNA |
| 32 | NM_005281_idx412 | NM_005281 | CTGTACAATGCCCTCACCTAC | GPR3 | DNA |
| 33 | NM_005281_idx417 | NM_005281 | CAATGCCCTCACCTACTATTC | GPR3 | DNA |
| 34 | NM_005281_idx423 | NM_005281 | CCTCACCTACTATTCAGAGAC | GPR3 | DNA |
| 35 | NM_005281_idx426 | NM_005281 | CACCTACTATTCAGAGACAAC | GPR3 | DNA |
| 36 | NM_005281_idx432 | NM_005281 | CTATTCAGAGACAACAGTGAC | GPR3 | DNA |
| 37 | NM_005281_idx434 | NM_005281 | ATTCAGAGACAACAGTGACAC | GPR3 | DNA |
| 38 | NM_005281_idx438 | NM_005281 | AGAGACAACAGTGACACGGAC | GPR3 | DNA |
| 39 | NM_005281_idx439 | NM_005281 | GAGACAACAGTGACACGGACC | GPR3 | DNA |
| 40 | NM_005281_idx449 | NM_005281 | TGACACGGACCTATGTGATGC | GPR3 | DNA |
| 41 | NM_005281_idx453 | NM_005281 | ACGGACCTATGTGATGCTGGC | GPR3 | DNA |
| 42 | NM_005281_idx545 | NM_005281 | CCACATGTGGCGTGGTTTATC | GPR3 | DNA |
| 43 | NM_005281_idx546 | NM_005281 | CACATGTGGCGTGGTTTATCC | GPR3 | DNA |
| 44 | NM_005281_idx548 | NM_005281 | CATGTGGCGTGGTTTATCCAC | GPR3 | DNA |
| 45 | NM_005281_idx550 | NM_005281 | TGTGGCGTGGTTTATCCACTC | GPR3 | DNA |

TABLE 2-continued

GPCRs involved in APP processing (SEQ ID NO: 1-3; 4-6), Sequences for expression-inhibiting agent (SEQ ID NO: 7-287), the hairpin loop sequence of the RNAi (SEQ ID NO: 288), and the domains of GPR3, GPR6, and GPR 12 (SEQ ID NO: 289-333):

| SEQ ID NO | Galapagos ID | Accession | Sequence | | Type |
|---|---|---|---|---|---|
| 46 | NM_005281_idx552 | NM_005281 | TGGCGTGGTTTATCCACTCTC | GPR3 | DNA |
| 47 | NM_005281_idx553 | NM_005281 | GGCGTGGTTTATCCACTCTCC | GPR3 | DNA |
| 48 | NM_005281_idx559 | NM_005281 | GTTTATCCACTCTCCAAGAAC | GPR3 | DNA |
| 49 | NM_005281_idx560 | NM_005281 | TTTATCCACTCTCCAAGAACC | GPR3 | DNA |
| 50 | NM_005281_idx563 | NM_005281 | ATCCACTCTCCAAGAACCATC | GPR3 | DNA |
| 51 | NM_005281_idx572 | NM_005281 | CCAAGAACCATCTGGTAGTTC | GPR3 | DNA |
| 52 | NM_005281_idx576 | NM_005281 | GAACCATCTGGTAGTTCTGGC | GPR3 | DNA |
| 53 | NM_005281_idx577 | NM_005281 | AACCATCTGGTAGTTCTGGCC | GPR3 | DNA |
| 54 | NM_005281_idx582 | NM_005281 | TCTGGTAGTTCTGGCCATTGC | GPR3 | DNA |
| 55 | NM_005281_idx583 | NM_005281 | CTGGTAGTTCTGGCCATTGCC | GPR3 | DNA |
| 56 | NM_005281_idx586 | NM_005281 | GTAGTTCTGGCCATTGCCTTC | GPR3 | DNA |
| 57 | NM_005281_idx589 | NM_005281 | GTTCTGGCCATTGCCTTCTTC | GPR3 | DNA |
| 58 | NM_008154_idx1099 | NM_005281 | GCCTTCTTCATGGTGTTTGGC | GPR3 | DNA |
| 59 | NM_005281_idx604 | NM_005281 | TTCTTCATGGTGTTTGGCATC | GPR3 | DNA |
| 60 | NM_005281_idx608 | NM_005281 | TCATGGTGTTTGGCATCATGC | GPR3 | DNA |
| 61 | NM_005281_idx611 | NM_005281 | TGGTGTTTGGCATCATGCTGC | GPR3 | DNA |
| 62 | NM_005281_idx614 | NM_005281 | TGTTTGGCATCATGCTGCAGC | GPR3 | DNA |
| 63 | NM_005281_idx616 | NM_005281 | TTTGGCATCATGCTGCAGCTC | GPR3 | DNA |
| 64 | NM_005281_idx619 | NM_005281 | GGCATCATGCTGCAGCTCTAC | GPR3 | DNA |
| 65 | NM_005281_idx621 | NM_005281 | CATCATGCTGCAGCTCTACGC | GPR3 | DNA |
| 66 | NM_005281_idx622 | NM_005281 | ATCATGCTGCAGCTCTACGCC | GPR3 | DNA |
| 67 | NM_005281_idx628 | NM_005281 | CTGCAGCTCTACGCCCAAATC | GPR3 | DNA |
| 68 | NM_005281_idx631 | NM_005281 | CAGCTCTACGCCCAAATCTGC | GPR3 | DNA |
| 69 | NM_005281_idx632 | NM_005281 | AGCTCTACGCCCAAATCTGCC | GPR3 | DNA |
| 70 | NM_005281_idx637 | NM_005281 | TACGCCCAAATCTGCCGCATC | GPR3 | DNA |
| 71 | NM_005281_idx643 | NM_005281 | CAAATCTGCCGCATCGTCTGC | GPR3 | DNA |
| 72 | NM_005281_idx644 | NM_005281 | AAATCTGCCGCATCGTCTGCC | GPR3 | DNA |
| 73 | NM_005281_idx668 | NM_005281 | ATGCCCAGCAGATTGCCCTTC | GPR3 | DNA |
| 74 | NM_005281_idx775 | NM_005281 | TGCTGGTTGCCCTTCACTGTC | GPR3 | DNA |
| 75 | NM_005281_idx778 | NM_005281 | TGGTTGCCCTTCACTGTCTAC | GPR3 | DNA |
| 76 | NM_005281_idx781 | NM_005281 | TTGCCCTTCACTGTCTACTGC | GPR3 | DNA |
| 77 | NM_005281_idx782 | NM_005281 | TGCCCTTCACTGTCTACTGCC | GPR3 | DNA |
| 78 | NM_005281_idx785 | NM_005281 | CGTTCACTGTCTACTGCCTGC | GPR3 | DNA |
| 79 | NM_005281_idx816 | NM_005281 | CCACTCTCCACCTCTCTACAC | GPR3 | DNA |
| 80 | NM_005281_idx817 | NM_005281 | CACTCTCCACCTCTCTACACC | GPR3 | DNA |

TABLE 2-continued

GPCRs involved in APP processing (SEQ ID NO: 1-3; 4-6), Sequences for expression-inhibiting agent (SEQ ID NO: 7-287), the hairpin loop sequence of the RNAi (SEQ ID NO: 288), and the domains of GPR3, GPR6, and GPR 12 (SEQ ID NO: 289-333):

| SEQ ID NO | Galapagos ID | Accession | Sequence | | Type |
|---|---|---|---|---|---|
| 81 | NM_005281_idx821 | NM_005281 | CTCCACCTCTCTACACCTATC | GPR3 | DNA |
| 82 | NM_005281_idx825 | NM_005281 | ACCTCTCTACACCTATCTTAC | GPR3 | DNA |
| 83 | NM_005281_idx826 | NM_005281 | CCTCTCTACACCTATCTTACC | GPR3 | DNA |
| 84 | NM_005281_idx830 | NM_005281 | TCTACACCTATGTTACCTTGC | GPR3 | DNA |
| 85 | NM_005281_idx832 | NM_005281 | TACACCTATCTTACCTTGCTC | GPR3 | DNA |
| 86 | NM_005281_idx833 | NM_005281 | ACACCTATCTTACCTTGCTCC | GPR3 | DNA |
| 87 | NM_005281_1dx834 | NM_005281 | CACCTATCTTACCTTGCTCCC | GPR3 | DNA |
| 88 | NM_005281_idx837 | NM_005281 | CTATCTTACCTTGCTCCCTGC | GPR3 | DNA |
| 89 | NM_005281_idx838 | NM_005281 | TATCTTACCTTGCTCCCTGCC | GPR3 | DNA |
| 90 | NM_005281_idx840 | NM_005281 | TCTTACCTTGCTCCCTGCCAC | GPR3 | DNA |
| 91 | NM_005281_idx847 | NM_005281 | TTGCTCCCTGCCACCTACAAC | GPR3 | DNA |
| 92 | NM_008154_idx1354 | NM_005281 | GCCACCTACAACTCCATGATC | GPR3 | DNA |
| 93 | NM_005281_idx859 | NM_005281 | ACCTACAACTCCATGATCAAC | GPR3 | DNA |
| 94 | NM_008154_idx1358 | NM_005281 | CCTACAACTCCATGATCAACC | GPR3 | DNA |
| 95 | NM_005281_idx861 | NM_005281 | CTACAACTCCATGATCAACCC | GPR3 | DNA |
| 96 | NM_005281_1dx865 | NM_005281 | AACTCCATGATCAACCCTATC | GPR3 | DNA |
| 97 | NM_005281_idx868 | NM_005281 | TCCATGATCAACCCTATCATC | GPR3 | DNA |
| 98 | NM_005281_idx873 | NM_005281 | GATCAACCCTATCATCTACGC | GPR3 | DNA |
| 99 | NM_005281_idx874 | NM_005281 | ATCAACCCTATCATCTACGCC | GPR3 | DNA |
| 100 | NM_005281_idx877 | NM_005281 | AACCGTATCATCTACGCCTTC | GPR3 | DNA |
| 101 | NM_005281_idx878 | NM_005281 | ACCCTATCATCTACGCCTTCC | GPR3 | DNA |
| 102 | NM_005281_idx880 | NM_005281 | CCTATCATCTACGCCTTCCGC | GPR3 | DNA |
| 103 | NM_005281_idx883 | NM_005281 | ATCATCTACGCCTTCCGCAAC | GPR3 | DNA |
| 104 | NM_005281_idx884 | NM_005281 | TCATCTACGCCTTCCGCAACC | GPR3 | DNA |
| 105 | NM_005281_idx902 | NM_005281 | ACCAGGATGTGCAGAAAGTGC | GPR3 | DNA |
| 106 | NM_005281_idx909 | NM_005281 | TGTGCAGAAAGTGCTGTGGGC | GPR3 | DNA |
| 107 | NM_005281_idx916 | NM_005281 | AAAGTGCTGTGGGCTGTCTGC | GPR3 | DNA |
| 108 | NM_005281_idx941 | NM_005281 | GCTGTTCCTCTTCCAAGATCC | GPR3 | DNA |
| 109 | NM_005284_idx146 | NM_005284 | GAGCTAATGGGTCTCTGGAGC | GPR6 | DNA |
| 110 | NM_005284_idx150 | NM_005284 | TAATGGGTCTCTGGAGCTGTC | GPR6 | DNA |
| 111 | NM_005284_idx151 | NM_005284 | AATGGGTCTCTGGAGCTGTCC | GPR6 | DNA |
| 112 | NM_005284_idx319 | NM_005284 | ATGTTCGTGCTGGTAGGCAGC | GPR6 | DNA |
| 113 | NM_005284_idx373 | NM_005284 | CTCATCTTGCACTTTGTGTTC | GPR6 | DNA |
| 114 | NM_005284_idx374 | NM_005284 | TCATGTTGCACTTTGTGTTCC | GPR6 | DNA |
| 115 | NM_005284_idx379 | NM_005284 | TTGCACTTTGTGTTCCAGTAC | GPR6 | DNA |

TABLE 2-continued

GPCRs involved in APP processing (SEQ ID NO: 1-3; 4-6), Sequences for expression-inhibiting agent (SEQ ID NO: 7-287), the hairpin loop sequence of the RNAi (SEQ ID NO: 288), and the domains of GPR3, GPR6, and GPR 12 (SEQ ID NO: 289-333):

| SEQ ID NO | Galapagos ID | Accession | Sequence | | Type |
|---|---|---|---|---|---|
| 116 | NM_005284_idx386 | NM_005284 | TTGTGTTCCAGTACTTGGTGC | GPR6 | DNA |
| 117 | NM_005284_idx387 | NM_005284 | TGTGTTCCAGTACTTGGTGCC | GPR6 | DNA |
| 118 | NM_005284_idx388 | NM_005284 | GTGTTCCAGTACTTGGTGCCC | GPR6 | DNA |
| 119 | NM_005284_idx390 | NM_005284 | GTTCCAGTACTTGGTGCCCTC | GPR6 | DNA |
| 120 | NM_005284_idx409 | NM_005284 | TCGGAGACTGTGAGTCTGCTC | GPR6 | DNA |
| 121 | NM_005284_idx411 | NM_005284 | GGAGACTGTGAGTCTGCTCAC | GPR6 | DNA |
| 122 | NM_005284_idx496 | NM_005284 | CGCTACCTGTCCCTGTATAAC | GPR6 | DNA |
| 123 | NM_005284_idx498 | NM_005284 | CTACCTGTCCCTGTATAACGC | GPR6 | DNA |
| 124 | NM_005284_idx500 | NM_005284 | ACCTGTCCCTGTATAACGCGC | GPR6 | DNA |
| 125 | NM_005284_idx502 | NM_005284 | CTGTCCCTGTATAACGCGCTC | GPR6 | DNA |
| 126 | NM_005284_idx504 | NM_005284 | GTCCCTGTATAACGCGCTCAC | GPR6 | DNA |
| 127 | NM_005284_idx505 | NM_005284 | TCCCTGTATAACGCGCTCACC | GPR6 | DNA |
| 128 | NM_005284_idx511 | NM_005284 | TATAACGCGCTCACCTATTAC | GPR6 | DNA |
| 129 | NM_005284_idx513 | NM_005284 | TAACGCGCTCACCTATTACTC | GPR6 | DNA |
| 130 | NM_005284_idx515 | NM_005284 | ACGCGCTCACCTATTACTCGC | GPR6 | DNA |
| 131 | NM_005284_idx694 | NM_005284 | GCCGCCTTCTTCATGGTCTTC | GPR6 | DNA |
| 132 | NM_005284_idx697 | NM_005284 | GCCTTCTTCATGGTCTTCGGC | GPR6 | DNA |
| 133 | NM_005284_idx700 | NM_005284 | TTCTTCATGGTCTTCGGCATC | GPR6 | DNA |
| 134 | NM_005284_idx704 | NM_005284 | TCATGGTCTTCGGCATCATGC | GPR6 | DNA |
| 135 | NM_005284_idx707 | NM_005284 | TGGTCTTCGGCATCATGCTGC | GPR6 | DNA |
| 136 | NM_005284_idx709 | NM_005284 | GTCTTCGGCATCATGCTGCAC | GPR6 | DNA |
| 137 | NM_005284_idx710 | NM_005284 | TCTTCGGCATCATGCTGCACC | GPR6 | DNA |
| 138 | NM_005284_idx715 | NM_005284 | GGCATCATGCTGCACCTGTAC | GPR6 | DNA |
| 139 | NM_005284_idx719 | NM_005284 | TCATGCTGCACCTGTACGTGC | GPR6 | DNA |
| 140 | NM_005284_idx819 | NM_005284 | CACCAGAAAGGGTGTGGGTAC | GPR6 | DNA |
| 141 | NM_005284_idx821 | NM_005284 | CCAGAAAGGGTGTGGGTACAC | GPR6 | DNA |
| 142 | NM_005284_idx825 | NM_005284 | AAAGGGTGTGGGTACACTGGC | GPR6 | DNA |
| 143 | NM_005284_idx877 | NM_005284 | CTGCCCTTCGCCATCTATTGC | GPR6 | DNA |
| 144 | NM_005284_idx889 | NM_005284 | ATCTATTGCGTGGTGGGCAGC | GPR6 | DNA |
| 145 | NM_005284_idx926 | NM_005284 | TCTACACTTACGCCACCCTGC | GPR6 | DNA |
| 146 | NM_005284_idx956 | NM_005284 | CCTACAACTCCATGATCAATC | GPR6 | DNA |
| 147 | NM_005284_idx957 | NM_005284 | CTACAACTCCATGATCAATCC | GPR6 | DNA |
| 148 | NM_005284_idx958 | NM_005284 | TACAACTCCATGATCAATCCC | GPR6 | DNA |
| 149 | NM_005284_idx961 | NM_005284 | AACTCCATGATCAATCCCATC | GPR6 | DNA |
| 150 | NM_005284_idx964 | NM_005284 | TCCATGATCAATCCCATCATC | GPR6 | DNA |

TABLE 2-continued

GPCRs involved in APP processing (SEQ ID NO: 1-3; 4-6), Sequences for expression-inhibiting agent (SEQ ID NO: 7-287), the hairpin loop sequence of the RNAi (SEQ ID NO: 288), and the domains of GPR3, GPR6, and GPR 12 (SEQ ID NO: 289-333):

| SEQ ID NO | Galapagos ID | Accession | Sequence | | Type |
|---|---|---|---|---|---|
| 151 | NM_005284_idx969 | NM_005284 | GATCAATCCCATCATCTATGC | GPR6 | DNA |
| 152 | NM_005284_idx970 | NM_005284 | ATCAATCCCATCATCTATGCC | GPR6 | DNA |
| 153 | NM_000647_idx981 | NM_005284 | AATCCCATCATCTATGCCTTC | GPR6 | DNA |
| 154 | NM_005284_idx974 | NM_005284 | ATCCCATCATCTATGCCTTCC | GPR6 | DNA |
| 155 | NM_005284_idx976 | NM_005284 | CCCATCATCTATGCCTTCCGC | GPR6 | DNA |
| 156 | NM_005284_idx979 | NM_005284 | ATCATCTATGCCTTCCGCAAC | GPR6 | DNA |
| 157 | NM_005284_idx980 | NM_005284 | TCATCTATGCCTTCCGCAACC | GPR6 | DNA |
| 158 | NM_005284_idx1024 | NM_005284 | CTCCTGCTCTGTGGCTGTTTC | GPR6 | DNA |
| 159 | NM_005284_idx1025 | NM_005284 | TCCTGCTCTGTGGCTG17TCC | GPR6 | DNA |
| 160 | NM_005284_idx1029 | NM_005284 | GCTCTGTGGCTGTTTCCAGTC | GPR6 | DNA |
| 161 | NM_005284_idx1030 | NM_005284 | CTCTGTGGCTGTTTCCAGTCC | GPR6 | DNA |
| 162 | NM_005284_idx1037 | NM_005284 | GCTGTTTCCAGTCCAAAGTGC | GPR6 | DNA |
| 163 | NM_005284_idx1038 | NM_005284 | CTGTTTCCAGTCCAAAGTGCC | GPR6 | DNA |
| 164 | NM_005284_idx1039 | NM_005284 | TGTTTCCAGTCCAAAGTGCCC | GPR6 | DNA |
| 165 | NM_005284_idx1043 | NM_005284 | TCCAGTCCAAAGTGCCCTTTC | GPR6 | DNA |
| 166 | NM_005284_idx1047 | NM_005284 | GTCCAAAGTGCCCTTTCGTTC | GPR6 | DNA |
| 167 | NM_005284_idx1048 | NM_005284 | TCCAAAGTGCCCTTUCGTTCC | GPR6 | DNA |
| 168 | NM_005284_idx1053 | NM_005284 | AGTGCCCTTTCGTTCCAGGTC | GPR6 | DNA |
| 169 | NM_005284_idx1055 | NM_005284 | TGCCCTTTCGTTCCAGGTCTC | GPR6 | DNA |
| 170 | NM_005284_idx1060 | NM_005284 | TTTCGTTCCAGGTCTCCCAGC | GPR6 | DNA |
| 171 | NM_005288_idx115 | NM_005288 | GAGCCTGAGCTCGTAGTCAAC | GPR12 | DNA |
| 172 | NM_005288_idx116 | NM_005288 | AGCCTGAGCTCGTAGTCAACC | GPR12 | DNA |
| 173 | NM_005288_idx138 | NM_005288 | CTGGGACATTGTCTTGTGTAC | GPR12 | DNA |
| 174 | NM_005288_idx139 | NM_005288 | TGGGACATTGTCTTGTGTACC | GPR12 | DNA |
| 175 | NM_005288_idx141 | NM_005288 | GGACATTGTCTTGTGTACCTC | GPR12 | DNA |
| 176 | NM_005288_idx147 | NM_005288 | TGTCTTGTGTACCTCGGGAAC | GPR12 | DNA |
| 177 | NM_005288_idx148 | NM_005288 | GTCTTGTGTACCTCGGGAACC | GPR12 | DNA |
| 178 | NM_005288_idx149 | NM_005288 | TCTTGTGTACCTCGGGAACCC | GPR12 | DNA |
| 179 | NM_005288_idx151 | NM_005288 | TTGTGTACCTCGGGAACCCTC | GPR12 | DNA |
| 180 | NM_005288_idx154 | NM_005288 | TGTACCTCGGGAACCCTCATC | GPR12 | DNA |
| 181 | NM_005288_idx156 | NM_005288 | TACCTCGGGAACCCTCATCTC | GPR12 | DNA |
| 182 | NM_005288_idx184 | NM_005288 | AATGCCATTGTGGTCCTTATC | GPR12 | DNA |
| 183 | NM_005288_idx187 | NM_005288 | GCCATTGTGGTCCTTATCATC | GPR12 | DNA |
| 184 | NM_005288_idx191 | NM_005288 | TTGTGGTCCTTATCATCTTCC | GPR12 | DNA |
| 185 | NM_005288_idx193 | NM_005288 | GTGGTCCTTATCATCTTCCAC | GPR12 | DNA |

TABLE 2-continued

GPCRs involved in APP processing (SEQ ID NO: 1-3; 4-6), Sequences for expression-inhibiting agent (SEQ ID NO: 7-287), the hairpin loop sequence of the RNAi (SEQ ID NO: 288), and the domains of GPR3, GPR6, and GPR 12 (SEQ ID NO: 289-333):

| SEQ ID NO | Galapagos ID | Accession | Sequence | Type |
|---|---|---|---|---|
| 186 | NM_005288_idx196 | NM_005288 | GTCCTTATCATCTTCCACAAC GPR12 | DNA |
| 187 | NM_005288_idx197 | NM_005288 | TCCTTATCATCTTCCACAACC GPR12 | DNA |
| 188 | NM_005288_idx198 | NM_005288 | CCTTATCATCTTCCACAACCC GPR12 | DNA |
| 189 | NM_005288_idx232 | NM_005288 | CCCATGTTCCTGCTAATAGGC GPR12 | DNA |
| 190 | NM_005288_idx235 | NM_005288 | ATGTTCCTGCTAATAGGCAGC GPR12 | DNA |
| 191 | NM_005288_idx236 | NM_005288 | TGTTCCTGCTAATAGGCAGCC GPR12 | DNA |
| 192 | NM_005288_idx242 | NM_005288 | TGCTAATAGGCAGCCTGGCTC GPR12 | DNA |
| 193 | NM_005288_idx246 | NM_005288 | AATAGGCAGCCTGGCTCTTGC GPR12 | DNA |
| 194 | NM_005288_idx312 | NM_005288 | CTACCTGCTTCAGTCAGAAGC GPR12 | DNA |
| 195 | NM_005288_idx313 | NM_005288 | TACCTGCTTCAGTCAGAAGCC GPR12 | DNA |
| 196 | NM_005288_idx315 | NM_005288 | CCTGCTTCAGTCAGAAGCCAC GPR12 | DNA |
| 197 | NM_005288_idx316 | NM_005288 | CTGCTTCAGTCAGAAGCCACC GPR12 | DNA |
| 198 | NM_005288_idx320 | NM_005288 | TTCAGTCAGAAGCCACCAAGC GPR12 | DNA |
| 199 | NM_005288_idx325 | NM_005288 | TCAGAAGCCACCAAGCTGGTC GPR12 | DNA |
| 200 | NM_005288_idx327 | NM_005288 | AGAAGCCACCAAGCTGGTCAC GPR12 | DNA |
| 201 | NM_005288_idx343 | NM_005288 | GTCACGATCGGCCTCATTGTC GPR12 | DNA |
| 202 | NM_005288_idx352 | NM_005288 | GGCCTCATTGTCGCCTCTTTC GPR12 | DNA |
| 203 | NM_005288_idx354 | NM_005288 | CCTCATTGTCGCCTCTTTCTC GPR12 | DNA |
| 204 | NM_005288_idx357 | NM_005288 | CATTGTCGCCTCTTTCTCTGC GPR12 | DNA |
| 205 | NM_005288_idx358 | NM_005288 | ATTGTCGCCTCTTTCTCTGCC GPR12 | DNA |
| 206 | NM_005288_idx360 | NM_005288 | TGTCGCCTCTTTCTCTGCCTC GPR12 | DNA |
| 207 | NM_005288_idx364 | NM_005288 | GCCTCTTTCTCTGCCTCTGTC GPR12 | DNA |
| 208 | NM_005288_idx367 | NM_005288 | TCTTTCTCTGCCTCTGTCTGC GPR12 | DNA |
| 209 | NM_005288_idx370 | NM_005288 | TTCTCTGCCTCTGTCTGCAGC GPR12 | DNA |
| 210 | NM_005288_idx382 | NM_005288 | GTCTGCAGCTTGCTGGCTATC GPR12 | DNA |
| 211 | NM_005288_idx384 | NM_005288 | CTGCAGCTTGCTGGCTATCAC GPR12 | DNA |
| 212 | NM_005288_idx391 | NM_005288 | TTGCTGGCTATCACTGTTGAC GPR12 | DNA |
| 213 | NM_005288_idx392 | NM_005288 | TGCTGGCTATCACTGTTGACC GPR12 | DNA |
| 214 | NM_005288_idx394 | NM_005288 | CTGGCTATCACTGTTGACCGC GPR12 | DNA |
| 215 | NM_005288_idx397 | NM_005288 | GCTATCACTGTTGACCGCTAC GPR12 | DNA |
| 216 | NM_005288_idx398 | NM_005288 | CTATCACTGTTGACCGCTACC GPR12 | DNA |
| 217 | NM_005288_idx400 | NM_005288 | ATCACTGTTGACCGCTACCTC GPR12 | DNA |
| 218 | NM_005288_idx402 | NM_005288 | CACTGTTGACCGCTACCTCTC GPR12 | DNA |
| 219 | NM_005288_idx404 | NM_005288 | CTGTTGACCGCTACCTCTCAC GPR12 | DNA |
| 220 | NM_005288_idx409 | NM_005288 | GACCGCTACCTCTCACTGTAC GPR12 | DNA |

TABLE 2-continued

GPCRs involved in APP processing (SEQ ID NO: 1-3; 4-6), Sequences for expression-inhibiting agent (SEQ ID NO: 7-287), the hairpin loop sequence of the RNAi (SEQ ID NO: 288), and the domains of GPR3, GPR6, and GPR 12 (SEQ ID NO: 289-333):

| SEQ ID NO | Galapagos ID | Accession | Sequence | | Type |
|---|---|---|---|---|---|
| 221 | NM_005288_idx412 | NM_005288 | CGCTACCTCTCACTGTACTAC | GPR12 | DNA |
| 222 | NM_005288_idx414 | NM_005288 | CTACCTCTCACTGTACTACGC | GPR12 | DNA |
| 223 | NM_005288_idx416 | NM_005288 | ACCTCTCACTGTACTACGCTC | GPR12 | DNA |
| 224 | NM_005288_idx420 | NM_005288 | CTCACTGTACTACGCTCTGAC | GPR12 | DNA |
| 225 | NM_005288_idx424 | NM_005288 | CTGTACTACGCTCTGACGTAC | GPR12 | DNA |
| 226 | NM_005288_idx425 | NM_005288 | TGTACTACGCTCTGACGTACC | GPR12 | DNA |
| 227 | NM_005288_idx429 | NM_005288 | CTACGCTCTGACGTACCATTC | GPR12 | DNA |
| 228 | NM_005288_idx438 | NM_005288 | GACGTACCATTCGGAGAGGAC | GPR12 | DNA |
| 229 | NM_005288_idx442 | NM_005288 | TACCATTCGGAGAGGACGGTG | GPR12 | DNA |
| 230 | NM_005288_idx450 | NM_005288 | GGAGAGGACGGTCACGTTTAC | GPR12 | DNA |
| 231 | NM_005288_idx451 | NM_005288 | GAGAGGACGGTCACGTTTACC | GPR12 | DNA |
| 232 | NM_005288_idx457 | NM_005288 | ACGGTCACGTTTACCTATGTC | GPR12 | DNA |
| 233 | NM_005288_idx461 | NM_005288 | TCACGTTTACCTATGTCATGC | GPR12 | DNA |
| 234 | NM_005288_idx463 | NM_005288 | ACGTTTACCTATGTCATGCTC | GPR12 | DNA |
| 235 | NM_005288_idx466 | NM_005288 | TTTACCTATGTCATGCTCGTC | GPR12 | DNA |
| 236 | NM_005288_idx470 | NM_005288 | CCTATGTCATGCTCGTCATGC | GPR12 | DNA |
| 237 | NM_005288_idx472 | NM_005288 | TATGTCATGCTCGTCATGCTC | GPR12 | DNA |
| 238 | NM_005288_idx571 | NM_005288 | GTCAGACCGCTCACCAAGAAC | GPR12 | DNA |
| 239 | NM_005288_idx574 | NM_005288 | AGACCGCTCACCAAGAACAAC | GPR12 | DNA |
| 240 | NM_005288_idx576 | NM_005288 | ACCGCTCACCAAGAACAACGC | GPR12 | DNA |
| 241 | NM_005288_idx583 | NM_005288 | ACCAAGAACAACGCGGCCATC | GPR12 | DNA |
| 242 | NM_005288_idx586 | NM_005288 | AAGAACAACGCGGCCATCCTC | GPR12 | DNA |
| 243 | NM_005288_idx601 | NM_005288 | ATCCTCTCGGTGTCCTTCCTC | GPR12 | DNA |
| 244 | NM_005288_idx604 | NM_005288 | CTCTCGGTGTCCTTCCTCTTC | GPR12 | DNA |
| 245 | NM_005288_idx612 | NM_005288 | GTCCTTCCTCTTCATGTTTGC | GPR12 | DNA |
| 246 | NM_005288_idx614 | NM_005288 | CCTTCCTCTTCATGTTTGCGC | GPR12 | DNA |
| 247 | NM_005288_idx616 | NM_005288 | TTCCTCTTCATGTTTGCGCTC | GPR12 | DNA |
| 248 | NM_005288_idx620 | NM_005288 | TCTTCATGTTTGCGCTCATGC | GPR12 | DNA |
| 249 | NM_005288_idx623 | NM_005288 | TCATGTTTGCGCTCATGCTTC | GPR12 | DNA |
| 250 | NM_005288_idx626 | NM_005288 | TGTTTGCGCTCATGCTTCAGC | GPR12 | DNA |
| 251 | NM_005288_idx628 | NM_005288 | TTTGCGCTCATGCTTCAGCTC | GPR12 | DNA |
| 252 | NM_005288_idx631 | NM_005288 | GCGCTCATGCTTCAGCTCTAC | GPR12 | DNA |
| 253 | NM_005288_idx634 | NM_005288 | CTCATGCTTCAGCTCTACATC | GPR12 | DNA |
| 254 | NM_005288_idx635 | NM_005288 | TCATGCTTCAGCTCTACATCC | GPR12 | DNA |
| 255 | NM_005288_idx640 | NM_005288 | CTTCAGCTCTACATCCAGATC | GPR12 | DNA |

TABLE 2-continued

GPCRs involved in APP processing (SEQ ID NO: 1-3; 4-6), Sequences for expression-inhibiting agent (SEQ ID NO: 7-287), the hairpin loop sequence of the RNAi (SEQ ID NO: 288), and the domains of GPR3, GPR6, and GPR 12 (SEQ ID NO: 289-333):

| SEQ ID NO | Galapagos ID | Accession | Sequence | | Type |
|---|---|---|---|---|---|
| 256 | NM_005288_idx659 | NM_005288 | TCTGTAAGATTGTGATGAGGC | GPR12 | DNA |
| 257 | NM_005288_idx661 | NM_005288 | TGTAAGATTGTGATGAGGCAC | GPR12 | DNA |
| 258 | NM_005288_idx663 | NM_005288 | TAAGATTGTGATGAGGCACG | GPR12 | DNA |
| 259 | NM_005288_idx664 | NM_005288 | AAGATTGTGATGAGGCACGCC | GPR12 | DNA |
| 260 | NM_005288_idx665 | NM_005288 | AGATTGTGATGAGGCACGCCC | GPR12 | DNA |
| 261 | NM_005288_idx668 | NM_005288 | TTGTGATGAGGCACGCCCATC | GPR12 | DNA |
| 262 | NM_005288_idx685 | NM_005288 | CATCAGATAGCCCTGCAGCAC | GPR12 | DNA |
| 263 | NM_005288_idx686 | NM_005288 | ATCAGATAGCCCTGCAGCACC | GPR12 | DNA |
| 264 | NM_005288_idx691 | NM_005288 | ATAGCCCTGCAGCACCACTTC | GPR12 | DNA |
| 265 | NM_005288_idx717 | NM_005288 | CACGTCGCACTATGTGACCAC | GPR12 | DNA |
| 266 | NM_005288_idx718 | NM_005288 | ACGTCGCACTATGTGACCACC | GPR12 | DNA |
| 267 | NM_005288_idx748 | NM_005288 | GTCTCCACCCTGGCTATCATC | GPR12 | DNA |
| 268 | NM_005288_idx749 | NM_005288 | TCTCCACCCTGGCTATCATCC | GPR12 | DNA |
| 269 | NM_005288_idx776 | NM_005288 | CGTTTGCTGCTTGCTGGATGC | GPR12 | DNA |
| 270 | NM_005288_idx777 | NM_005288 | GTTTGCTGCTTGCTGGATGCC | GPR12 | DNA |
| 271 | NM_005288_idx781 | NM_005288 | GCTGCTTGCTGGATGCCTTTC | GPR12 | DNA |
| 272 | NM_005288_idx784 | NM_005288 | GCTTGCTGGATGCCTTTCACC | GPR12 | DNA |
| 273 | NM_005288_idx811 | NM_005288 | TCCTTGATAGCGGATFACACC | GPR12 | DNA |
| 274 | NM_005288_idx835 | NM_005288 | CCCTCCATCTATACCTACGCC | GPR12 | DNA |
| 275 | NM_005288_idx838 | NM_005288 | TCCATCTATACCTACGCCACC | GPR12 | DNA |
| 276 | NM_005288_idx839 | NM_005288 | CCATCTATACCTACGCCACCC | GPR12 | DNA |
| 277 | NM_005288_idx842 | NM_005288 | TCTATACCTACGCCACCCTCC | GPR12 | DNA |
| 278 | NM_005288_idx865 | NM_005288 | CCCGCCACCTACAATTCCATC | GPR12 | DNA |
| 279 | NM_005288_idx868 | NM_005288 | GCCACCTACAATTCCATCATC | GPR12 | DNA |
| 280 | NM_005288_idx872 | NM_005288 | CCTACAATTCCATCATCAACC | GPR12 | DNA |
| 281 | NM_005288_idx877 | NM_005288 | AATTCCATCATCAACCCTGTC | GPR12 | DNA |
| 282 | NM_005288_idx904 | NM_005288 | GCTTTCAGAAACCAAGAGATC | GPR12 | DNA |
| 283 | NM_005288_idx912 | NM_005288 | AAACCAAGAGATCCAGAAAGC | GPR12 | DNA |
| 284 | NM_005288_idx914 | NM_005288 | ACCAAGAGATCCAGAAAGCGC | GPR12 | DNA |
| 285 | NM_005288_idx928 | NM_005288 | AAAGCGCTCTGTCTCATTUGC | GPR12 | DNA |
| 286 | NM_005288_idx931 | NM_005288 | GCGCTCTGTCTCATTTGCTGC | GPR12 | DNA |
| 287 | NM_005288_idx941 | NM_005288 | TCATTTGCTGCGGCTGCATCC | GPR12 | DNA |
| 288 | Hairpin loop | | TTGCTATA | | DNA |
| 289 | N-term | | MMWGAGSPLAWLSAGSGNVNVSSVGPAEG PTGPAAPLPSPKA | GPR3 | Protein |

TABLE 2-continued

GPCRs involved in APP processing (SEQ ID NO: 1-3; 4-6), Sequences
for expression-inhibiting agent (SEQ ID NO: 7-287), the hairpin
loop sequence of the RNAi (SEQ ID NO: 288), and the domains of
GPR3, GPR6, and GPR 12 (SEQ ID NO: 289-333):

| SEQ ID NO | Galapagos ID | Accession Sequence | | Type |
|---|---|---|---|---|
| 290 | TM1 | WDVVLCISGTLVSCENALVVAII | GPR3 | Protein |
| 291 | IL1 | VGTPAFRAPMFL | GPR3 | Protein |
| 292 | TM2 | LVGSLAVADLLAGLGLVLHFAAV | GPR3 | Protein |
| 293 | EL1 | FCIGSAEMS | GPR3 | Protein |
| 294 | TM3 | LVLVGVLAMAFTASIGSLLAITV | GPR3 | Protein |
| 295 | IL2 | DRYLSLYNALTYYSETTVTR | GPR3 | Protein |
| 296 | TM4 | TYVMLALVWGGALGLGLLPVLAW | GPR3 | Protein |
| 297 | EL2 | NCLDGLTTCGVVYPLSKNH | GPR3 | Protein |
| 298 | TM5 | LVVLAIAFFMVFGIMLQLYAQIC | GPR3 | Protein |
| 299 | IL3 | RIVCRHAQQIALQRHLLPASHYVATRK | GPR3 | Protein |
| 300 | TM6 | GIATLAVVLGAFAACWLPFTVYC | GPR3 | Protein |
| 301 | EL3 | LLGDAHSPP | GPR3 | Protein |
| 302 | TM7 | LYTYLTLLPATYNSMINPIIYAF | GPR3 | Protein |
| 303 | C-term | RNQDVQKVLWAVCCCCSSSKIPF RSRSPSDV | GPR3 | Protein |
| 304 | N-term | MNASAASLNDSQVVVVAAEGAAAAATAAG GPDTGEWGPPAAAALGAGGGANGSLELSS QLSAGPPGLLLPAVNP | GPR6 | Protein |
| 305 | TM1 | WDVLLCVSGTVIAGENALVVALI | GPR6 | Protein |
| 306 | IL1 | ASTPALRTPMFV | GPR6 | Protein |
| 307 | TM2 | LVGSLATADLLAGCGLILHFVFQ | GPR6 | Protein |
| 308 | EL1 | YLVPSETVS | GPR6 | Protein |
| 309 | TM3 | LLTVGFLVASFAASVSSLLAITV | GPR6 | Protein |
| 310 | IL2 | DRYLSLYNALTYYSRRTLLG | GPR6 | Protein |
| 311 | TM4 | VHLLLAATWTVSLGLGLLPVLGW | GPR6 | Protein |
| 312 | EL2 | NCLAERAACSVVRPLARSH | GPR6 | Protein |
| 313 | TM5 | VALLSAAFFMVFGIMLHLYV | GPR6 | Protein |
| 314 | IL3 | RICQVVWRHAHQIALQQHCLAPPH LAATRK | GPR6 | Protein |
| 315 | TM6 | GVGTLAVVLGTFGASWLPFAIYC | GPR6 | Protein |
| 316 | EL3 | VVGSHEDPA | GPR6 | Protein |
| 317 | TM7 | VVGSHEDPAVYTYATLLPATYNSMI NPIIYAF | GPR6 | Protein |
| 318 | C-term | RNQEIQRALWLLLCCCFQSKVPFRSR SPSEV | GPR6 | Protein |
| 319 | N-term | MNEDLKVNLSGLPRDYLDAAAAENISAAVS SRVPAVEPEPELVVNP | GPR12 | Protein |
| 320 | TM1 | WDIVLCTSGTLISCENAIVVLII | GPR12 | Protein |
| 321 | IL1 | FHNPSLRAPMFL | GPR12 | Protein |

TABLE 2-continued

GPCRs involved in APP processing (SEQ ID NO: 1-3; 4-6), Sequences for expression-inhibiting agent (SEQ ID NO: 7-287), the hairpin loop sequence of the RNAi (SEQ ID NO: 288), and the domains of GPR3, GPR6, and GPR 12 (SEQ ID NO: 289-333):

| SEQ ID NO | Galapagos ID | Accession Sequence | | Type |
|---|---|---|---|---|
| 322 | TM2 | LIGSLALADLLAGIGLITNFVFA | GPR12 | Protein |
| 323 | EL1 | YLLQSEATK | GPR12 | Protein |
| 324 | TM3 | LVTIGLIVASFSASVCSLLAITV | GPR12 | Protein |
| 325 | IL2 | DRYLSLYYALTYHSERTVTF | GPR12 | Protein |
| 326 | TM4 | TYVMLVMLWGTSICLGLLPVMGW | GPR12 | Protein |
| 327 | EL2 | NCLRDESTCSVVRPLTKNN | GPR12 | Protein |
| 328 | TM5 | AAILSVSFLFMFALMLQLYIQIC | GPR12 | Protein |
| 329 | IL3 | KIVNRHAHQIALQHHFLATSHYVTTRK | GPR12 | Protein |
| 330 | TM6 | GVSTLAIILGTFAACWMPFTLYS | GPR12 | Protein |
| 331 | EL3 | LIADYTYPS | GPR12 | Protein |
| 332 | TM7 | IYTYATLLPATYNSIINPVIYAF | GPR12 | Protein |
| 333 | C-term | RNQEIQKALCLICCGCIPSSLAQRARSPSDV | GPR12 | Protein |

Example 3

Amyloid Beta Peptide Reduction Via Knock Down of GPCR Expression

The effect of an antagonist can be mimicked through the use of siRNA-based strategies, which result in decreased expression levels of the targeted protein. For example, ttransfection with GPR3 siRNA reduces amyloid beta 1-42.

Figure 4:
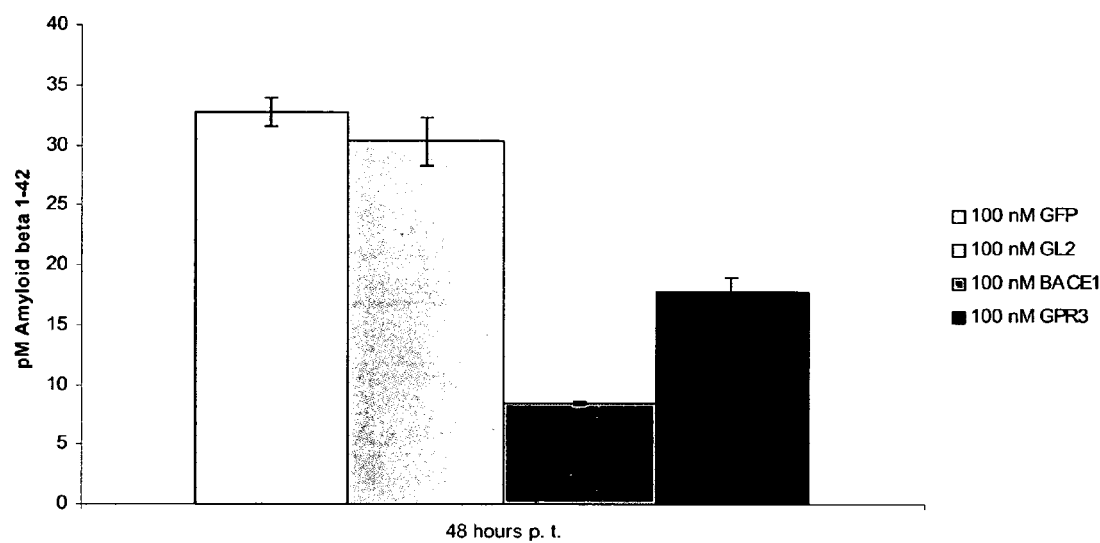
FIG. 4: Transfection with GPR3 siRNA reduces Amyloid beta 1-42: HEK293 APPwt cl29 cells are transfected with siRNA of GPR3, eGFP, Luciferase and BACE and amyloid beta 1-42 levels are determined. Cells are transfected and 24 hours after transfection, medium is refreshed and cells are allowed to accumulate amyloid beta for 24 hours (48 hours post transfection (p.t.)). Amyloid beta is determined by means of the amyloid beta 1-42 ELISA as described above. Data are presented in pM of amyloid beta. RNA levels of GPR3 are determined from these samples.

HEK293 APPwt cells are transfected with a smart pool of siRNAs of GPR3 (Dharmacon, USA: Table 3), eGFP, Luciferase and BACE with Oligofectamine. 24 hours after transfection, the medium is refreshed and the cells are allowed to accumulate amyloid beta peptides in the conditioned medium for 24 hours prior to ELISA analysis as described above. The data clearly show that siRNA targeted against GPR3 RNA levels reduce amyloid beta 1-42 levels compared to the control conditions (FIG. 4). In conclusion, these data show that GPR3 modulates the levels of secreted amyloid beta. The same procedure is used for the analysis of APP processing by GPR6 and GPR12.

TABLE 3

Specific siRNAs for GPR3 (Dharmacon, USA; SEQ ID NO:334-337)

| Gene symbol | NM number | Dharmacon Cat. number | Full sequence siRNA | SEQ ID NO: |
|---|---|---|---|---|
| GPR3 | NM_005281 | D-003951-01 | GTTTATCCACTCTCCAAGA | 334 |
| GPR3 | NM_005281 | D-003951-02 | TTTATCCACTCTCCAAGAA | 335 |
| GPR3 | NM_005281 | D-003951-03 | CCACCTCTCTACACCTATC | 336 |
| GPR3 | NM_005281 | D-003951-04 | ACCGCTACCTTTCTCTGTA | 337 |

Example 4

Expression of GPR3 in the Human Brain

Upon identification of a modulator of APP processing, it is important to evaluate whether the modulator is expressed in the tissue and the cells of interest. This can be achieved by measuring the RNA and/or protein levels in the tissue and cells. In recent years, RNA levels are being quantified through real time PCR technologies, whereby the RNA is first transcribed to cDNA and then the amplification of the cDNA of interest is monitored during a PCR reaction. The amplification plot and the resulting Ct value are indicators for the amount of RNA present in the sample. Determination of the levels of household keeping genes allows the normalization of RNA levels of the target gene between different RNA samples, represented as ΔCt values.

To assess whether the GPCRs of the invention are expressed in the human brain, real time PCR with GAPDH specific primers and specific primers for each GPCR of the invention is performed on human total brain, human cerebral cortex, and human hippocampal total RNA (BD Biosciences) (see Table 4).

TABLE 4

Primers used in quantitative real time PCR-analysis of GPR3 expression levels
(SEQ ID NO:338-339)

| Gene | Primer name | SEQ ID NO: | Primer sequence |
|---|---|---|---|
| GPR3 | GPR3_Hs_For | 338 | GGCCTTTACCGCCAGCAT TCTGAATAGTAGGTGAG |
|  | GPR3_Hs_Rev | 339 | GGCATTG |

GAPDH is detected with a Taqman probe, while for the other GPCRs SybrGreen was used. In short, 40 ng of RNA is reverse-transcribed to DNA using the MultiScribe Reverse Transcriptase (50 U/µl) enzyme (Applied BioSystems). The resulting cDNA is amplified with AmpliTaq Gold DNA polymerase (Applied BioSystems) during 40 cycles using an ABI PRISM® 7000 Sequence Detection System.

Total brain, cerebral cortex and hippocampal total RNA are analyzed for the presence of the GPCR transcripts via quantitative real time PCR. For GPR3, the obtained Ct values indicate that it is detected in all RNA samples (Table 5).

To gain more insight into the specific cellular expression, immunohistochemistry (protein level) and/or in situ hybridization (RNA level) are carried out on sections from human normal and Alzheimer's brain hippocampal, cortical and subcortical structures. These results indicate whether expression occurs in neurons, microglia cells, or astrocytes. The comparison of diseased tissue with healthy tissue indicates whether GPR3 is expressed in the diseased tissue and whether its expression level is changed compared to the non-pathological situation. The same procedure is used for expression profiling of GPR6 and GPR12.

TABLE 5

Quantitative real time PCR Ct values: Total human brain, cerebral cortex or hippocampus RNA tested for the presence of GPR3 RNA via quantitative real time PCR. GAPDH RNA is used to normalize all samples (ΔCt).

| Human Tissue | GAPDH Ct-values | | GPR3 Ct-values | | ΔCt (+RT) |
|---|---|---|---|---|---|
|  | +RT | −RT | +RT | −RT |  |
| Total brain | 21.29 | NA | 24.93 | 33.07 | 3.64 |
| Hippocampus | 21.65 | NA | 25.77 | 36.14 | 4.12 |
| Cerebral cortex | 20.97 | NA | 25.19 | 35.73 | 4.22 |

Example 5

Amyloid Beta Production in Rat Primary Neuronal Cells

In order to investigate whether GPR3 affects amyloid beta production in a real neuron, human or rat primary hippocampal or cortical neurons are transduced with adenovirus containing the GPR3 cDNA. Amyloid beta levels are determined by ELISA (see EXAMPLE 1). Since rodent APP genes carry a number of mutations in APP compared to the human sequence, they produce less amyloid beta 1-40 and 1-42. In order to achieve higher amyloid beta levels, co-transduction of GPR3 with human wild type APP or human Swedish mutant APP (which enhances amyloid beta production) cDNA is performed.

Rat primary neuron cultures are prepared from brain of E18-E19-day-old fetal Sprague Dawley rats according to Goslin and Banker (Culturing Nerve cells, second edition, 1998 ISBN 0-262-02438-1). Briefly, single cell suspensions obtained from the hippocampus or cortices are prepared. The number of viable cells is determined and plated on poly-L-lysine-coated plastic 96-well plates in minimal essential medium (MEM) supplemented with 10% horse serum. The cells are seeded at a density of 50,000 cells per well (i.e. about 166,000 cells/cm$^2$). After 3-4 h, culture medium is replaced by 160 µl serum-free neurobasal medium with B27 supplement (GIBCO BRL). Cytosine arabinoside (5 µM) is added 24 h after plating to prevent nonneuronal (glial) cell proliferation.

Neurons are used at day 5 after plating. Before adenoviral transduction, 150 µl conditioned medium of these cultures is transferred to the corresponding wells in an empty 96-well plate and 50 µl of the conditioned medium is returned to the cells. The remaining 100 µl/well is stored at 37° C. and 5% $CO_2$. Hippocampal primary neuron cultures are infected with the crude lysate of Ad5C09Att00/A011200-GPR3_v3, Ad5C09Att00/A010801 LacZ_v1, Ad5C09Att00/A010800-eGFP_v1 and Ad5C09Att00/A010800-luc_v17 viruses containing the cDNA of GPR3, LacZ, eGFP and luciferase respectively at different MOIs, ranging from 250 to 2000. In addition the cells are also infected with the purified adenovirus Ad5C01Att01/A010800 APP_v6 expressing human wild type APP695 at an MOI of 2000. Sixteen to twenty-four hours after transduction, virus is removed and cultures are washed with 100 µl pre-warmed fresh neurobasal medium. After removal of the wash solution, new medium, containing 50 µl of the stored conditioned medium and 50 µl of fresh neurobasal medium, is transferred to the corresponding cells. Medium was harvested after 48 and 72 hours. The cell number in the wells was determined by assessing the ATP levels. Amyloid beta concentration was determined by amyloid beta 1-42 specific ELISA (see EXAMPLE 1). Amyloid beta 1-42 levels are normalized for cell number.

Figure 6:
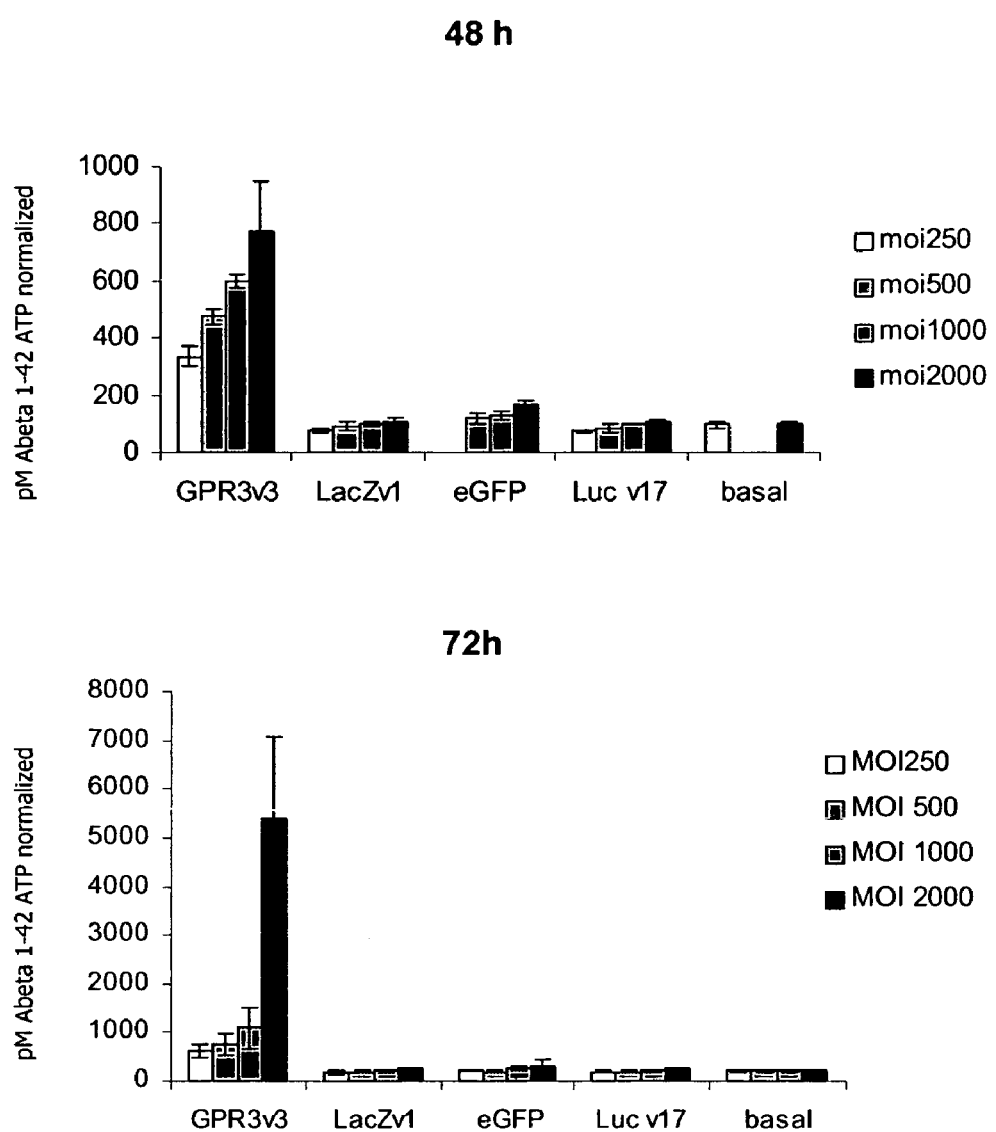
FIG. 6: Graph of amyloid beta peptide levels in neurons transfected with a variety of protein expression viruses at different MOI. The graph shows that increased levels of GPR3 overexpression in primary neurons result in a corresponding dose dependent increase of amyloid beta 1-42 levels compared to the negative controls.

The data (FIG. 6) clearly indicate that increased levels of over expression of GPR3 in the primary neurons result in a corresponding dose dependent increase of amyloid beta 1-42 levels compared to the negative control viruses.

Example 6

Ligand Screens for GPCRs

Reporter Gene Screen.

Mammalian cells such as HEK293 or CHO-K1 cells are either stably transfected with a plasmid harboring the luciferase gene under the control of a cAMP dependent promoter (CRE elements) or transduced with an adenovirus harboring a luciferase gene under the control of a cAMP dependent promoter. In addition reporter constructs can be used with the luciferase gene under the control of a $Ca^{2+}$ dependent promoter (NF-AT elements) or a promoter that is controlled by activated NF-κB. These cells, expressing the reporter construct, are then transduced with an adenovirus harboring the cDNA of the GPCR of the present invention. Forty (40) hours after transduction the cells are treated with the following:

a) an agonist for the receptor (e.g. sphingosine 1 phosphate) and screened against a large collection of reference compounds comprising peptides (LOPAP, Sigma Aldrich), lipids (Biomol, TimTech), carbohydrates (Specs), natural compounds (Specs, TimTech), small chemical compounds (Tocris), commercially available screening libraries, and compounds that have been demonstrated to have binding affinity for a polypeptide comprising an amino acid sequence selected from the group consisting of SEQ ID NO: 4-6, 289-333, including compounds comprising aryloxydithiourea (see U.S. Pat. No. 6,420,563), its salts, hydrates, or solvates, or b) a large collection of reference compounds comprising peptides (LOPAP, Sigma Aldrich), lipids (Biomol, TimTech), carbohydrates (Specs), natural compounds (Specs, TimTech), small chemical compounds (Tocris), commercially available screening libraries, and compounds that have been demonstrated to have binding affinity for a polypeptide comprising an amino acid sequence selected from the group consisting of SEQ ID NO: 4-6, 289-333, including compounds comprising aryloxydithiourea (see U.S. Pat. No. 6,420,563), its salts, hydrates, or solvates, only, as GPR3 is considered to be a constitutively active GPCR.

Compounds, which decrease the agonist induced increase in luciferase activity or the constitutive activity, are considered to be antagonists or inverse agonists for the GPR3. These compounds are screened again for verification and screened against their effect on secreted amyloid beta peptide levels. The compounds are also screened to verify binding to the GPCR. The binding, amyloid-beta peptide and reporter activity assays can be performed in essentially any order to screen compounds.

In addition, cells expressing the NF-AT reporter gene can be transduced with an adenovirus harboring the cDNA encoding the α-subunit of $G_{15}$ or chimerical $G_\alpha$ subunits. $G_{15}$ is a promiscuous G protein of the $G_q$ class that couples to many different GPCRs and as such re-directs their signaling towards the release of intracellular $Ca^{2+}$ stores. The chimerical G alpha subunits are members of the $G_s$ and $G_{i/o}$ family by which the last 5 C-terminal residues are replaced by those of Gαq, these chimerical G-proteins also redirect cAMP signaling to $Ca^{2+}$ signaling.

FLIPR Screen.

Mammalian cells such as HEK293 or CHO-K1 cells are stably transfected with an expression plasmid construct harboring the cDNA of a GPCR of the present invention. Cells are seeded, grown, and selected until sufficient stable cells can be obtained. Cells are loaded with a $Ca^{2+}$ dependent fluorophore such as Fura3 or Fura4. After washing away the excess of fluorophore the cells are screened against a large collection of reference compounds comprising peptides (LOPAP, Sigma Aldrich), lipids (Biomol, TimTech), carbohydrates (Specs), natural compounds (Specs, TimTech), small chemical compounds (Tocris), commercially available screening libraries, and compounds that have been demonstrated to have binding affinity for a polypeptide comprising an amino acid sequence selected from the group consisting of SEQ ID NO: 4-6, 289-333, including compounds comprising aryloxydithiourea (see U.S. Pat. No. 6,420,563), its salts, hydrates, or solvates, by simultaneously adding an agonist (alternatively no agonist need be added if the constitutive activity of the receptor is used) and a compound to the cells. Activation of the receptor is measured as an almost instantaneously increase in fluorescence due to the interaction of the fluorophore and the $Ca^{2+}$ that is released. Compounds that reduce or inhibit the agonist induced increase in fluorescence (or constitutive fluorescence) are considered to be antagonists or inverse agonists for the receptor they are screened against. These compounds will be screened again to measure the amount of secreted amyloid beta peptide as well as binding to the GPCR.

AequoScreen.

CHO cells, stably expressing Apoaequorin are stably transfected with a plasmid construct harboring the cDNA of a GPCR. Cells are seeded, grown, and selected until sufficient stable cells can be obtained. The cells are loaded with coelenterazine, a cofactor for apoaequorin. Upon receptor activation intracellular $Ca^{2+}$ stores will be emptied and the aequorin will react with the coelenterazine in a light emitting process. The emitted light is a measure for receptor activation. The CHO, stable expressing both the apoaequorin and the receptor are screened against a large collection of reference compounds comprising peptides (LOPAP, Sigmna Aldrich), lipids (Biomol, TimTech), carbohydrates (Specs), natural compounds (Specs, TimTech), small chemical compounds (Tocris), commercially available screening libraries, and compounds that have been demonstrated to have binding affinity for a polypeptide comprising an amino acid sequence selected from the group consisting of SEQ ID NO: 4-6, 289-333, including compounds comprising aryloxydithiourea (see U.S. Pat. No. 6,420,563), its salts, hydrates, or solvates, by simultaneously adding an agonist (alternatively no agonist need be added if the constitutive activity of the receptor is used) and a compound to the cells. Activation of the receptor is measured as an almost instantaneously light flash due to the interaction of the apoaequorin, coelenterazine, and the $Ca^{2+}$ that is released. Compounds that reduce or inhibit the agonist induced increase in light or the constitutive activity are considered to be antagonists or inverse agonists for the receptor they are screened against. These compounds will be screened again to measure the amount of secreted amyloid beta peptide as well as binding to the GPCR.

In addition, CHO cells stable expressing the apoaequorin gene are stably transfected with a plasmid construct harboring the cDNA encoding the α-subunit of $G_{15}$ or chimerical $G_\alpha$ subunits. $G_{15}$ is a promiscuous G protein of the $G_q$ class that couples to many different GPCRs and as such redirects their signaling towards the release of intracellular $Ca^{2+}$ stores. The chimerical G alpha subunits are members of the $G_s$ and $G_{i/o}$ family by which the last 5 C-terminal residues are replaced by those of $G_{\alpha q}$, these chimerical G-proteins also redirect cAMP signaling to $Ca^{2+}$ signaling.

Screening for Compounds that Bind to the GPCR Polypeptides (Displacement Experiment)

Compounds are screened for binding to the GPCR polypeptides. The affinity of the compounds to the polypeptides is determined in a displacement experiment. In brief, the GPCR polypeptides are incubated with a labeled (radiolabeled, fluorescent labeled) ligand that is known to bind to the polypeptide (e.g., spingosine-1-phosphate or dihydrosphingosine-1-phosphate) and with an unlabeled compound. The displacement of the labeled ligand from the polypeptide is determined by measuring the amount of labeled ligand that is still associated with the polypeptide. The amount associated with the polypeptide is plotted against the concentration of the compound to calculate $IC_{50}$ values. This value reflects the binding affinity of the compound to its target, i.e. the GPCR polypeptides. Strong binders have an $IC_{50}$ in the nanomolar and even picomolar range. Compounds that have an $IC_{50}$ of at least 10 micromol or better (nmol to pmol) are applied in beta amyloid secretion assay to check for their effect on the beta amyloid secretion and processing. The GPCR polypeptides can be prepared in a number of ways depending on whether the assay will be run on cells, cell fractions or biochemically, on purified proteins.

Screening for Compounds that Bind to the GPCR Polypeptide (Generic GPCR Screening Assay)

When a G protein receptor becomes constitutively active, it binds to a G protein (Gq, Gs, Gi, Go) and stimulates the binding of GTP to the G protein. The G protein then acts as a GTPase and slowly hydrolyses the GTP to GDP, whereby the receptor, under normal conditions, becomes deactivated. However, constitutively activated receptors continue to exchange GDP to GTP. A non-hydrolyzable analog of GTP, [$^{35}$S]GTP?S, can be used to monitor enhanced binding to membranes which express constitutively activated receptors. It is reported that [$^{35}$S]GTP?S can be used to monitor G protein coupling to membranes in the absence and presence of ligand. Moreover, a preferred approach is the use of a GPCR-G protein fusion protein. The strategy to generate a GPR3-G protein fusion protein is well known for those known in the art. Membranes expressing GPR3-G protein fusion protein are prepared for use in the direct identification of candidate compounds such as inverse agonist. Homogenized membranes with GPR3-G protein fusion protein are transferred in a 96-well plate. A pin-tool is used to transfer a candidate compound in each well plus [$^{35}$S]GTP?S, followed by incubation on a shaker for 60 minutes at room temperature. The assay is stopped by spinning of the plates at 4000 RPM for 15 minutes at 22° C. The plates are then aspirated and radioactivity is then read. The same procedure is used for analysis of GPR6 and GPR12.

Receptor Ligand Binding Study on Cell Surface

The receptor is expressed in mammalian cells (HEK293, CHO, COS7) by adenoviral transducing the cells (see U.S. Pat. No. 6,340,595). The cells are incubated with both labeled ligand (iodinated, tritiated, or fluorescent) and the unlabeled compound at various concentrations, ranging from 10 pM to 10 μM (3 hours at 4° C.: 25 mM HEPES, 140 mM NaCl, 1 mM CaCl$_2$, 5 mM MgCl$_2$ and 0.2% BSA, adjusted to pH 7.4). Reactions mixtures are aspirated onto PEI-treated GF/B glass filters using a cell harvester (Packard). The filters are washed twice with ice cold wash buffer (25 mM HEPES, 500 mM NaCl, 1 mM CaCl$_2$, 5 mM MgCl$_2$, adjusted to pH 7.4). Scintillant (MicroScint-10; 35 μl) is added to dried filters and the filters counted in a (Packard Topcount) scintillation counter. Data are analyzed and plotted using Prism software (GraphPad Software, San Diego, Calif.). Competition curves are analyzed and IC$_{50}$ values calculated. If one or more data points do not fall within the sigmoidal range of the competition curve or close to the sigmoidal range the assay is repeated and concentrations of labeled ligand and unlabeled compound adapted to have more data points close to or in the sigmoidal range of the curve.

Receptor Ligand Binding Studies on Membrane Preparations

Membranes preparations are isolated from mammalian cells (HEK293, CHO, COS7) cells over expressing the receptor is done as follows: Medium is aspirated from the transduced cells and cells are harvested in 1×PBS by gentle scraping. Cells are pelleted (2500 rpm 5 min) and resuspended in 50 mM Tris pH 7.4 (10×10$^6$ cells/ml). The cell pellet is homogenized by sonicating 3×5 sec (UP50H; sonotrode MS1; max amplitude: 140 μm; max Sonic Power Density: 125 W/cm$^2$). Membrane fractions are prepared by centrifuging 20 min at maximal speed (13000 rpm ~15 000 to 20 000 g or rcf). The resulting pellet is resuspended in 500 μl 50 mM Tris pH 7.4 and sonicated again for 3×5 sec. The membrane fraction is isolated by centrifugation and finally resuspended in PBS. Binding competition and derivation of IC$_{50}$ values are determined as described above.

Internalization Screen (1)

Activation of a GPCR-associated signal transduction pathway commonly leads to translocation of specific signal transduction molecules from the cytoplasm to the plasma membrane or from the cytoplasm to the nucleus. Norak has developed their transfluor assay based on agonist-induced translocation of receptor-β-arrestin-GFP complex from the cytosol to the plasma membrane and subsequent internalization of this complex, which occurs during receptor desensitization. A similar assay uses GFP tagged receptor instead of B3-arrestin. HEK293 cells are transduced with a GPR3-eGFP vector that translates for a GPR3-eGFP fusion protein. 48 hours after transduction, the cells are set to fresh serum-free medium for 60 minutes and treated with a ligand (e.g. 100 nM sphingosine 1 phosphate) for 15, 30, 60 or 120 minutes at 37° C. and 5% CO$_2$. After indicated exposure times, cells are washed with PBS and fixed with 5% paraformaldehyde for 20 minutes at RT. GFP fluorescence is visualized with a Zeiss microscope with a digital camera. This method aims for the identification of compounds that inhibit a ligand-mediated (constitutive activity-mediated) translocation of the fusion protein to intracellular compartments. The same procedure is used for analysis of GPR6 and GPR12.

Internalization Screen (2)

Various variations on translocation assays exists using β-arrestin and β-galactosidase enzyme complementation and BRET based assays with receptor as energy donor and 1-arrestin as energy acceptor. Also the use of specific receptor antibodies labeled with pH sensitive dyes are used to detect agonist induced receptor translocation to acidic lysosomes. All of he translocation assays are used for screening for both agonistic and antagonistic acting ligands.

Melanophore Assay (Arena Pharmaceutical)

The melanophore assay is based on the ability of GPCRs to alter the distribution of melanin containing melanosomes in Xenopus melanophores. The distribution of the melanosomes depends on the exogenous receptor that is either Gi/o or Gs/q coupled. The distribution of the melanosomes (dispersed or aggregated) is easily detected by measuring light absorption. This type of assay is used for both agonist as well as antagonist compound screens.

We claim:

1. A method for identifying a compound that inhibits the processing of amyloid-beta precursor protein in a mammalian cell that expresses amyloid-beta precursor protein and overexpresses a polypeptide comprising the amino acid sequence of SEQ ID NO:4, said method comprising
   a) contacting a compound with a polypeptide comprising the amino acid sequence of SEQ ID NO:4 wherein said polypeptide is membrane-bound or present as a transmembrane cell receptor in a mammalian cell that expresses amyloid-beta precursor protein; and
   b) measuring levels of one or more amyloid-beta peptides selected from the group consisting of one or more of amyloid-beta peptide 1-42, 1-40, 11-42 and 11-40; and
   c) determining if said levels of said one or more amyloid-beta peptides expressed in said mammalian cell that is not contacted with said compound.

2. The method of claim 1 further comprising the following steps:
   measuring the levels of a second messenger selected from the group consisting of cyclic AMP and $Ca^{2+}$; and
   determining if said levels of said second messenger are decreased as compared to levels of said second messenger expressed in said mammalian cell that is not contacted with said compound.

3. The method of claim 1 wherein said amyloidal-beta peptide is amyloidal-beta peptide 1-42.

4. The method according to claim 2 wherein said step of measuring the level of a second messenger comprises determining the expression of a reporter gene in said mammalian cell, wherein said reporter gene is controlled by a promoter responsive to the second messenger.

5. The method according to claim 4 wherein the reporter gene is selected from the group consisting of alkaline phosphates, GFP, eGFP, dGFP, luciferase and β-galactosidase.

6. The method according to claim 1, wherein said compound is selected from the group consisting of compounds of a commercially available screening library and compounds that have been demonstrated to have binding affinity for a polypeptide comprising SEQ ID NO: 4.

7. The method according to claim 1, wherein said compound is an aryloxydithiourea, its salts, hydrates, or solvates.

8. The method according to claim 1, wherein said compound has a binding affinity for said polypeptide.

9. The method according to claim 1 wherein said mammalian cell has been transduced to overexpress said polypeptide comprising the amino acid sequence of SEQ ID NO:4.

10. The method according to claim 8 wherein said mammalian cell has been transduced to overexpress said polypeptide comprising the amino acid sequence of SEQ ID NO:4.

11. The method according to claim 1 wherein said mammalian cell endogenously overexpresses said polypeptide comprising the amino acid sequence of SEQ ID NO:4.

* * * * *

SEQUENCE LISTING

<160> NUMBER OF SEQ ID NOS: 620

<210> SEQ ID NO 1
<211> LENGTH: 993
<212> TYPE: DNA

<210> SEQ ID NO 1
<211> LENGTH: 993
<212> TYPE: DNA
<213> ORGANISM: Homo sapiens

<400> SEQUENCE: 1

| | | | | | |
|---|---|---|---|---|---|
| atgatgtggg | gtgcaggcag | ccctctggcc | tggctctcag | ctggctcagg | caacgtgaat | 60 |
| gtaagcagcg | tgggcccagc | agaggggccc | acaggtccag | ccgcaccact | gccctcgcct | 120 |
| aaggcctggg | atgtggtgct | ctgcatctca | ggcaccctgg | tgtcctgcga | gaatgcgcta | 180 |
| gtggtggcca | tcatcgtggg | cactcctgcc | ttccgtgccc | ccatgttcct | gctggtgggc | 240 |
| agcctggccg | tggcagacct | gctggcaggc | ctgggcctgg | tcctgcactt | tgctgctgtc | 300 |
| ttctgcatcg | gctcagcgga | gatgagcctg | tgctggttg | gcgtgctggc | aatggccttt | 360 |
| accgccagca | tcggcagtct | actggccatc | actgtcgacc | gctacctttc | tctgtacaat | 420 |
| gccctcacct | actattcaga | gacaacagtg | acacggacct | atgtgatgct | ggccttagtg | 480 |
| tggggaggtg | ccctgggcct | ggggctgctg | cctgtgctgg | cctggaactg | cctggatggc | 540 |
| ctgaccacat | gtggcgtggt | ttatccactc | tccaagaacc | atctggtagt | tctggccatt | 600 |
| gccttcttca | tggtgtttgg | catcatgctg | cagctctacg | cccaaatctg | ccgcatcgtc | 660 |
| tgccgccatg | cccagcagat | tgcccttcag | cggcacctgc | tgcctgcctc | ccactatgtg | 720 |
| gccacccgca | agggcattgc | cacactggcc | gtggtgcttg | gagcctttgc | cgcctgctgg | 780 |
| ttgcccttca | ctgtctactg | cctgctgggt | gatgcccact | ctccacctct | ctacacctat | 840 |
| cttaccttgc | tccctgccac | ctacaactcc | atgatcaacc | ctatcatcta | cgccttccgc | 900 |
| aaccaggatg | tgcagaaagt | gctgtgggct | gtctgctgct | gctgttcctc | ttccaagatc | 960 |
| cccttccgat | cccgctcccc | cagtgatgtc | tag | | | 993 |

<210> SEQ ID NO 2
<211> LENGTH: 1089
<212> TYPE: DNA
<213> ORGANISM: Homo sapiens

<400> SEQUENCE: 2

| | | | | | |
|---|---|---|---|---|---|
| atgaacgcga | gcgccgcctc | gctcaacgac | tcccaggtgg | tggtagtggc | ggccgaagga | 60 |
| gcggcggcgg | cggccacagc | agcaggggg | ccggacacgg | gcgaatgggg | accccctgct | 120 |
| gcggcggctc | taggagccgg | cggcggagct | aatgggtctc | tggagctgtc | ctcgcagctg | 180 |
| tcggctgggc | caccgggact | cctgctgcca | gcggtgaatc | cgtgggacgt | gctcctgtgc | 240 |
| gtgtcgggga | cagtgatcgc | tggagaaaac | gcgctggtgg | tggcgctcat | cgcgtccact | 300 |
| ccggcgctgc | gcacgcccat | gttcgtgctg | gtaggcagcc | tggccaccgc | tgacctgttg | 360 |
| gcgggctgtg | gcctcatctt | gcactttgtg | ttccagtact | tggtgccctc | ggagactgtg | 420 |
| agtctgctca | cggtgggctt | cctcgtggcc | tccttcgccg | cctctgtcag | cagcctgctg | 480 |
| gccattacgg | tggaccgcta | cctgtccctg | tataacgcgc | tcacctatta | ctcgcgccgg | 540 |
| accctgttgg | gcgtgcacct | cctgcttgcc | gccacttgga | ccgtgtccct | aggcctgggg | 600 |
| ctgctgcccg | tgctgggctg | gaactgcctg | gcagagcgcg | ccgcctgcag | cgtggtgcgc | 660 |
| ccgctggcgc | gcagccacgt | ggctctgctc | tccgccgcct | tcttcatggt | cttcggcatc | 720 |
| atgctgcacc | tgtacgtgcg | catctgccag | gtggtctggc | gccacgcgca | ccagatcgcg | 780 |
| ctgcagcagc | actgcctggc | gccacccat | ctcgctgcca | ccagaaaggg | tgtgggtaca | 840 |
| ctggctgtgg | tgctgggcac | tttcggcgcc | agctggctgc | ccttcgccat | ctattgcgtg | 900 |
| gtgggcagcc | atgaggaccc | ggcggtctac | acttacgcca | ccctgctgcc | cgccacctac | 960 |
| aactccatga | tcaatcccat | catctatgcc | ttccgcaacc | aggagatcca | gcgcgccctg | 1020 |

```
tggctcctgc tctgtggctg tttccagtcc aaagtgccct tcgttccag gtctcccagc    1080 gaggtctga                                                            1089
```

<210> SEQ ID NO 3
<211> LENGTH: 1005
<212> TYPE: DNA
<213> ORGANISM: Homo sapiens

<400> SEQUENCE: 3

```
atgaatgaag acctgaaggt caatttaagc gggctgcctc gggattattt agatgccgct     60
gctgcggaga acatctcggc tgctgtctcc tcccgggttc ctgccgtaga gccagagcct    120
gagctcgtag tcaaccccctg ggacattgtc ttgtgtacct cgggaacccct catctcctgt  180 gaaaatgcca ttgtggtcct tatcatcttc acaaccccca gcctgcgagc acccatgttc    240
ctgctaatag gcagcctggc tcttgcagac ctgctggccg gcattggact catcaccaat    300 tttgttttg cctacctgct tcagtcagaa gccaccaagc tggtcacgat cggcctcatt    360
gtcgcctctt tctctgcctc tgtctgcagc ttgctggcta tcactgttga ccgctacctc    420
tcactgtact acgctctgac gtaccattcg gagaggacgg tcacgtttac ctatgtcatg    480
ctcgtcatgc tctgggggac ctccatctgc ctggggctgc tgcccgtcat gggctggaac    540
tgcctccgag acgagtccac ctgcagcgtg gtcagaccgc tcaccaagaa caacgcggcc    600
atcctctcgg tgtccttcct cttcatgttt gcgctcatgc ttcagctcta catccagatc    660
tgtaagattg tgatgaggca cgcccatcag atagccctgc agcaccactt cctggccacg    720
tcgcactatg tgaccacccg gaaagggggtc tccaccctgg ctatcatcct ggggacgttt    780
gctgcttgct ggatgccttt caccctctat tccttgatag cggattacac ctacccctcc    840 atctataccct acgccaccct cctgcccgcc acctacaatt ccatcatcaa ccctgtcata    900
tatgctttca gaaaccaaga gatccagaaa gcgctctgtc tcatttgctg cggctgcatc    960
ccgtccagtc tcgcccagag agcgcgctcg cccagtgatg tgtag                   1005
```

<210> SEQ ID NO 4
<211> LENGTH: 330
<212> TYPE: PRT
<213> ORGANISM: Homo sapiens

<400> SEQUENCE: 4

```
Met Met Trp Gly Ala Gly Ser Pro Leu Ala Trp Leu Ser Ala Gly Ser
1               5                   10                  15

Gly Asn Val Asn Val Ser Ser Val Gly Pro Ala Glu Gly Pro Thr Gly
            20                  25                  30

Pro Ala Ala Pro Leu Pro Ser Pro Lys Ala Trp Asp Val Val Leu Cys
        35                  40                  45

Ile Ser Gly Thr Leu Val Ser Cys Glu Asn Ala Leu Val Val Ala Ile
    50                  55                  60

Ile Val Gly Thr Pro Ala Phe Arg Ala Pro Met Phe Leu Leu Val Gly
65                  70                  75                  80

Ser Leu Ala Val Ala Asp Leu Leu Ala Gly Leu Gly Leu Val Leu His
                85                  90                  95

Phe Ala Ala Val Phe Cys Ile Gly Ser Ala Glu Met Ser Leu Val Leu
            100                 105                 110

Val Gly Val Leu Ala Met Ala Phe Thr Ala Ser Ile Gly Ser Leu Leu
        115                 120                 125
```

```
Ala Ile Thr Val Asp Arg Tyr Leu Ser Leu Tyr Asn Ala Leu Thr Tyr
        130                 135                 140

Tyr Ser Glu Thr Thr Val Thr Arg Thr Tyr Val Met Leu Ala Leu Val
145                 150                 155                 160

Trp Gly Gly Ala Leu Gly Leu Gly Leu Leu Pro Val Leu Ala Trp Asn
                165                 170                 175

Cys Leu Asp Gly Leu Thr Thr Cys Gly Val Val Tyr Pro Leu Ser Lys
                180                 185                 190

Asn His Leu Val Val Leu Ala Ile Ala Phe Phe Met Val Phe Gly Ile
                195                 200                 205

Met Leu Gln Leu Tyr Ala Gln Ile Cys Arg Ile Val Cys Arg His Ala
        210                 215                 220

Gln Gln Ile Ala Leu Gln Arg His Leu Leu Pro Ala Ser His Tyr Val
225                 230                 235                 240

Ala Thr Arg Lys Gly Ile Ala Thr Leu Ala Val Val Leu Gly Ala Phe
                245                 250                 255

Ala Ala Cys Trp Leu Pro Phe Thr Val Tyr Cys Leu Leu Gly Asp Ala
                260                 265                 270

His Ser Pro Pro Leu Tyr Thr Tyr Leu Thr Leu Leu Pro Ala Thr Tyr
                275                 280                 285

Asn Ser Met Ile Asn Pro Ile Ile Tyr Ala Phe Arg Asn Gln Asp Val
        290                 295                 300

Gln Lys Val Leu Trp Ala Val Cys Cys Cys Cys Ser Ser Ser Lys Ile
305                 310                 315                 320

Pro Phe Arg Ser Arg Ser Pro Ser Asp Val
                325                 330

<210> SEQ ID NO 5
<211> LENGTH: 362
<212> TYPE: PRT
<213> ORGANISM: Homo sapiens

<400> SEQUENCE: 5

Met Asn Ala Ser Ala Ala Ser Leu Asn Asp Ser Gln Val Val Val Val
1               5                   10                  15

Ala Ala Glu Gly Ala Ala Ala Ala Thr Ala Ala Gly Gly Pro Asp
                20                  25                  30

Thr Gly Glu Trp Gly Pro Pro Ala Ala Ala Ala Leu Gly Ala Gly Gly
        35                  40                  45

Gly Ala Asn Gly Ser Leu Glu Leu Ser Ser Gln Leu Ser Ala Gly Pro
    50                  55                  60

Pro Gly Leu Leu Leu Pro Ala Val Asn Pro Trp Asp Val Leu Leu Cys
65                  70                  75                  80

Val Ser Gly Thr Val Ile Ala Gly Glu Asn Ala Leu Val Val Ala Leu
                85                  90                  95

Ile Ala Ser Thr Pro Ala Leu Arg Thr Pro Met Phe Val Leu Val Gly
                100                 105                 110

Ser Leu Ala Thr Ala Asp Leu Leu Ala Gly Cys Gly Leu Ile Leu His
                115                 120                 125

Phe Val Phe Gln Tyr Leu Val Pro Ser Glu Thr Val Ser Leu Leu Thr
        130                 135                 140

Val Gly Phe Leu Val Ala Ser Phe Ala Ser Val Ser Ser Leu Leu
145                 150                 155                 160

Ala Ile Thr Val Asp Arg Tyr Leu Ser Leu Tyr Asn Ala Leu Thr Tyr
                165                 170                 175
```

```
Tyr Ser Arg Arg Thr Leu Leu Gly Val His Leu Leu Ala Ala Thr
            180                 185                 190

Trp Thr Val Ser Leu Gly Leu Gly Leu Leu Pro Val Leu Gly Trp Asn
        195                 200                 205

Cys Leu Ala Glu Arg Ala Ala Cys Ser Val Val Arg Pro Leu Ala Arg
        210                 215                 220

Ser His Val Ala Leu Leu Ser Ala Ala Phe Phe Met Val Phe Gly Ile
225                 230                 235                 240

Met Leu His Leu Tyr Val Arg Ile Cys Gln Val Val Trp Arg His Ala
                245                 250                 255

His Gln Ile Ala Leu Gln Gln His Cys Leu Ala Pro Pro His Leu Ala
            260                 265                 270

Ala Thr Arg Lys Gly Val Gly Thr Leu Ala Val Val Leu Gly Thr Phe
                275                 280                 285

Gly Ala Ser Trp Leu Pro Phe Ala Ile Tyr Cys Val Val Gly Ser His
        290                 295                 300

Glu Asp Pro Ala Val Tyr Thr Tyr Ala Thr Leu Leu Pro Ala Thr Tyr
305                 310                 315                 320

Asn Ser Met Ile Asn Pro Ile Ile Tyr Ala Phe Arg Asn Gln Glu Ile
                325                 330                 335

Gln Arg Ala Leu Trp Leu Leu Leu Cys Gly Cys Phe Gln Ser Lys Val
            340                 345                 350

Pro Phe Arg Ser Arg Ser Pro Ser Glu Val
            355                 360

<210> SEQ ID NO 6
<211> LENGTH: 334
<212> TYPE: PRT
<213> ORGANISM: Homo sapiens

<400> SEQUENCE: 6

Met Asn Glu Asp Leu Lys Val Asn Leu Ser Gly Leu Pro Arg Asp Tyr
1               5                   10                  15

Leu Asp Ala Ala Ala Glu Asn Ile Ser Ala Ala Val Ser Ser Arg
                20                  25                  30

Val Pro Ala Val Glu Pro Glu Pro Leu Val Val Asn Pro Trp Asp
            35                  40                  45

Ile Val Leu Cys Thr Ser Gly Thr Leu Ile Ser Cys Glu Asn Ala Ile
        50                  55                  60

Val Val Leu Ile Ile Phe His Asn Pro Ser Leu Arg Ala Pro Met Phe
65                  70                  75                  80

Leu Leu Ile Gly Ser Leu Ala Leu Ala Asp Leu Leu Ala Gly Ile Gly
                85                  90                  95

Leu Ile Thr Asn Phe Val Phe Ala Tyr Leu Leu Gln Ser Glu Ala Thr
            100                 105                 110

Lys Leu Val Thr Ile Gly Leu Ile Val Ala Ser Phe Ser Ala Ser Val
        115                 120                 125

Cys Ser Leu Leu Ala Ile Thr Val Asp Arg Tyr Leu Ser Leu Tyr Tyr
    130                 135                 140

Ala Leu Thr Tyr His Ser Glu Arg Thr Val Thr Phe Thr Tyr Val Met
145                 150                 155                 160

Leu Val Met Leu Trp Gly Thr Ser Ile Cys Leu Gly Leu Leu Pro Val
                165                 170                 175

Met Gly Trp Asn Cys Leu Arg Asp Glu Ser Thr Cys Ser Val Val Arg
```

-continued

```
                    180                 185                 190
Pro Leu Thr Lys Asn Asn Ala Ala Ile Leu Ser Val Ser Phe Leu Phe
            195                 200                 205
Met Phe Ala Leu Met Leu Gln Leu Tyr Ile Gln Ile Cys Lys Ile Val
210                 215                 220
Met Arg His Ala His Gln Ile Ala Leu Gln His His Phe Leu Ala Thr
225                 230                 235                 240
Ser His Tyr Val Thr Thr Arg Lys Gly Val Ser Thr Leu Ala Ile Ile
                245                 250                 255
Leu Gly Thr Phe Ala Ala Cys Trp Met Pro Phe Thr Leu Tyr Ser Leu
            260                 265                 270
Ile Ala Asp Tyr Thr Tyr Pro Ser Ile Tyr Thr Tyr Ala Thr Leu Leu
        275                 280                 285
Pro Ala Thr Tyr Asn Ser Ile Ile Asn Pro Val Ile Tyr Ala Phe Arg
    290                 295                 300
Asn Gln Glu Ile Gln Lys Ala Leu Cys Leu Ile Cys Cys Gly Cys Ile
305                 310                 315                 320
Pro Ser Ser Leu Ala Gln Arg Ala Arg Ser Pro Ser Asp Val
                325                 330
```

<210> SEQ ID NO 7
<211> LENGTH: 21
<212> TYPE: DNA
<213> ORGANISM: Homo sapiens

<400> SEQUENCE: 7
tgggatgtgg tgctctgcat c        21

<210> SEQ ID NO 8
<211> LENGTH: 21
<212> TYPE: DNA
<213> ORGANISM: Homo sapiens

<400> SEQUENCE: 8
ggatgtggtg ctctgcatct c        21

<210> SEQ ID NO 9
<211> LENGTH: 21
<212> TYPE: DNA
<213> ORGANISM: Homo sapiens

<400> SEQUENCE: 9
aatgcgctag tggtggccat c        21

<210> SEQ ID NO 10
<211> LENGTH: 21
<212> TYPE: DNA
<213> ORGANISM: Homo sapiens

<400> SEQUENCE: 10
gtcctgcact ttgctgctgt c        21

<210> SEQ ID NO 11
<211> LENGTH: 21
<212> TYPE: DNA
<213> ORGANISM: Homo sapiens

<400> SEQUENCE: 11
ctgcactttg ctgctgtctt c        21

```
<210> SEQ ID NO 12
<211> LENGTH: 21
<212> TYPE: DNA
<213> ORGANISM: Homo sapiens

<400> SEQUENCE: 12
cactttgctg ctgtcttctg c                                              21

<210> SEQ ID NO 13
<211> LENGTH: 21
<212> TYPE: DNA
<213> ORGANISM: Homo sapiens

<400> SEQUENCE: 13
tttgctgctg tcttctgcat c                                              21

<210> SEQ ID NO 14
<211> LENGTH: 21
<212> TYPE: DNA
<213> ORGANISM: Homo sapiens

<400> SEQUENCE: 14
tgctgtcttc tgcatcggct c                                              21

<210> SEQ ID NO 15
<211> LENGTH: 21
<212> TYPE: DNA
<213> ORGANISM: Homo sapiens

<400> SEQUENCE: 15
tgtcttctgc atcggctcag c                                              21

<210> SEQ ID NO 16
<211> LENGTH: 21
<212> TYPE: DNA
<213> ORGANISM: Homo sapiens

<400> SEQUENCE: 16
cgtgctggca atggccttta c                                              21

<210> SEQ ID NO 17
<211> LENGTH: 21
<212> TYPE: DNA
<213> ORGANISM: Homo sapiens

<400> SEQUENCE: 17
gtgctggcaa tggcctttac c                                              21

<210> SEQ ID NO 18
<211> LENGTH: 21
<212> TYPE: DNA
<213> ORGANISM: Homo sapiens

<400> SEQUENCE: 18
atggccttta ccgccagcat c                                              21

<210> SEQ ID NO 19
<211> LENGTH: 21
<212> TYPE: DNA
<213> ORGANISM: Homo sapiens

<400> SEQUENCE: 19
atcggcagtc tactggccat c                                              21
```

```
<210> SEQ ID NO 20
<211> LENGTH: 21
<212> TYPE: DNA
<213> ORGANISM: Homo sapiens

<400> SEQUENCE: 20
agtctactgg ccatcactgt c                                              21

<210> SEQ ID NO 21
<211> LENGTH: 21
<212> TYPE: DNA
<213> ORGANISM: Homo sapiens

<400> SEQUENCE: 21
ctactggcca tcactgtcga c                                              21

<210> SEQ ID NO 22
<211> LENGTH: 21
<212> TYPE: DNA
<213> ORGANISM: Homo sapiens

<400> SEQUENCE: 22
tactggccat cactgtcgac c                                              21

<210> SEQ ID NO 23
<211> LENGTH: 21
<212> TYPE: DNA
<213> ORGANISM: Homo sapiens

<400> SEQUENCE: 23
cactgtcgac cgctaccttt c                                              21

<210> SEQ ID NO 24
<211> LENGTH: 21
<212> TYPE: DNA
<213> ORGANISM: Homo sapiens

<400> SEQUENCE: 24
ctgtcgaccg ctacctttct c                                              21

<210> SEQ ID NO 25
<211> LENGTH: 21
<212> TYPE: DNA
<213> ORGANISM: Homo sapiens

<400> SEQUENCE: 25
gaccgctacc tttctctgta c                                              21

<210> SEQ ID NO 26
<211> LENGTH: 21
<212> TYPE: DNA
<213> ORGANISM: Homo sapiens

<400> SEQUENCE: 26
ctacctttct ctgtacaatg c                                              21

<210> SEQ ID NO 27
<211> LENGTH: 21
<212> TYPE: DNA
<213> ORGANISM: Homo sapiens

<400> SEQUENCE: 27
```
tacctttctc tgtacaatgc c                                             21

<210> SEQ ID NO 28
<211> LENGTH: 21
<212> TYPE: DNA
<213> ORGANISM: Homo sapiens

<400> SEQUENCE: 28
acctttctct gtacaatgcc c                                             21

<210> SEQ ID NO 29
<211> LENGTH: 21
<212> TYPE: DNA
<213> ORGANISM: Homo sapiens

<400> SEQUENCE: 29
ctttctctgt acaatgccct c                                             21

<210> SEQ ID NO 30
<211> LENGTH: 21
<212> TYPE: DNA
<213> ORGANISM: Homo sapiens

<400> SEQUENCE: 30
ttctctgtac aatgccctca c                                             21

<210> SEQ ID NO 31
<211> LENGTH: 21
<212> TYPE: DNA
<213> ORGANISM: Homo sapiens

<400> SEQUENCE: 31
tctctgtaca atgccctcac c                                             21

<210> SEQ ID NO 32
<211> LENGTH: 21
<212> TYPE: DNA
<213> ORGANISM: Homo sapiens

<400> SEQUENCE: 32
ctgtacaatg ccctcaccta c                                             21

<210> SEQ ID NO 33
<211> LENGTH: 21
<212> TYPE: DNA
<213> ORGANISM: Homo sapiens

<400> SEQUENCE: 33
caatgccctc acctactatt c                                             21

<210> SEQ ID NO 34
<211> LENGTH: 21
<212> TYPE: DNA
<213> ORGANISM: Homo sapiens

<400> SEQUENCE: 34
cctcacctac tattcagaga c                                             21

<210> SEQ ID NO 35
<211> LENGTH: 21
<212> TYPE: DNA
<213> ORGANISM: Homo sapiens

<400> SEQUENCE: 35

```
cccctactat tcagagacaa c                                               21

<210> SEQ ID NO 36
<211> LENGTH: 21
<212> TYPE: DNA
<213> ORGANISM: Homo sapiens

<400> SEQUENCE: 36
ctattcagag acaacagtga c                                               21

<210> SEQ ID NO 37
<211> LENGTH: 21
<212> TYPE: DNA
<213> ORGANISM: Homo sapiens

<400> SEQUENCE: 37
attcagagac aacagtgaca c                                               21

<210> SEQ ID NO 38
<211> LENGTH: 21
<212> TYPE: DNA
<213> ORGANISM: Homo sapiens

<400> SEQUENCE: 38
agagacaaca gtgacacgga c                                               21

<210> SEQ ID NO 39
<211> LENGTH: 21
<212> TYPE: DNA
<213> ORGANISM: Homo sapiens

<400> SEQUENCE: 39
gagacaacag tgacacggac c                                               21

<210> SEQ ID NO 40
<211> LENGTH: 21
<212> TYPE: DNA
<213> ORGANISM: Homo sapiens

<400> SEQUENCE: 40
tgacacggac ctatgtgatg c                                               21

<210> SEQ ID NO 41
<211> LENGTH: 21
<212> TYPE: DNA
<213> ORGANISM: Homo sapiens

<400> SEQUENCE: 41
acggacctat gtgatgctgg c                                               21

<210> SEQ ID NO 42
<211> LENGTH: 21
<212> TYPE: DNA
<213> ORGANISM: Homo sapiens

<400> SEQUENCE: 42
ccacatgtgg cgtggtttat c                                               21

<210> SEQ ID NO 43
<211> LENGTH: 21
<212> TYPE: DNA
<213> ORGANISM: Homo sapiens
```

-continued

<400> SEQUENCE: 43
cacatgtggc gtggtttatc c                                         21

<210> SEQ ID NO 44
<211> LENGTH: 21
<212> TYPE: DNA
<213> ORGANISM: Homo sapiens

<400> SEQUENCE: 44
catgtggcgt ggtttatcca c                                         21

<210> SEQ ID NO 45
<211> LENGTH: 21
<212> TYPE: DNA
<213> ORGANISM: Homo sapiens

<400> SEQUENCE: 45
tgtggcgtgg tttatccact c                                         21

<210> SEQ ID NO 46
<211> LENGTH: 21
<212> TYPE: DNA
<213> ORGANISM: Homo sapiens

<400> SEQUENCE: 46
tggcgtggtt tatccactct c                                         21

<210> SEQ ID NO 47
<211> LENGTH: 21
<212> TYPE: DNA
<213> ORGANISM: Homo sapiens

<400> SEQUENCE: 47
ggcgtggttt atccactctc c                                         21

<210> SEQ ID NO 48
<211> LENGTH: 21
<212> TYPE: DNA
<213> ORGANISM: Homo sapiens

<400> SEQUENCE: 48
gtttatccac tctccaagaa c                                         21

<210> SEQ ID NO 49
<211> LENGTH: 21
<212> TYPE: DNA
<213> ORGANISM: Homo sapiens

<400> SEQUENCE: 49
tttatccact ctccaagaac c                                         21

<210> SEQ ID NO 50
<211> LENGTH: 21
<212> TYPE: DNA
<213> ORGANISM: Homo sapiens

<400> SEQUENCE: 50
atccactctc caagaaccat c                                         21

<210> SEQ ID NO 51
<211> LENGTH: 21
<212> TYPE: DNA
<213> ORGANISM: Homo sapiens -continued

<400> SEQUENCE: 51
ccaagaacca tctggtagtt c                                              21

<210> SEQ ID NO 52
<211> LENGTH: 21
<212> TYPE: DNA
<213> ORGANISM: Homo sapiens

<400> SEQUENCE: 52
gaaccatctg gtagttctgg c                                              21

<210> SEQ ID NO 53
<211> LENGTH: 21
<212> TYPE: DNA
<213> ORGANISM: Homo sapiens

<400> SEQUENCE: 53
aaccatctgg tagttctggc c                                              21

<210> SEQ ID NO 54
<211> LENGTH: 21
<212> TYPE: DNA
<213> ORGANISM: Homo sapiens

<400> SEQUENCE: 54
tctggtagtt ctggccattg c                                              21

<210> SEQ ID NO 55
<211> LENGTH: 21
<212> TYPE: DNA
<213> ORGANISM: Homo sapiens

<400> SEQUENCE: 55
ctggtagttc tggccattgc c                                              21

<210> SEQ ID NO 56
<211> LENGTH: 21
<212> TYPE: DNA
<213> ORGANISM: Homo sapiens

<400> SEQUENCE: 56
gtagttctgg ccattgcctt c                                              21

<210> SEQ ID NO 57
<211> LENGTH: 21
<212> TYPE: DNA
<213> ORGANISM: Homo sapiens

<400> SEQUENCE: 57
gttctggcca ttgccttctt c                                              21

<210> SEQ ID NO 58
<211> LENGTH: 21
<212> TYPE: DNA
<213> ORGANISM: Homo sapiens

<400> SEQUENCE: 58
gccttcttca tggtgtttgg c                                              21

<210> SEQ ID NO 59
<211> LENGTH: 21
<212> TYPE: DNA

```
<213> ORGANISM: Homo sapiens

<400> SEQUENCE: 59
ttcttcatgg tgtttggcat c                                              21

<210> SEQ ID NO 60
<211> LENGTH: 21
<212> TYPE: DNA
<213> ORGANISM: Homo sapiens

<400> SEQUENCE: 60
tcatggtgtt tggcatcatg c                                              21

<210> SEQ ID NO 61
<211> LENGTH: 21
<212> TYPE: DNA
<213> ORGANISM: Homo sapiens

<400> SEQUENCE: 61
tggtgtttgg catcatgctg c                                              21

<210> SEQ ID NO 62
<211> LENGTH: 21
<212> TYPE: DNA
<213> ORGANISM: Homo sapiens

<400> SEQUENCE: 62
tgtttggcat catgctgcag c                                              21

<210> SEQ ID NO 63
<211> LENGTH: 21
<212> TYPE: DNA
<213> ORGANISM: Homo sapiens

<400> SEQUENCE: 63
tttggcatca tgctgcagct c                                              21

<210> SEQ ID NO 64
<211> LENGTH: 21
<212> TYPE: DNA
<213> ORGANISM: Homo sapiens

<400> SEQUENCE: 64
ggcatcatgc tgcagctcta c                                              21

<210> SEQ ID NO 65
<211> LENGTH: 21
<212> TYPE: DNA
<213> ORGANISM: Homo sapiens

<400> SEQUENCE: 65
catcatgctg cagctctacg c                                              21

<210> SEQ ID NO 66
<211> LENGTH: 21
<212> TYPE: DNA
<213> ORGANISM: Homo sapiens

<400> SEQUENCE: 66
atcatgctgc agctctacgc c                                              21

<210> SEQ ID NO 67
<211> LENGTH: 21
```

```
<212> TYPE: DNA
<213> ORGANISM: Homo sapiens

<400> SEQUENCE: 67
ctgcagctct acgcccaaat c                                              21

<210> SEQ ID NO 68
<211> LENGTH: 21
<212> TYPE: DNA
<213> ORGANISM: Homo sapiens

<400> SEQUENCE: 68
cagctctacg cccaaatctg c                                              21

<210> SEQ ID NO 69
<211> LENGTH: 21
<212> TYPE: DNA
<213> ORGANISM: Homo sapiens

<400> SEQUENCE: 69
agctctacgc ccaaatctgc c                                              21

<210> SEQ ID NO 70
<211> LENGTH: 21
<212> TYPE: DNA
<213> ORGANISM: Homo sapiens

<400> SEQUENCE: 70
tacgcccaaa tctgccgcat c                                              21

<210> SEQ ID NO 71
<211> LENGTH: 21
<212> TYPE: DNA
<213> ORGANISM: Homo sapiens

<400> SEQUENCE: 71
caaatctgcc gcatcgtctg c                                              21

<210> SEQ ID NO 72
<211> LENGTH: 21
<212> TYPE: DNA
<213> ORGANISM: Homo sapiens

<400> SEQUENCE: 72
aaatctgccg catcgtctgc c                                              21

<210> SEQ ID NO 73
<211> LENGTH: 21
<212> TYPE: DNA
<213> ORGANISM: Homo sapiens

<400> SEQUENCE: 73
atgcccagca gattgccctt c                                              21

<210> SEQ ID NO 74
<211> LENGTH: 21
<212> TYPE: DNA
<213> ORGANISM: Homo sapiens

<400> SEQUENCE: 74
tgctggttgc ccttcactgt c                                              21

<210> SEQ ID NO 75
```

```
<211> LENGTH: 21
<212> TYPE: DNA
<213> ORGANISM: Homo sapiens

<400> SEQUENCE: 75
tggttgccct tcactgtcta c                                              21

<210> SEQ ID NO 76
<211> LENGTH: 21
<212> TYPE: DNA
<213> ORGANISM: Homo sapiens

<400> SEQUENCE: 76
ttgcccttca ctgtctactg c                                              21

<210> SEQ ID NO 77
<211> LENGTH: 21
<212> TYPE: DNA
<213> ORGANISM: Homo sapiens

<400> SEQUENCE: 77
tgcccttcac tgtctactgc c                                              21

<210> SEQ ID NO 78
<211> LENGTH: 21
<212> TYPE: DNA
<213> ORGANISM: Homo sapiens

<400> SEQUENCE: 78
ccttcactgt ctactgcctg c                                              21

<210> SEQ ID NO 79
<211> LENGTH: 21
<212> TYPE: DNA
<213> ORGANISM: Homo sapiens

<400> SEQUENCE: 79
ccactctcca cctctctaca c                                              21

<210> SEQ ID NO 80
<211> LENGTH: 21
<212> TYPE: DNA
<213> ORGANISM: Homo sapiens

<400> SEQUENCE: 80
cactctccac ctctctacac c                                              21

<210> SEQ ID NO 81
<211> LENGTH: 21
<212> TYPE: DNA
<213> ORGANISM: Homo sapiens

<400> SEQUENCE: 81
ctccacctct ctacacctat c                                              21

<210> SEQ ID NO 82
<211> LENGTH: 21
<212> TYPE: DNA
<213> ORGANISM: Homo sapiens

<400> SEQUENCE: 82
acctctctac acctatctta c                                              21
```

<210> SEQ ID NO 83
<211> LENGTH: 21
<212> TYPE: DNA
<213> ORGANISM: Homo sapiens

<400> SEQUENCE: 83
cctctctaca cctatcttac c                                    21

<210> SEQ ID NO 84
<211> LENGTH: 21
<212> TYPE: DNA
<213> ORGANISM: Homo sapiens

<400> SEQUENCE: 84
tctacaccta tcttaccttg c                                    21

<210> SEQ ID NO 85
<211> LENGTH: 21
<212> TYPE: DNA
<213> ORGANISM: Homo sapiens

<400> SEQUENCE: 85
tacacctatc ttaccttgct c                                    21

<210> SEQ ID NO 86
<211> LENGTH: 21
<212> TYPE: DNA
<213> ORGANISM: Homo sapiens

<400> SEQUENCE: 86
acacctatct taccttgctc c                                    21

<210> SEQ ID NO 87
<211> LENGTH: 21
<212> TYPE: DNA
<213> ORGANISM: Homo sapiens

<400> SEQUENCE: 87
cacctatctt accttgctcc c                                    21

<210> SEQ ID NO 88
<211> LENGTH: 21
<212> TYPE: DNA
<213> ORGANISM: Homo sapiens

<400> SEQUENCE: 88
ctatcttacc ttgctccctg c                                    21

<210> SEQ ID NO 89
<211> LENGTH: 21
<212> TYPE: DNA
<213> ORGANISM: Homo sapiens

<400> SEQUENCE: 89
tatcttacct tgctccctgc c                                    21

<210> SEQ ID NO 90
<211> LENGTH: 21
<212> TYPE: DNA
<213> ORGANISM: Homo sapiens

<400> SEQUENCE: 90
tcttaccttg ctccctgcca c                                    21

```
<210> SEQ ID NO 91
<211> LENGTH: 21
<212> TYPE: DNA
<213> ORGANISM: Homo sapiens

<400> SEQUENCE: 91
ttgctccctg ccacctacaa c                                         21

<210> SEQ ID NO 92
<211> LENGTH: 21
<212> TYPE: DNA
<213> ORGANISM: Homo sapiens

<400> SEQUENCE: 92
gccacctaca actccatgat c                                         21

<210> SEQ ID NO 93
<211> LENGTH: 21
<212> TYPE: DNA
<213> ORGANISM: Homo sapiens

<400> SEQUENCE: 93
acctacaact ccatgatcaa c                                         21

<210> SEQ ID NO 94
<211> LENGTH: 21
<212> TYPE: DNA
<213> ORGANISM: Homo sapiens

<400> SEQUENCE: 94
cctacaactc catgatcaac c                                         21

<210> SEQ ID NO 95
<211> LENGTH: 21
<212> TYPE: DNA
<213> ORGANISM: Homo sapiens

<400> SEQUENCE: 95
ctacaactcc atgatcaacc c                                         21

<210> SEQ ID NO 96
<211> LENGTH: 21
<212> TYPE: DNA
<213> ORGANISM: Homo sapiens

<400> SEQUENCE: 96
aactccatga tcaaccctat c                                         21

<210> SEQ ID NO 97
<211> LENGTH: 21
<212> TYPE: DNA
<213> ORGANISM: Homo sapiens

<400> SEQUENCE: 97
tccatgatca accctatcat c                                         21

<210> SEQ ID NO 98
<211> LENGTH: 21
<212> TYPE: DNA
<213> ORGANISM: Homo sapiens

<400> SEQUENCE: 98
gatcaaccct atcatctacg c                                         21
```

<210> SEQ ID NO 99
<211> LENGTH: 21
<212> TYPE: DNA
<213> ORGANISM: Homo sapiens

<400> SEQUENCE: 99 atcaaccta tcatctacgc c                                      21

<210> SEQ ID NO 100
<211> LENGTH: 21
<212> TYPE: DNA
<213> ORGANISM: Homo sapiens

<400> SEQUENCE: 100
aaccctatca tctacgcctt c                                     21

<210> SEQ ID NO 101
<211> LENGTH: 21
<212> TYPE: DNA
<213> ORGANISM: Homo sapiens

<400> SEQUENCE: 101
accctatcat ctacgccttc c                                     21

<210> SEQ ID NO 102
<211> LENGTH: 21
<212> TYPE: DNA
<213> ORGANISM: Homo sapiens

<400> SEQUENCE: 102
cctatcatct acgccttccg c                                     21

<210> SEQ ID NO 103
<211> LENGTH: 21
<212> TYPE: DNA
<213> ORGANISM: Homo sapiens

<400> SEQUENCE: 103
atcatctacg ccttccgcaa c                                     21

<210> SEQ ID NO 104
<211> LENGTH: 21
<212> TYPE: DNA
<213> ORGANISM: Homo sapiens

<400> SEQUENCE: 104
tcatctacgc cttccgcaac c                                     21

<210> SEQ ID NO 105
<211> LENGTH: 21
<212> TYPE: DNA
<213> ORGANISM: Homo sapiens

<400> SEQUENCE: 105
accaggatgt gcagaaagtg c                                     21

<210> SEQ ID NO 106
<211> LENGTH: 21
<212> TYPE: DNA
<213> ORGANISM: Homo sapiens

<400> SEQUENCE: 106

```
tgtgcagaaa gtgctgtggg c                                              21
```

<210> SEQ ID NO 107
<211> LENGTH: 21
<212> TYPE: DNA
<213> ORGANISM: Homo sapiens

<400> SEQUENCE: 107

```
aaagtgctgt gggctgtctg c                                              21
```

<210> SEQ ID NO 108
<211> LENGTH: 21
<212> TYPE: DNA
<213> ORGANISM: Homo sapiens

<400> SEQUENCE: 108

```
gctgttcctc ttccaagatc c                                              21
```

<210> SEQ ID NO 109
<211> LENGTH: 21
<212> TYPE: DNA
<213> ORGANISM: Homo sapiens

<400> SEQUENCE: 109

```
gagctaatgg gtctctggag c                                              21
```

<210> SEQ ID NO 110
<211> LENGTH: 21
<212> TYPE: DNA
<213> ORGANISM: Homo sapiens

<400> SEQUENCE: 110

```
taatgggtct ctggagctgt c                                              21
```

<210> SEQ ID NO 111
<211> LENGTH: 21
<212> TYPE: DNA
<213> ORGANISM: Homo sapiens

<400> SEQUENCE: 111

```
aatgggtctc tggagctgtc c                                              21
```

<210> SEQ ID NO 112
<211> LENGTH: 21
<212> TYPE: DNA
<213> ORGANISM: Homo sapiens

<400> SEQUENCE: 112

```
atgttcgtgc tggtaggcag c                                              21
```

<210> SEQ ID NO 113
<211> LENGTH: 21
<212> TYPE: DNA
<213> ORGANISM: Homo sapiens

<400> SEQUENCE: 113

```
ctcatcttgc actttgtgtt c                                              21
```

<210> SEQ ID NO 114
<211> LENGTH: 21
<212> TYPE: DNA
<213> ORGANISM: Homo sapiens

<400> SEQUENCE: 114

```
tcatcttgca ctttgtgttc c                                              21

<210> SEQ ID NO 115
<211> LENGTH: 21
<212> TYPE: DNA
<213> ORGANISM: Homo sapiens

<400> SEQUENCE: 115
ttgcactttg tgttccagta c                                              21

<210> SEQ ID NO 116
<211> LENGTH: 21
<212> TYPE: DNA
<213> ORGANISM: Homo sapiens

<400> SEQUENCE: 116
ttgtgttcca gtacttggtg c                                              21

<210> SEQ ID NO 117
<211> LENGTH: 21
<212> TYPE: DNA
<213> ORGANISM: Homo sapiens

<400> SEQUENCE: 117
gttgttccag tacttggtgc c                                              21

<210> SEQ ID NO 118
<211> LENGTH: 21
<212> TYPE: DNA
<213> ORGANISM: Homo sapiens

<400> SEQUENCE: 118
gtgttccagt acttggtgcc c                                              21

<210> SEQ ID NO 119
<211> LENGTH: 21
<212> TYPE: DNA
<213> ORGANISM: Homo sapiens

<400> SEQUENCE: 119
gttccagtac ttggtgccct c                                              21

<210> SEQ ID NO 120
<211> LENGTH: 21
<212> TYPE: DNA
<213> ORGANISM: Homo sapiens

<400> SEQUENCE: 120
tcggagactg tgagtctgct c                                              21

<210> SEQ ID NO 121
<211> LENGTH: 21
<212> TYPE: DNA
<213> ORGANISM: Homo sapiens

<400> SEQUENCE: 121
ggagactgtg agtctgctca c                                              21

<210> SEQ ID NO 122
<211> LENGTH: 21
<212> TYPE: DNA
<213> ORGANISM: Homo sapiens
```

-continued

<400> SEQUENCE: 122
cgctacctgt ccctgtataa c                                              21

<210> SEQ ID NO 123
<211> LENGTH: 21
<212> TYPE: DNA
<213> ORGANISM: Homo sapiens

<400> SEQUENCE: 123
ctacctgtcc ctgtataacg c                                              21

<210> SEQ ID NO 124
<211> LENGTH: 21
<212> TYPE: DNA
<213> ORGANISM: Homo sapiens

<400> SEQUENCE: 124
acctgtccct gtataacgcg c                                              21

<210> SEQ ID NO 125
<211> LENGTH: 21
<212> TYPE: DNA
<213> ORGANISM: Homo sapiens

<400> SEQUENCE: 125
ctgtccctgt ataacgcgct c                                              21

<210> SEQ ID NO 126
<211> LENGTH: 21
<212> TYPE: DNA
<213> ORGANISM: Homo sapiens

<400> SEQUENCE: 126
gtccctgtat aacgcgctca c                                              21

<210> SEQ ID NO 127
<211> LENGTH: 21
<212> TYPE: DNA
<213> ORGANISM: Homo sapiens

<400> SEQUENCE: 127
tccctgtata acgcgctcac c                                              21

<210> SEQ ID NO 128
<211> LENGTH: 21
<212> TYPE: DNA
<213> ORGANISM: Homo sapiens

<400> SEQUENCE: 128
tataacgcgc tcacctatta c                                              21

<210> SEQ ID NO 129
<211> LENGTH: 21
<212> TYPE: DNA
<213> ORGANISM: Homo sapiens

<400> SEQUENCE: 129
taacgcgctc acctattact c                                              21

<210> SEQ ID NO 130
<211> LENGTH: 21
<212> TYPE: DNA
<213> ORGANISM: Homo sapiens

<400> SEQUENCE: 130
acgcgctcac ctattactcg c              21

<210> SEQ ID NO 131
<211> LENGTH: 21
<212> TYPE: DNA
<213> ORGANISM: Homo sapiens

<400> SEQUENCE: 131
gccgccttct tcatggtctt c              21

<210> SEQ ID NO 132
<211> LENGTH: 21
<212> TYPE: DNA
<213> ORGANISM: Homo sapiens

<400> SEQUENCE: 132
gccttcttca tggtcttcgg c              21

<210> SEQ ID NO 133
<211> LENGTH: 21
<212> TYPE: DNA
<213> ORGANISM: Homo sapiens

<400> SEQUENCE: 133
ttcttcatgg tcttcggcat c              21

<210> SEQ ID NO 134
<211> LENGTH: 21
<212> TYPE: DNA
<213> ORGANISM: Homo sapiens

<400> SEQUENCE: 134
tcatggtctt cggcatcatg c              21

<210> SEQ ID NO 135
<211> LENGTH: 21
<212> TYPE: DNA
<213> ORGANISM: Homo sapiens

<400> SEQUENCE: 135
tggtcttcgg catcatgctg c              21

<210> SEQ ID NO 136
<211> LENGTH: 21
<212> TYPE: DNA
<213> ORGANISM: Homo sapiens

<400> SEQUENCE: 136
gtcttcggca tcatgctgca c              21

<210> SEQ ID NO 137
<211> LENGTH: 21
<212> TYPE: DNA
<213> ORGANISM: Homo sapiens

<400> SEQUENCE: 137
tcttcggcat catgctgcac c              21

<210> SEQ ID NO 138
<211> LENGTH: 21
<212> TYPE: DNA

<213> ORGANISM: Homo sapiens

<400> SEQUENCE: 138
ggcatcatgc tgcacctgta c                                       21

<210> SEQ ID NO 139
<211> LENGTH: 21
<212> TYPE: DNA
<213> ORGANISM: Homo sapiens

<400> SEQUENCE: 139
tcatgctgca cctgtacgtg c                                       21

<210> SEQ ID NO 140
<211> LENGTH: 21
<212> TYPE: DNA
<213> ORGANISM: Homo sapiens

<400> SEQUENCE: 140
caccagaaag ggtgtgggta c                                       21

<210> SEQ ID NO 141
<211> LENGTH: 21
<212> TYPE: DNA
<213> ORGANISM: Homo sapiens

<400> SEQUENCE: 141
ccagaaaggg tgtgggtaca c                                       21

<210> SEQ ID NO 142
<211> LENGTH: 21
<212> TYPE: DNA
<213> ORGANISM: Homo sapiens

<400> SEQUENCE: 142
aaagggtgtg ggtacactgg c                                       21

<210> SEQ ID NO 143
<211> LENGTH: 21
<212> TYPE: DNA
<213> ORGANISM: Homo sapiens

<400> SEQUENCE: 143
ctgcccttcg ccatctattg c                                       21

<210> SEQ ID NO 144
<211> LENGTH: 21
<212> TYPE: DNA
<213> ORGANISM: Homo sapiens

<400> SEQUENCE: 144
atctattgcg tggtgggcag c                                       21

<210> SEQ ID NO 145
<211> LENGTH: 21
<212> TYPE: DNA
<213> ORGANISM: Homo sapiens

<400> SEQUENCE: 145
tctacactta cgccaccctg c                                       21

<210> SEQ ID NO 146
<211> LENGTH: 21

```
<212> TYPE: DNA
<213> ORGANISM: Homo sapiens

<400> SEQUENCE: 146
cctacaactc catgatcaat c                                              21

<210> SEQ ID NO 147
<211> LENGTH: 21
<212> TYPE: DNA
<213> ORGANISM: Homo sapiens

<400> SEQUENCE: 147
ctacaactcc atgatcaatc c                                              21

<210> SEQ ID NO 148
<211> LENGTH: 21
<212> TYPE: DNA
<213> ORGANISM: Homo sapiens

<400> SEQUENCE: 148
tacaactcca tgatcaatcc c                                              21

<210> SEQ ID NO 149
<211> LENGTH: 21
<212> TYPE: DNA
<213> ORGANISM: Homo sapiens

<400> SEQUENCE: 149
aactccatga tcaatcccat c                                              21

<210> SEQ ID NO 150
<211> LENGTH: 21
<212> TYPE: DNA
<213> ORGANISM: Homo sapiens

<400> SEQUENCE: 150
tccatgatca atcccatcat c                                              21

<210> SEQ ID NO 151
<211> LENGTH: 21
<212> TYPE: DNA
<213> ORGANISM: Homo sapiens

<400> SEQUENCE: 151
gatcaatccc atcatctatg c                                              21

<210> SEQ ID NO 152
<211> LENGTH: 21
<212> TYPE: DNA
<213> ORGANISM: Homo sapiens

<400> SEQUENCE: 152
atcaatccca tcatctatgc c                                              21

<210> SEQ ID NO 153
<211> LENGTH: 21
<212> TYPE: DNA
<213> ORGANISM: Homo sapiens

<400> SEQUENCE: 153
aatcccatca tctatgcctt c                                              21

<210> SEQ ID NO 154
```

```
<211> LENGTH: 21
<212> TYPE: DNA
<213> ORGANISM: Homo sapiens

<400> SEQUENCE: 154
atcccatcat ctatgccttc c                                              21

<210> SEQ ID NO 155
<211> LENGTH: 21
<212> TYPE: DNA
<213> ORGANISM: Homo sapiens

<400> SEQUENCE: 155
cccatcatct atgccttccg c                                              21

<210> SEQ ID NO 156
<211> LENGTH: 21
<212> TYPE: DNA
<213> ORGANISM: Homo sapiens

<400> SEQUENCE: 156
atcatctatg ccttccgcaa c                                              21

<210> SEQ ID NO 157
<211> LENGTH: 21
<212> TYPE: DNA
<213> ORGANISM: Homo sapiens

<400> SEQUENCE: 157
tcatctatgc cttccgcaac c                                              21

<210> SEQ ID NO 158
<211> LENGTH: 21
<212> TYPE: DNA
<213> ORGANISM: Homo sapiens

<400> SEQUENCE: 158
ctcctgctct gtggctgttt c                                              21

<210> SEQ ID NO 159
<211> LENGTH: 21
<212> TYPE: DNA
<213> ORGANISM: Homo sapiens

<400> SEQUENCE: 159
tcctgctctg tggctgtttc c                                              21

<210> SEQ ID NO 160
<211> LENGTH: 21
<212> TYPE: DNA
<213> ORGANISM: Homo sapiens

<400> SEQUENCE: 160
gctctgtggc tgtttccagt c                                              21

<210> SEQ ID NO 161
<211> LENGTH: 21
<212> TYPE: DNA
<213> ORGANISM: Homo sapiens

<400> SEQUENCE: 161
ctctgtggct gtttccagtc c                                              21
```

```
<210> SEQ ID NO 162
<211> LENGTH: 21
<212> TYPE: DNA
<213> ORGANISM: Homo sapiens

<400> SEQUENCE: 162
gctgtttcca gtccaaagtg c                                              21

<210> SEQ ID NO 163
<211> LENGTH: 21
<212> TYPE: DNA
<213> ORGANISM: Homo sapiens

<400> SEQUENCE: 163
ctgtttccag tccaaagtgc c                                              21

<210> SEQ ID NO 164
<211> LENGTH: 21
<212> TYPE: DNA
<213> ORGANISM: Homo sapiens

<400> SEQUENCE: 164
tgtttccagt ccaaagtgcc c                                              21

<210> SEQ ID NO 165
<211> LENGTH: 21
<212> TYPE: DNA
<213> ORGANISM: Homo sapiens

<400> SEQUENCE: 165
tccagtccaa agtgcccttt c                                              21

<210> SEQ ID NO 166
<211> LENGTH: 21
<212> TYPE: DNA
<213> ORGANISM: Homo sapiens

<400> SEQUENCE: 166
gtccaaagtg ccctttcgtt c                                              21

<210> SEQ ID NO 167
<211> LENGTH: 21
<212> TYPE: DNA
<213> ORGANISM: Homo sapiens

<400> SEQUENCE: 167
tccaaagtgc cctttcgttc c                                              21

<210> SEQ ID NO 168
<211> LENGTH: 21
<212> TYPE: DNA
<213> ORGANISM: Homo sapiens

<400> SEQUENCE: 168
agtgcccttt cgttccaggt c                                              21

<210> SEQ ID NO 169
<211> LENGTH: 21
<212> TYPE: DNA
<213> ORGANISM: Homo sapiens

<400> SEQUENCE: 169
tgccctttcg ttccaggtct c                                              21
```

<210> SEQ ID NO 170
<211> LENGTH: 21
<212> TYPE: DNA
<213> ORGANISM: Homo sapiens

<400> SEQUENCE: 170
tttcgttcca ggtctcccag c                                              21

<210> SEQ ID NO 171
<211> LENGTH: 21
<212> TYPE: DNA
<213> ORGANISM: Homo sapiens

<400> SEQUENCE: 171
gagcctgagc tcgtagtcaa c                                              21

<210> SEQ ID NO 172
<211> LENGTH: 21
<212> TYPE: DNA
<213> ORGANISM: Homo sapiens

<400> SEQUENCE: 172
agcctgagct cgtagtcaac c                                              21

<210> SEQ ID NO 173
<211> LENGTH: 21
<212> TYPE: DNA
<213> ORGANISM: Homo sapiens

<400> SEQUENCE: 173
ctgggacatt gtcttgtgta c                                              21

<210> SEQ ID NO 174
<211> LENGTH: 21
<212> TYPE: DNA
<213> ORGANISM: Homo sapiens

<400> SEQUENCE: 174
tgggacattg tcttgtgtac c                                              21

<210> SEQ ID NO 175
<211> LENGTH: 21
<212> TYPE: DNA
<213> ORGANISM: Homo sapiens

<400> SEQUENCE: 175
ggacattgtc ttgtgtacct c                                              21

<210> SEQ ID NO 176
<211> LENGTH: 21
<212> TYPE: DNA
<213> ORGANISM: Homo sapiens

<400> SEQUENCE: 176
tgtcttgtgt acctcgggaa c                                              21

<210> SEQ ID NO 177
<211> LENGTH: 21
<212> TYPE: DNA
<213> ORGANISM: Homo sapiens

<400> SEQUENCE: 177
gtcttgtgta cctcgggaac c                                              21

<210> SEQ ID NO 178
<211> LENGTH: 21
<212> TYPE: DNA
<213> ORGANISM: Homo sapiens

<400> SEQUENCE: 178
tcttgtgtac ctcgggaacc c                                    21

<210> SEQ ID NO 179
<211> LENGTH: 21
<212> TYPE: DNA
<213> ORGANISM: Homo sapiens

<400> SEQUENCE: 179
ttgtgtacct cgggaaccct c                                    21

<210> SEQ ID NO 180
<211> LENGTH: 21
<212> TYPE: DNA
<213> ORGANISM: Homo sapiens

<400> SEQUENCE: 180
tgtacctcgg gaaccctcat c                                    21

<210> SEQ ID NO 181
<211> LENGTH: 21
<212> TYPE: DNA
<213> ORGANISM: Homo sapiens

<400> SEQUENCE: 181
tacctcggga accctcatct c                                    21

<210> SEQ ID NO 182
<211> LENGTH: 21
<212> TYPE: DNA
<213> ORGANISM: Homo sapiens

<400> SEQUENCE: 182
aatgccattg tggtccttat c                                    21

<210> SEQ ID NO 183
<211> LENGTH: 21
<212> TYPE: DNA
<213> ORGANISM: Homo sapiens

<400> SEQUENCE: 183
gccattgtgg tccttatcat c                                    21

<210> SEQ ID NO 184
<211> LENGTH: 21
<212> TYPE: DNA
<213> ORGANISM: Homo sapiens

<400> SEQUENCE: 184
ttgtggtcct tatcatcttc c                                    21

<210> SEQ ID NO 185
<211> LENGTH: 21
<212> TYPE: DNA
<213> ORGANISM: Homo sapiens

<400> SEQUENCE: 185

| | |
|---|---|
| gtggtcctta tcatcttcca c | 21 |

<210> SEQ ID NO 186
<211> LENGTH: 21
<212> TYPE: DNA
<213> ORGANISM: Homo sapiens

<400> SEQUENCE: 186

| | |
|---|---|
| gtccttatca tcttccacaa c | 21 |

<210> SEQ ID NO 187
<211> LENGTH: 21
<212> TYPE: DNA
<213> ORGANISM: Homo sapiens

<400> SEQUENCE: 187

| | |
|---|---|
| tccttatcat cttccacaac c | 21 |

<210> SEQ ID NO 188
<211> LENGTH: 21
<212> TYPE: DNA
<213> ORGANISM: Homo sapiens

<400> SEQUENCE: 188

| | |
|---|---|
| ccttatcatc ttccacaacc c | 21 |

<210> SEQ ID NO 189
<211> LENGTH: 21
<212> TYPE: DNA
<213> ORGANISM: Homo sapiens

<400> SEQUENCE: 189

| | |
|---|---|
| cccatgttcc tgctaatagg c | 21 |

<210> SEQ ID NO 190
<211> LENGTH: 21
<212> TYPE: DNA
<213> ORGANISM: Homo sapiens

<400> SEQUENCE: 190

| | |
|---|---|
| atgttcctgc taataggcag c | 21 |

<210> SEQ ID NO 191
<211> LENGTH: 21
<212> TYPE: DNA
<213> ORGANISM: Homo sapiens

<400> SEQUENCE: 191

| | |
|---|---|
| tgttcctgct aataggcagc c | 21 |

<210> SEQ ID NO 192
<211> LENGTH: 21
<212> TYPE: DNA
<213> ORGANISM: Homo sapiens

<400> SEQUENCE: 192

| | |
|---|---|
| tgctaatagg cagcctggct c | 21 |

<210> SEQ ID NO 193
<211> LENGTH: 21
<212> TYPE: DNA
<213> ORGANISM: Homo sapiens

<400> SEQUENCE: 193

```
aataggcagc ctggctcttg c                                           21

<210> SEQ ID NO 194
<211> LENGTH: 21
<212> TYPE: DNA
<213> ORGANISM: Homo sapiens

<400> SEQUENCE: 194
ctacctgctt cagtcagaag c                                           21

<210> SEQ ID NO 195
<211> LENGTH: 21
<212> TYPE: DNA
<213> ORGANISM: Homo sapiens

<400> SEQUENCE: 195
tacctgcttc agtcagaagc c                                           21

<210> SEQ ID NO 196
<211> LENGTH: 21
<212> TYPE: DNA
<213> ORGANISM: Homo sapiens

<400> SEQUENCE: 196
cctgcttcag tcagaagcca c                                           21

<210> SEQ ID NO 197
<211> LENGTH: 21
<212> TYPE: DNA
<213> ORGANISM: Homo sapiens

<400> SEQUENCE: 197
ctgcttcagt cagaagccac c                                           21

<210> SEQ ID NO 198
<211> LENGTH: 21
<212> TYPE: DNA
<213> ORGANISM: Homo sapiens

<400> SEQUENCE: 198
ttcagtcaga agccaccaag c                                           21

<210> SEQ ID NO 199
<211> LENGTH: 21
<212> TYPE: DNA
<213> ORGANISM: Homo sapiens

<400> SEQUENCE: 199
tcagaagcca ccaagctggt c                                           21

<210> SEQ ID NO 200
<211> LENGTH: 21
<212> TYPE: DNA
<213> ORGANISM: Homo sapiens

<400> SEQUENCE: 200
agaagccacc aagctggtca c                                           21

<210> SEQ ID NO 201
<211> LENGTH: 21
<212> TYPE: DNA
<213> ORGANISM: Homo sapiens
```

-continued

```
<400> SEQUENCE: 201
gtcacgatcg gcctcattgt c                                              21

<210> SEQ ID NO 202
<211> LENGTH: 21
<212> TYPE: DNA
<213> ORGANISM: Homo sapiens

<400> SEQUENCE: 202
ggcctcattg tcgcctcttt c                                              21

<210> SEQ ID NO 203
<211> LENGTH: 21
<212> TYPE: DNA
<213> ORGANISM: Homo sapiens

<400> SEQUENCE: 203
cctcattgtc gcctctttct c                                              21

<210> SEQ ID NO 204
<211> LENGTH: 21
<212> TYPE: DNA
<213> ORGANISM: Homo sapiens

<400> SEQUENCE: 204
cattgtcgcc tctttctctg c                                              21

<210> SEQ ID NO 205
<211> LENGTH: 21
<212> TYPE: DNA
<213> ORGANISM: Homo sapiens

<400> SEQUENCE: 205
attgtcgcct ctttctctgc c                                              21

<210> SEQ ID NO 206
<211> LENGTH: 21
<212> TYPE: DNA
<213> ORGANISM: Homo sapiens

<400> SEQUENCE: 206
tgtcgcctct ttctctgcct c                                              21

<210> SEQ ID NO 207
<211> LENGTH: 21
<212> TYPE: DNA
<213> ORGANISM: Homo sapiens

<400> SEQUENCE: 207
gcctctttct ctgcctctgt c                                              21

<210> SEQ ID NO 208
<211> LENGTH: 21
<212> TYPE: DNA
<213> ORGANISM: Homo sapiens

<400> SEQUENCE: 208
tctttctctg cctctgtctg c                                              21

<210> SEQ ID NO 209
<211> LENGTH: 21
<212> TYPE: DNA
<213> ORGANISM: Homo sapiens
```

```
<400> SEQUENCE: 209
ttctctgcct ctgtctgcag c                                              21

<210> SEQ ID NO 210
<211> LENGTH: 21
<212> TYPE: DNA
<213> ORGANISM: Homo sapiens

<400> SEQUENCE: 210
gtctgcagct tgctggctat c                                              21

<210> SEQ ID NO 211
<211> LENGTH: 21
<212> TYPE: DNA
<213> ORGANISM: Homo sapiens

<400> SEQUENCE: 211
ctgcagcttg ctggctatca c                                              21

<210> SEQ ID NO 212
<211> LENGTH: 21
<212> TYPE: DNA
<213> ORGANISM: Homo sapiens

<400> SEQUENCE: 212
ttgctggcta tcactgttga c                                              21

<210> SEQ ID NO 213
<211> LENGTH: 21
<212> TYPE: DNA
<213> ORGANISM: Homo sapiens

<400> SEQUENCE: 213
tgctggctat cactgttgac c                                              21

<210> SEQ ID NO 214
<211> LENGTH: 21
<212> TYPE: DNA
<213> ORGANISM: Homo sapiens

<400> SEQUENCE: 214
ctggctatca ctgttgaccg c                                              21

<210> SEQ ID NO 215
<211> LENGTH: 21
<212> TYPE: DNA
<213> ORGANISM: Homo sapiens

<400> SEQUENCE: 215
gctatcactg ttgaccgcta c                                              21

<210> SEQ ID NO 216
<211> LENGTH: 21
<212> TYPE: DNA
<213> ORGANISM: Homo sapiens

<400> SEQUENCE: 216
ctatcactgt tgaccgctac c                                              21

<210> SEQ ID NO 217
<211> LENGTH: 21
<212> TYPE: DNA
```

<213> ORGANISM: Homo sapiens

<400> SEQUENCE: 217
atcactgttg accgctacct c         21

<210> SEQ ID NO 218
<211> LENGTH: 21
<212> TYPE: DNA
<213> ORGANISM: Homo sapiens

<400> SEQUENCE: 218
cactgttgac cgctacctct c         21

<210> SEQ ID NO 219
<211> LENGTH: 21
<212> TYPE: DNA
<213> ORGANISM: Homo sapiens

<400> SEQUENCE: 219
ctgttgaccg ctacctctca c         21

<210> SEQ ID NO 220
<211> LENGTH: 21
<212> TYPE: DNA
<213> ORGANISM: Homo sapiens

<400> SEQUENCE: 220
gaccgctacc tctcactgta c         21

<210> SEQ ID NO 221
<211> LENGTH: 21
<212> TYPE: DNA
<213> ORGANISM: Homo sapiens

<400> SEQUENCE: 221
cgctacctct cactgtacta c         21

<210> SEQ ID NO 222
<211> LENGTH: 21
<212> TYPE: DNA
<213> ORGANISM: Homo sapiens

<400> SEQUENCE: 222
ctacctctca ctgtactacg c         21

<210> SEQ ID NO 223
<211> LENGTH: 21
<212> TYPE: DNA
<213> ORGANISM: Homo sapiens

<400> SEQUENCE: 223
acctctcact gtactacgct c         21

<210> SEQ ID NO 224
<211> LENGTH: 21
<212> TYPE: DNA
<213> ORGANISM: Homo sapiens

<400> SEQUENCE: 224
ctcactgtac tacgctctga c         21

<210> SEQ ID NO 225
<211> LENGTH: 21

```
<212> TYPE: DNA
<213> ORGANISM: Homo sapiens

<400> SEQUENCE: 225
ctgtactacg ctctgacgta c                                              21

<210> SEQ ID NO 226
<211> LENGTH: 21
<212> TYPE: DNA
<213> ORGANISM: Homo sapiens

<400> SEQUENCE: 226
tgtactacgc tctgacgtac c                                              21

<210> SEQ ID NO 227
<211> LENGTH: 21
<212> TYPE: DNA
<213> ORGANISM: Homo sapiens

<400> SEQUENCE: 227
ctacgctctg acgtaccatt c                                              21

<210> SEQ ID NO 228
<211> LENGTH: 21
<212> TYPE: DNA
<213> ORGANISM: Homo sapiens

<400> SEQUENCE: 228
gacgtaccat tcggagagga c                                              21

<210> SEQ ID NO 229
<211> LENGTH: 21
<212> TYPE: DNA
<213> ORGANISM: Homo sapiens

<400> SEQUENCE: 229
taccattcgg agaggacggt c                                              21

<210> SEQ ID NO 230
<211> LENGTH: 21
<212> TYPE: DNA
<213> ORGANISM: Homo sapiens

<400> SEQUENCE: 230
ggagaggacg gtcacgttta c                                              21

<210> SEQ ID NO 231
<211> LENGTH: 21
<212> TYPE: DNA
<213> ORGANISM: Homo sapiens

<400> SEQUENCE: 231
gagaggacgg tcacgtttac c                                              21

<210> SEQ ID NO 232
<211> LENGTH: 21
<212> TYPE: DNA
<213> ORGANISM: Homo sapiens

<400> SEQUENCE: 232
acggtcacgt ttacctatgt c                                              21

<210> SEQ ID NO 233
```

```
<211> LENGTH: 21
<212> TYPE: DNA
<213> ORGANISM: Homo sapiens

<400> SEQUENCE: 233
tcacgtttac ctatgtcatg c                                              21

<210> SEQ ID NO 234
<211> LENGTH: 21
<212> TYPE: DNA
<213> ORGANISM: Homo sapiens

<400> SEQUENCE: 234
acgtttacct atgtcatgct c                                              21

<210> SEQ ID NO 235
<211> LENGTH: 21
<212> TYPE: DNA
<213> ORGANISM: Homo sapiens

<400> SEQUENCE: 235
tttacctatg tcatgctcgt c                                              21

<210> SEQ ID NO 236
<211> LENGTH: 21
<212> TYPE: DNA
<213> ORGANISM: Homo sapiens

<400> SEQUENCE: 236
cctatgtcat gctcgtcatg c                                              21

<210> SEQ ID NO 237
<211> LENGTH: 21
<212> TYPE: DNA
<213> ORGANISM: Homo sapiens

<400> SEQUENCE: 237
tatgtcatgc tcgtcatgct c                                              21

<210> SEQ ID NO 238
<211> LENGTH: 21
<212> TYPE: DNA
<213> ORGANISM: Homo sapiens

<400> SEQUENCE: 238
gtcagaccgc tcaccaagaa c                                              21

<210> SEQ ID NO 239
<211> LENGTH: 21
<212> TYPE: DNA
<213> ORGANISM: Homo sapiens

<400> SEQUENCE: 239
agaccgctca ccaagaacaa c                                              21

<210> SEQ ID NO 240
<211> LENGTH: 21
<212> TYPE: DNA
<213> ORGANISM: Homo sapiens

<400> SEQUENCE: 240
accgctcacc aagaacaacg c                                              21
```

```
<210> SEQ ID NO 241
<211> LENGTH: 21
<212> TYPE: DNA
<213> ORGANISM: Homo sapiens

<400> SEQUENCE: 241
accaagaaca acgcggccat c                                              21

<210> SEQ ID NO 242
<211> LENGTH: 21
<212> TYPE: DNA
<213> ORGANISM: Homo sapiens

<400> SEQUENCE: 242
aagaacaacg cggccatcct c                                              21

<210> SEQ ID NO 243
<211> LENGTH: 21
<212> TYPE: DNA
<213> ORGANISM: Homo sapiens

<400> SEQUENCE: 243
atcctctcgg tgtccttcct c                                              21

<210> SEQ ID NO 244
<211> LENGTH: 21
<212> TYPE: DNA
<213> ORGANISM: Homo sapiens

<400> SEQUENCE: 244
ctctcggtgt ccttcctctt c                                              21

<210> SEQ ID NO 245
<211> LENGTH: 21
<212> TYPE: DNA
<213> ORGANISM: Homo sapiens

<400> SEQUENCE: 245
gtccttcctc ttcatgtttg c                                              21

<210> SEQ ID NO 246
<211> LENGTH: 21
<212> TYPE: DNA
<213> ORGANISM: Homo sapiens

<400> SEQUENCE: 246
ccttcctctt catgtttgcg c                                              21

<210> SEQ ID NO 247
<211> LENGTH: 21
<212> TYPE: DNA
<213> ORGANISM: Homo sapiens

<400> SEQUENCE: 247
ttcctcttca tgtttgcgct c                                              21

<210> SEQ ID NO 248
<211> LENGTH: 21
<212> TYPE: DNA
<213> ORGANISM: Homo sapiens

<400> SEQUENCE: 248
tcttcatgtt tgcgctcatg c                                              21
```

```
<210> SEQ ID NO 249
<211> LENGTH: 21
<212> TYPE: DNA
<213> ORGANISM: Homo sapiens

<400> SEQUENCE: 249
tcatgtttgc gctcatgctt c                                              21

<210> SEQ ID NO 250
<211> LENGTH: 21
<212> TYPE: DNA
<213> ORGANISM: Homo sapiens

<400> SEQUENCE: 250
tgtttgcgct catgcttcag c                                              21

<210> SEQ ID NO 251
<211> LENGTH: 21
<212> TYPE: DNA
<213> ORGANISM: Homo sapiens

<400> SEQUENCE: 251
tttgcgctca tgcttcagct c                                              21

<210> SEQ ID NO 252
<211> LENGTH: 21
<212> TYPE: DNA
<213> ORGANISM: Homo sapiens

<400> SEQUENCE: 252
gcgctcatgc ttcagctcta c                                              21

<210> SEQ ID NO 253
<211> LENGTH: 21
<212> TYPE: DNA
<213> ORGANISM: Homo sapiens

<400> SEQUENCE: 253
ctcatgcttc agctctacat c                                              21

<210> SEQ ID NO 254
<211> LENGTH: 21
<212> TYPE: DNA
<213> ORGANISM: Homo sapiens

<400> SEQUENCE: 254
tcatgcttca gctctacatc c                                              21

<210> SEQ ID NO 255
<211> LENGTH: 21
<212> TYPE: DNA
<213> ORGANISM: Homo sapiens

<400> SEQUENCE: 255
cttcagctct acatccagat c                                              21

<210> SEQ ID NO 256
<211> LENGTH: 21
<212> TYPE: DNA
<213> ORGANISM: Homo sapiens

<400> SEQUENCE: 256
tctgtaagat tgtgatgagg c                                              21
```

<210> SEQ ID NO 257
<211> LENGTH: 21
<212> TYPE: DNA
<213> ORGANISM: Homo sapiens

<400> SEQUENCE: 257
tgtaagattg tgatgaggca c                                             21

<210> SEQ ID NO 258
<211> LENGTH: 21
<212> TYPE: DNA
<213> ORGANISM: Homo sapiens

<400> SEQUENCE: 258
taagattgtg atgaggcacg c                                             21

<210> SEQ ID NO 259
<211> LENGTH: 21
<212> TYPE: DNA
<213> ORGANISM: Homo sapiens

<400> SEQUENCE: 259
aagattgtga tgaggcacgc c                                             21

<210> SEQ ID NO 260
<211> LENGTH: 21
<212> TYPE: DNA
<213> ORGANISM: Homo sapiens

<400> SEQUENCE: 260
agattgtgat gaggcacgcc c                                             21

<210> SEQ ID NO 261
<211> LENGTH: 21
<212> TYPE: DNA
<213> ORGANISM: Homo sapiens

<400> SEQUENCE: 261
ttgtgatgag gcacgcccat c                                             21

<210> SEQ ID NO 262
<211> LENGTH: 21
<212> TYPE: DNA
<213> ORGANISM: Homo sapiens

<400> SEQUENCE: 262
catcagatag ccctgcagca c                                             21

<210> SEQ ID NO 263
<211> LENGTH: 21
<212> TYPE: DNA
<213> ORGANISM: Homo sapiens

<400> SEQUENCE: 263
atcagatagc cctgcagcac c                                             21

<210> SEQ ID NO 264
<211> LENGTH: 21
<212> TYPE: DNA
<213> ORGANISM: Homo sapiens

<400> SEQUENCE: 264
atagccctgc agcaccactt c     21

<210> SEQ ID NO 265
<211> LENGTH: 21
<212> TYPE: DNA
<213> ORGANISM: Homo sapiens

<400> SEQUENCE: 265
cacgtcgcac tatgtgacca c     21

<210> SEQ ID NO 266
<211> LENGTH: 21
<212> TYPE: DNA
<213> ORGANISM: Homo sapiens

<400> SEQUENCE: 266
acgtcgcact atgtgaccac c     21

<210> SEQ ID NO 267
<211> LENGTH: 21
<212> TYPE: DNA
<213> ORGANISM: Homo sapiens

<400> SEQUENCE: 267
gtctccaccc tggctatcat c     21

<210> SEQ ID NO 268
<211> LENGTH: 21
<212> TYPE: DNA
<213> ORGANISM: Homo sapiens

<400> SEQUENCE: 268
tctccaccct ggctatcatc c     21

<210> SEQ ID NO 269
<211> LENGTH: 21
<212> TYPE: DNA
<213> ORGANISM: Homo sapiens

<400> SEQUENCE: 269
cgtttgctgc ttgctggatg c     21

<210> SEQ ID NO 270
<211> LENGTH: 21
<212> TYPE: DNA
<213> ORGANISM: Homo sapiens

<400> SEQUENCE: 270
gtttgctgct tgctggatgc c     21

<210> SEQ ID NO 271
<211> LENGTH: 21
<212> TYPE: DNA
<213> ORGANISM: Homo sapiens

<400> SEQUENCE: 271
gctgcttgct ggatgccttt c     21

<210> SEQ ID NO 272
<211> LENGTH: 21
<212> TYPE: DNA
<213> ORGANISM: Homo sapiens

<400> SEQUENCE: 272

```
gcttgctgga tgcctttcac c                                              21

<210> SEQ ID NO 273
<211> LENGTH: 21
<212> TYPE: DNA
<213> ORGANISM: Homo sapiens

<400> SEQUENCE: 273
tccttgatag cggattacac c                                              21

<210> SEQ ID NO 274
<211> LENGTH: 21
<212> TYPE: DNA
<213> ORGANISM: Homo sapiens

<400> SEQUENCE: 274
ccctccatct atacctacgc c                                              21

<210> SEQ ID NO 275
<211> LENGTH: 21
<212> TYPE: DNA
<213> ORGANISM: Homo sapiens

<400> SEQUENCE: 275
tccatctata cctacgccac c                                              21

<210> SEQ ID NO 276
<211> LENGTH: 21
<212> TYPE: DNA
<213> ORGANISM: Homo sapiens

<400> SEQUENCE: 276
ccatctatac ctacgccacc c                                              21

<210> SEQ ID NO 277
<211> LENGTH: 21
<212> TYPE: DNA
<213> ORGANISM: Homo sapiens

<400> SEQUENCE: 277
tctataccta cgccaccctc c                                              21

<210> SEQ ID NO 278
<211> LENGTH: 21
<212> TYPE: DNA
<213> ORGANISM: Homo sapiens

<400> SEQUENCE: 278
cccgccacct acaattccat c                                              21

<210> SEQ ID NO 279
<211> LENGTH: 21
<212> TYPE: DNA
<213> ORGANISM: Homo sapiens

<400> SEQUENCE: 279
gccacctaca attccatcat c                                              21

<210> SEQ ID NO 280
<211> LENGTH: 21
<212> TYPE: DNA
<213> ORGANISM: Homo sapiens
```

-continued

<400> SEQUENCE: 280
cctacaattc catcatcaac c    21

<210> SEQ ID NO 281
<211> LENGTH: 21
<212> TYPE: DNA
<213> ORGANISM: Homo sapiens

<400> SEQUENCE: 281
aattccatca tcaaccctgt c    21

<210> SEQ ID NO 282
<211> LENGTH: 21
<212> TYPE: DNA
<213> ORGANISM: Homo sapiens

<400> SEQUENCE: 282
gctttcagaa accaagagat c    21

<210> SEQ ID NO 283
<211> LENGTH: 21
<212> TYPE: DNA
<213> ORGANISM: Homo sapiens

<400> SEQUENCE: 283
aaaccaagag atccagaaag c    21

<210> SEQ ID NO 284
<211> LENGTH: 21
<212> TYPE: DNA
<213> ORGANISM: Homo sapiens

<400> SEQUENCE: 284
accaagagat ccagaaagcg c    21

<210> SEQ ID NO 285
<211> LENGTH: 21
<212> TYPE: DNA
<213> ORGANISM: Homo sapiens

<400> SEQUENCE: 285
aaagcgctct gtctcatttg c    21

<210> SEQ ID NO 286
<211> LENGTH: 21
<212> TYPE: DNA
<213> ORGANISM: Homo sapiens

<400> SEQUENCE: 286
gcgctctgtc tcatttgctg c    21

<210> SEQ ID NO 287
<211> LENGTH: 21
<212> TYPE: DNA
<213> ORGANISM: Homo sapiens

<400> SEQUENCE: 287
tcatttgctg cggctgcatc c    21

<210> SEQ ID NO 288
<211> LENGTH: 8
<212> TYPE: DNA
<213> ORGANISM: Homo sapiens

<400> SEQUENCE: 288 ttgctata					8

<210> SEQ ID NO 289
<211> LENGTH: 42
<212> TYPE: PRT
<213> ORGANISM: Homo sapiens

<400> SEQUENCE: 289

Met Met Trp Gly Ala Gly Ser Pro Leu Ala Trp Leu Ser Ala Gly Ser
1               5                   10                  15

Gly Asn Val Asn Val Ser Ser Val Gly Pro Ala Glu Gly Pro Thr Gly
            20                  25                  30

Pro Ala Ala Pro Leu Pro Ser Pro Lys Ala
        35                  40

<210> SEQ ID NO 290
<211> LENGTH: 23
<212> TYPE: PRT
<213> ORGANISM: Homo sapiens

<400> SEQUENCE: 290

Trp Asp Val Val Leu Cys Ile Ser Gly Thr Leu Val Ser Cys Glu Asn
1               5                   10                  15

Ala Leu Val Val Ala Ile Ile
            20

<210> SEQ ID NO 291
<211> LENGTH: 12
<212> TYPE: PRT
<213> ORGANISM: Homo sapiens

<400> SEQUENCE: 291

Val Gly Thr Pro Ala Phe Arg Ala Pro Met Phe Leu
1               5                   10

<210> SEQ ID NO 292
<211> LENGTH: 23
<212> TYPE: PRT
<213> ORGANISM: Homo sapiens

<400> SEQUENCE: 292

Leu Val Gly Ser Leu Ala Val Ala Asp Leu Leu Ala Gly Leu Gly Leu
1               5                   10                  15

Val Leu His Phe Ala Ala Val
            20

<210> SEQ ID NO 293
<211> LENGTH: 9
<212> TYPE: PRT
<213> ORGANISM: Homo sapiens

<400> SEQUENCE: 293

Phe Cys Ile Gly Ser Ala Glu Met Ser
1               5

<210> SEQ ID NO 294
<211> LENGTH: 23
<212> TYPE: PRT
<213> ORGANISM: Homo sapiens

<400> SEQUENCE: 294

-continued

Leu Val Leu Val Gly Val Leu Ala Met Ala Phe Thr Ala Ser Ile Gly
1               5                   10                  15

Ser Leu Leu Ala Ile Thr Val
            20

<210> SEQ ID NO 295
<211> LENGTH: 20
<212> TYPE: PRT
<213> ORGANISM: Homo sapiens

<400> SEQUENCE: 295

Asp Arg Tyr Leu Ser Leu Tyr Asn Ala Leu Thr Tyr Tyr Ser Glu Thr
1               5                   10                  15

Thr Val Thr Arg
            20

<210> SEQ ID NO 296
<211> LENGTH: 23
<212> TYPE: PRT
<213> ORGANISM: Homo sapiens

<400> SEQUENCE: 296

Thr Tyr Val Met Leu Ala Leu Val Trp Gly Gly Ala Leu Gly Leu Gly
1               5                   10                  15

Leu Leu Pro Val Leu Ala Trp
            20

<210> SEQ ID NO 297
<211> LENGTH: 19
<212> TYPE: PRT
<213> ORGANISM: Homo sapiens

<400> SEQUENCE: 297

Asn Cys Leu Asp Gly Leu Thr Thr Cys Gly Val Val Tyr Pro Leu Ser
1               5                   10                  15

Lys Asn His

<210> SEQ ID NO 298
<211> LENGTH: 23
<212> TYPE: PRT
<213> ORGANISM: Homo sapiens

<400> SEQUENCE: 298

Leu Val Val Leu Ala Ile Ala Phe Phe Met Val Phe Gly Ile Met Leu
1               5                   10                  15

Gln Leu Tyr Ala Gln Ile Cys
            20

<210> SEQ ID NO 299
<211> LENGTH: 27
<212> TYPE: PRT
<213> ORGANISM: Homo sapiens

<400> SEQUENCE: 299

Arg Ile Val Cys Arg His Ala Gln Gln Ile Ala Leu Gln Arg His Leu
1               5                   10                  15

Leu Pro Ala Ser His Tyr Val Ala Thr Arg Lys
            20                  25

<210> SEQ ID NO 300
<211> LENGTH: 23

```
<212> TYPE: PRT
<213> ORGANISM: Homo sapiens

<400> SEQUENCE: 300

Gly Ile Ala Thr Leu Ala Val Val Leu Gly Ala Phe Ala Ala Cys Trp
1               5                   10                  15

Leu Pro Phe Thr Val Tyr Cys
            20

<210> SEQ ID NO 301
<211> LENGTH: 9
<212> TYPE: PRT
<213> ORGANISM: Homo sapiens

<400> SEQUENCE: 301

Leu Leu Gly Asp Ala His Ser Pro Pro
1               5

<210> SEQ ID NO 302
<211> LENGTH: 23
<212> TYPE: PRT
<213> ORGANISM: Homo sapiens

<400> SEQUENCE: 302

Leu Tyr Thr Tyr Leu Thr Leu Leu Pro Ala Thr Tyr Asn Ser Met Ile
1               5                   10                  15

Asn Pro Ile Ile Tyr Ala Phe
            20

<210> SEQ ID NO 303
<211> LENGTH: 31
<212> TYPE: PRT
<213> ORGANISM: Homo sapiens

<400> SEQUENCE: 303

Arg Asn Gln Asp Val Gln Lys Val Leu Trp Ala Val Cys Cys Cys Cys
1               5                   10                  15

Ser Ser Ser Lys Ile Pro Phe Arg Ser Arg Ser Pro Ser Asp Val
            20                  25                  30

<210> SEQ ID NO 304
<211> LENGTH: 74
<212> TYPE: PRT
<213> ORGANISM: Homo sapiens

<400> SEQUENCE: 304

Met Asn Ala Ser Ala Ala Ser Leu Asn Asp Ser Gln Val Val Val
1               5                   10                  15

Ala Ala Glu Gly Ala Ala Ala Ala Thr Ala Ala Gly Gly Pro Asp
                20                  25                  30

Thr Gly Glu Trp Gly Pro Pro Ala Ala Ala Leu Gly Ala Gly Gly
            35                  40                  45

Gly Ala Asn Gly Ser Leu Glu Leu Ser Ser Gln Leu Ser Ala Gly Pro
        50                  55                  60

Pro Gly Leu Leu Leu Pro Ala Val Asn Pro
65                  70

<210> SEQ ID NO 305
<211> LENGTH: 23
<212> TYPE: PRT
<213> ORGANISM: Homo sapiens
```

-continued

```
<400> SEQUENCE: 305

Trp Asp Val Leu Leu Cys Val Ser Gly Thr Val Ile Ala Gly Glu Asn
1               5                   10                  15

Ala Leu Val Val Ala Leu Ile
            20

<210> SEQ ID NO 306
<211> LENGTH: 12
<212> TYPE: PRT
<213> ORGANISM: Homo sapiens

<400> SEQUENCE: 306

Ala Ser Thr Pro Ala Leu Arg Thr Pro Met Phe Val
1               5                   10

<210> SEQ ID NO 307
<211> LENGTH: 23
<212> TYPE: PRT
<213> ORGANISM: Homo sapiens

<400> SEQUENCE: 307

Leu Val Gly Ser Leu Ala Thr Ala Asp Leu Leu Ala Gly Cys Gly Leu
1               5                   10                  15

Ile Leu His Phe Val Phe Gln
            20

<210> SEQ ID NO 308
<211> LENGTH: 9
<212> TYPE: PRT
<213> ORGANISM: Homo sapiens

<400> SEQUENCE: 308

Tyr Leu Val Pro Ser Glu Thr Val Ser
1               5

<210> SEQ ID NO 309
<211> LENGTH: 23
<212> TYPE: PRT
<213> ORGANISM: Homo sapiens

<400> SEQUENCE: 309

Leu Leu Thr Val Gly Phe Leu Val Ala Ser Phe Ala Ala Ser Val Ser
1               5                   10                  15

Ser Leu Leu Ala Ile Thr Val
            20

<210> SEQ ID NO 310
<211> LENGTH: 20
<212> TYPE: PRT
<213> ORGANISM: Homo sapiens

<400> SEQUENCE: 310

Asp Arg Tyr Leu Ser Leu Tyr Asn Ala Leu Thr Tyr Tyr Ser Arg Arg
1               5                   10                  15

Thr Leu Leu Gly
            20

<210> SEQ ID NO 311
<211> LENGTH: 23
<212> TYPE: PRT
<213> ORGANISM: Homo sapiens

<400> SEQUENCE: 311
```

-continued

Val His Leu Leu Leu Ala Ala Thr Trp Thr Val Ser Leu Gly Leu Gly
1               5                   10                  15

Leu Leu Pro Val Leu Gly Trp
            20

<210> SEQ ID NO 312
<211> LENGTH: 19
<212> TYPE: PRT
<213> ORGANISM: Homo sapiens

<400> SEQUENCE: 312

Asn Cys Leu Ala Glu Arg Ala Ala Cys Ser Val Val Arg Pro Leu Ala
1               5                   10                  15

Arg Ser His

<210> SEQ ID NO 313
<211> LENGTH: 20
<212> TYPE: PRT
<213> ORGANISM: Homo sapiens

<400> SEQUENCE: 313

Val Ala Leu Leu Ser Ala Ala Phe Phe Met Val Phe Gly Ile Met Leu
1               5                   10                  15

His Leu Tyr Val
            20

<210> SEQ ID NO 314
<211> LENGTH: 30
<212> TYPE: PRT
<213> ORGANISM: Homo sapiens

<400> SEQUENCE: 314

Arg Ile Cys Gln Val Val Trp Arg His Ala His Gln Ile Ala Leu Gln
1               5                   10                  15

Gln His Cys Leu Ala Pro Pro His Leu Ala Ala Thr Arg Lys
            20                  25                  30

<210> SEQ ID NO 315
<211> LENGTH: 23
<212> TYPE: PRT
<213> ORGANISM: Homo sapiens

<400> SEQUENCE: 315

Gly Val Gly Thr Leu Ala Val Val Leu Gly Thr Phe Gly Ala Ser Trp
1               5                   10                  15

Leu Pro Phe Ala Ile Tyr Cys
            20

<210> SEQ ID NO 316
<211> LENGTH: 9
<212> TYPE: PRT
<213> ORGANISM: Homo sapiens

<400> SEQUENCE: 316

Val Val Gly Ser His Glu Asp Pro Ala
1               5

<210> SEQ ID NO 317
<211> LENGTH: 32
<212> TYPE: PRT
<213> ORGANISM: Homo sapiens

<400> SEQUENCE: 317

Val Val Gly Ser His Glu Asp Pro Ala Val Tyr Thr Tyr Ala Thr Leu
1               5                   10                  15

Leu Pro Ala Thr Tyr Asn Ser Met Ile Asn Pro Ile Ile Tyr Ala Phe
            20                  25                  30

<210> SEQ ID NO 318
<211> LENGTH: 31
<212> TYPE: PRT
<213> ORGANISM: Homo sapiens

<400> SEQUENCE: 318

Arg Asn Gln Glu Ile Gln Arg Ala Leu Trp Leu Leu Leu Cys Gly Cys
1               5                   10                  15

Phe Gln Ser Lys Val Pro Phe Arg Ser Arg Ser Pro Ser Glu Val
            20                  25                  30

<210> SEQ ID NO 319
<211> LENGTH: 46
<212> TYPE: PRT
<213> ORGANISM: Homo sapiens

<400> SEQUENCE: 319

Met Asn Glu Asp Leu Lys Val Asn Leu Ser Gly Leu Pro Arg Asp Tyr
1               5                   10                  15

Leu Asp Ala Ala Ala Ala Glu Asn Ile Ser Ala Ala Val Ser Ser Arg
            20                  25                  30

Val Pro Ala Val Glu Pro Glu Pro Glu Leu Val Val Asn Pro
        35                  40                  45

<210> SEQ ID NO 320
<211> LENGTH: 23
<212> TYPE: PRT
<213> ORGANISM: Homo sapiens

<400> SEQUENCE: 320

Trp Asp Ile Val Leu Cys Thr Ser Gly Thr Leu Ile Ser Cys Glu Asn
1               5                   10                  15

Ala Ile Val Val Leu Ile Ile
            20

<210> SEQ ID NO 321
<211> LENGTH: 12
<212> TYPE: PRT
<213> ORGANISM: Homo sapiens

<400> SEQUENCE: 321

Phe His Asn Pro Ser Leu Arg Ala Pro Met Phe Leu
1               5                   10

<210> SEQ ID NO 322
<211> LENGTH: 23
<212> TYPE: PRT
<213> ORGANISM: Homo sapiens

<400> SEQUENCE: 322

Leu Ile Gly Ser Leu Ala Leu Ala Asp Leu Leu Ala Gly Ile Gly Leu
1               5                   10                  15

Ile Thr Asn Phe Val Phe Ala
            20

```
<210> SEQ ID NO 323
<211> LENGTH: 9
<212> TYPE: PRT
<213> ORGANISM: Homo sapiens

<400> SEQUENCE: 323

Tyr Leu Leu Gln Ser Glu Ala Thr Lys
1               5

<210> SEQ ID NO 324
<211> LENGTH: 23
<212> TYPE: PRT
<213> ORGANISM: Homo sapiens

<400> SEQUENCE: 324

Leu Val Thr Ile Gly Leu Ile Val Ala Ser Phe Ser Ala Ser Val Cys
1               5                   10                  15

Ser Leu Leu Ala Ile Thr Val
            20

<210> SEQ ID NO 325
<211> LENGTH: 20
<212> TYPE: PRT
<213> ORGANISM: Homo sapiens

<400> SEQUENCE: 325

Asp Arg Tyr Leu Ser Leu Tyr Tyr Ala Leu Thr Tyr His Ser Glu Arg
1               5                   10                  15

Thr Val Thr Phe
            20

<210> SEQ ID NO 326
<211> LENGTH: 23
<212> TYPE: PRT
<213> ORGANISM: Homo sapiens

<400> SEQUENCE: 326

Thr Tyr Val Met Leu Val Met Leu Trp Gly Thr Ser Ile Cys Leu Gly
1               5                   10                  15

Leu Leu Pro Val Met Gly Trp
            20

<210> SEQ ID NO 327
<211> LENGTH: 19
<212> TYPE: PRT
<213> ORGANISM: Homo sapiens

<400> SEQUENCE: 327

Asn Cys Leu Arg Asp Glu Ser Thr Cys Ser Val Val Arg Pro Leu Thr
1               5                   10                  15

Lys Asn Asn

<210> SEQ ID NO 328
<211> LENGTH: 23
<212> TYPE: PRT
<213> ORGANISM: Homo sapiens

<400> SEQUENCE: 328

Ala Ala Ile Leu Ser Val Ser Phe Leu Phe Met Phe Ala Leu Met Leu
1               5                   10                  15

Gln Leu Tyr Ile Gln Ile Cys
            20
```

```
<210> SEQ ID NO 329
<211> LENGTH: 27
<212> TYPE: PRT
<213> ORGANISM: Homo sapiens

<400> SEQUENCE: 329

Lys Ile Val Met Arg His Ala His Gln Ile Ala Leu Gln His His Phe
1               5                   10                  15

Leu Ala Thr Ser His Tyr Val Thr Thr Arg Lys
            20                  25

<210> SEQ ID NO 330
<211> LENGTH: 23
<212> TYPE: PRT
<213> ORGANISM: Homo sapiens

<400> SEQUENCE: 330

Gly Val Ser Thr Leu Ala Ile Ile Leu Gly Thr Phe Ala Ala Cys Trp
1               5                   10                  15

Met Pro Phe Thr Leu Tyr Ser
            20

<210> SEQ ID NO 331
<211> LENGTH: 9
<212> TYPE: PRT
<213> ORGANISM: Homo sapiens

<400> SEQUENCE: 331

Leu Ile Ala Asp Tyr Thr Tyr Pro Ser
1               5

<210> SEQ ID NO 332
<211> LENGTH: 23
<212> TYPE: PRT
<213> ORGANISM: Homo sapiens

<400> SEQUENCE: 332

Ile Tyr Thr Tyr Ala Thr Leu Leu Pro Ala Thr Tyr Asn Ser Ile Ile
1               5                   10                  15

Asn Pro Val Ile Tyr Ala Phe
            20

<210> SEQ ID NO 333
<211> LENGTH: 31
<212> TYPE: PRT
<213> ORGANISM: Homo sapiens

<400> SEQUENCE: 333

Arg Asn Gln Glu Ile Gln Lys Ala Leu Cys Leu Ile Cys Cys Gly Cys
1               5                   10                  15

Ile Pro Ser Ser Leu Ala Gln Arg Ala Arg Ser Pro Ser Asp Val
            20                  25                  30

<210> SEQ ID NO 334
<211> LENGTH: 19
<212> TYPE: DNA
<213> ORGANISM: Homo sapiens

<400> SEQUENCE: 334
gtttatccac tctccaaga                                             19

<210> SEQ ID NO 335
```

```
<211> LENGTH: 19
<212> TYPE: DNA
<213> ORGANISM: Homo sapiens

<400> SEQUENCE: 335
tttatccact ctccaagaa                                                    19

<210> SEQ ID NO 336
<211> LENGTH: 19
<212> TYPE: DNA
<213> ORGANISM: Homo sapiens

<400> SEQUENCE: 336
ccacctctct acacctatc                                                    19

<210> SEQ ID NO 337
<211> LENGTH: 19
<212> TYPE: DNA
<213> ORGANISM: Homo sapiens

<400> SEQUENCE: 337
accgctacct ttctctgta                                                    19

<210> SEQ ID NO 338
<211> LENGTH: 18
<212> TYPE: DNA
<213> ORGANISM: Homo sapiens

<400> SEQUENCE: 338
ggcctttacc gccagcat                                                     18

<210> SEQ ID NO 339
<211> LENGTH: 24
<212> TYPE: DNA
<213> ORGANISM: Homo sapiens

<400> SEQUENCE: 339
tctgaatagt aggtgagggc attg                                              24

<210> SEQ ID NO 340
<211> LENGTH: 19
<212> TYPE: DNA
<213> ORGANISM: Homo sapiens

<400> SEQUENCE: 340
ggatgtggtg ctctgcatc                                                    19

<210> SEQ ID NO 341
<211> LENGTH: 19
<212> TYPE: DNA
<213> ORGANISM: Homo sapiens

<400> SEQUENCE: 341
atgtggtgct ctgcatctc                                                    19

<210> SEQ ID NO 342
<211> LENGTH: 19
<212> TYPE: DNA
<213> ORGANISM: Homo sapiens

<400> SEQUENCE: 342
tgcgctagtg gtggccatc                                                    19
```

```
<210> SEQ ID NO 343
<211> LENGTH: 19
<212> TYPE: DNA
<213> ORGANISM: Homo sapiens

<400> SEQUENCE: 343
cctgcacttt gctgctgtc                                              19

<210> SEQ ID NO 344
<211> LENGTH: 19
<212> TYPE: DNA
<213> ORGANISM: Homo sapiens

<400> SEQUENCE: 344
gcactttgct gctgtcttc                                              19

<210> SEQ ID NO 345
<211> LENGTH: 19
<212> TYPE: DNA
<213> ORGANISM: Homo sapiens

<400> SEQUENCE: 345
ctttgctgct gtcttctgc                                              19

<210> SEQ ID NO 346
<211> LENGTH: 19
<212> TYPE: DNA
<213> ORGANISM: Homo sapiens

<400> SEQUENCE: 346
tgctgctgtc ttctgcatc                                              19

<210> SEQ ID NO 347
<211> LENGTH: 19
<212> TYPE: DNA
<213> ORGANISM: Homo sapiens

<400> SEQUENCE: 347
ctgtcttctg catcggctc                                              19

<210> SEQ ID NO 348
<211> LENGTH: 19
<212> TYPE: DNA
<213> ORGANISM: Homo sapiens

<400> SEQUENCE: 348
tcttctgcat cggctcagc                                              19

<210> SEQ ID NO 349
<211> LENGTH: 19
<212> TYPE: DNA
<213> ORGANISM: Homo sapiens

<400> SEQUENCE: 349
tgctggcaat ggcctttac                                              19

<210> SEQ ID NO 350
<211> LENGTH: 19
<212> TYPE: DNA
<213> ORGANISM: Homo sapiens

<400> SEQUENCE: 350
gctggcaatg gcctttacc                                              19
```

```
<210> SEQ ID NO 351
<211> LENGTH: 19
<212> TYPE: DNA
<213> ORGANISM: Homo sapiens

<400> SEQUENCE: 351
ggcctttacc gccagcatc                                                    19

<210> SEQ ID NO 352
<211> LENGTH: 19
<212> TYPE: DNA
<213> ORGANISM: Homo sapiens

<400> SEQUENCE: 352
cggcagtcta ctggccatc                                                    19

<210> SEQ ID NO 353
<211> LENGTH: 19
<212> TYPE: DNA
<213> ORGANISM: Homo sapiens

<400> SEQUENCE: 353
tctactggcc atcactgtc                                                    19

<210> SEQ ID NO 354
<211> LENGTH: 19
<212> TYPE: DNA
<213> ORGANISM: Homo sapiens

<400> SEQUENCE: 354
actggccatc actgtcgac                                                    19

<210> SEQ ID NO 355
<211> LENGTH: 19
<212> TYPE: DNA
<213> ORGANISM: Homo sapiens

<400> SEQUENCE: 355
ctggccatca ctgtcgacc                                                    19

<210> SEQ ID NO 356
<211> LENGTH: 19
<212> TYPE: DNA
<213> ORGANISM: Homo sapiens

<400> SEQUENCE: 356
ctgtcgaccg ctacctttc                                                    19

<210> SEQ ID NO 357
<211> LENGTH: 19
<212> TYPE: DNA
<213> ORGANISM: Homo sapiens

<400> SEQUENCE: 357
gtcgaccgct acctttctc                                                    19

<210> SEQ ID NO 358
<211> LENGTH: 19
<212> TYPE: DNA
<213> ORGANISM: Homo sapiens

<400> SEQUENCE: 358
ccgctacctt tctctgtac                                                    19
```

<210> SEQ ID NO 359
<211> LENGTH: 19
<212> TYPE: DNA
<213> ORGANISM: Homo sapiens

<400> SEQUENCE: 359
acctttctct gtacaatgc                                               19

<210> SEQ ID NO 360
<211> LENGTH: 19
<212> TYPE: DNA
<213> ORGANISM: Homo sapiens

<400> SEQUENCE: 360
cctttctctg tacaatgcc                                               19

<210> SEQ ID NO 361
<211> LENGTH: 19
<212> TYPE: DNA
<213> ORGANISM: Homo sapiens

<400> SEQUENCE: 361
ctttctctgt acaatgccc                                               19

<210> SEQ ID NO 362
<211> LENGTH: 19
<212> TYPE: DNA
<213> ORGANISM: Homo sapiens

<400> SEQUENCE: 362
ttctctgtac aatgccctc                                               19

<210> SEQ ID NO 363
<211> LENGTH: 19
<212> TYPE: DNA
<213> ORGANISM: Homo sapiens

<400> SEQUENCE: 363
ctctgtacaa tgccctcac                                               19

<210> SEQ ID NO 364
<211> LENGTH: 19
<212> TYPE: DNA
<213> ORGANISM: Homo sapiens

<400> SEQUENCE: 364
tctgtacaat gccctcacc                                               19

<210> SEQ ID NO 365
<211> LENGTH: 19
<212> TYPE: DNA
<213> ORGANISM: Homo sapiens

<400> SEQUENCE: 365
gtacaatgcc ctcacctac                                               19

<210> SEQ ID NO 366
<211> LENGTH: 19
<212> TYPE: DNA
<213> ORGANISM: Homo sapiens

<400> SEQUENCE: 366

| | |
|---|---|
| atgccctcac ctactattc | 19 |

<210> SEQ ID NO 367
<211> LENGTH: 19
<212> TYPE: DNA
<213> ORGANISM: Homo sapiens

<400> SEQUENCE: 367

| | |
|---|---|
| tcacctacta ttcagagac | 19 |

<210> SEQ ID NO 368
<211> LENGTH: 19
<212> TYPE: DNA
<213> ORGANISM: Homo sapiens

<400> SEQUENCE: 368

| | |
|---|---|
| cctactattc agagacaac | 19 |

<210> SEQ ID NO 369
<211> LENGTH: 19
<212> TYPE: DNA
<213> ORGANISM: Homo sapiens

<400> SEQUENCE: 369

| | |
|---|---|
| attcagagac aacagtgac | 19 |

<210> SEQ ID NO 370
<211> LENGTH: 19
<212> TYPE: DNA
<213> ORGANISM: Homo sapiens

<400> SEQUENCE: 370

| | |
|---|---|
| tcagagacaa cagtgacac | 19 |

<210> SEQ ID NO 371
<211> LENGTH: 19
<212> TYPE: DNA
<213> ORGANISM: Homo sapiens

<400> SEQUENCE: 371

| | |
|---|---|
| agacaacagt gacacggac | 19 |

<210> SEQ ID NO 372
<211> LENGTH: 19
<212> TYPE: DNA
<213> ORGANISM: Homo sapiens

<400> SEQUENCE: 372

| | |
|---|---|
| gacaacagtg acacggacc | 19 |

<210> SEQ ID NO 373
<211> LENGTH: 19
<212> TYPE: DNA
<213> ORGANISM: Homo sapiens

<400> SEQUENCE: 373

| | |
|---|---|
| acacggacct atgtgatgc | 19 |

<210> SEQ ID NO 374
<211> LENGTH: 19
<212> TYPE: DNA
<213> ORGANISM: Homo sapiens

<400> SEQUENCE: 374
ggacctatgt gatgctggc                                                19

<210> SEQ ID NO 375
<211> LENGTH: 19
<212> TYPE: DNA
<213> ORGANISM: Homo sapiens

<400> SEQUENCE: 375
acatgtggcg tggtttatc                                                19

<210> SEQ ID NO 376
<211> LENGTH: 19
<212> TYPE: DNA
<213> ORGANISM: Homo sapiens

<400> SEQUENCE: 376
catgtggcgt ggtttatcc                                                19

<210> SEQ ID NO 377
<211> LENGTH: 19
<212> TYPE: DNA
<213> ORGANISM: Homo sapiens

<400> SEQUENCE: 377
tgtggcgtgg tttatccac                                                19

<210> SEQ ID NO 378
<211> LENGTH: 19
<212> TYPE: DNA
<213> ORGANISM: Homo sapiens

<400> SEQUENCE: 378
tggcgtggtt tatccactc                                                19

<210> SEQ ID NO 379
<211> LENGTH: 19
<212> TYPE: DNA
<213> ORGANISM: Homo sapiens

<400> SEQUENCE: 379
gcgtggttta tccactctc                                                19

<210> SEQ ID NO 380
<211> LENGTH: 19
<212> TYPE: DNA
<213> ORGANISM: Homo sapiens

<400> SEQUENCE: 380
cgtggtttat ccactctcc                                                19

<210> SEQ ID NO 381
<211> LENGTH: 19
<212> TYPE: DNA
<213> ORGANISM: Homo sapiens

<400> SEQUENCE: 381
ttatccactc tccaagaac                                                19

<210> SEQ ID NO 382
<211> LENGTH: 19
<212> TYPE: DNA
<213> ORGANISM: Homo sapiens

```
<400> SEQUENCE: 382
tatccactct ccaagaacc                                              19

<210> SEQ ID NO 383
<211> LENGTH: 19
<212> TYPE: DNA
<213> ORGANISM: Homo sapiens

<400> SEQUENCE: 383
ccactctcca agaaccatc                                              19

<210> SEQ ID NO 384
<211> LENGTH: 19
<212> TYPE: DNA
<213> ORGANISM: Homo sapiens

<400> SEQUENCE: 384
aagaaccatc tggtagttc                                              19

<210> SEQ ID NO 385
<211> LENGTH: 19
<212> TYPE: DNA
<213> ORGANISM: Homo sapiens

<400> SEQUENCE: 385
accatctggt agttctggc                                              19

<210> SEQ ID NO 386
<211> LENGTH: 19
<212> TYPE: DNA
<213> ORGANISM: Homo sapiens

<400> SEQUENCE: 386
ccatctggta gttctggcc                                              19

<210> SEQ ID NO 387
<211> LENGTH: 19
<212> TYPE: DNA
<213> ORGANISM: Homo sapiens

<400> SEQUENCE: 387
tggtagttct ggccattgc                                              19

<210> SEQ ID NO 388
<211> LENGTH: 19
<212> TYPE: DNA
<213> ORGANISM: Homo sapiens

<400> SEQUENCE: 388
ggtagttctg gccattgcc                                              19

<210> SEQ ID NO 389
<211> LENGTH: 19
<212> TYPE: DNA
<213> ORGANISM: Homo sapiens

<400> SEQUENCE: 389
agttctggcc attgccttc                                              19

<210> SEQ ID NO 390
<211> LENGTH: 19
<212> TYPE: DNA
<213> ORGANISM: Homo sapiens
```

```
<400> SEQUENCE: 390
tctggccatt gccttcttc                                                19

<210> SEQ ID NO 391
<211> LENGTH: 19
<212> TYPE: DNA
<213> ORGANISM: Homo sapiens

<400> SEQUENCE: 391
cttcttcatg gtgtttggc                                                19

<210> SEQ ID NO 392
<211> LENGTH: 19
<212> TYPE: DNA
<213> ORGANISM: Homo sapiens

<400> SEQUENCE: 392
cttcatggtg tttggcatc                                                19

<210> SEQ ID NO 393
<211> LENGTH: 19
<212> TYPE: DNA
<213> ORGANISM: Homo sapiens

<400> SEQUENCE: 393
atggtgtttg gcatcatgc                                                19

<210> SEQ ID NO 394
<211> LENGTH: 19
<212> TYPE: DNA
<213> ORGANISM: Homo sapiens

<400> SEQUENCE: 394
gtgtttggca tcatgctgc                                                19

<210> SEQ ID NO 395
<211> LENGTH: 19
<212> TYPE: DNA
<213> ORGANISM: Homo sapiens

<400> SEQUENCE: 395
tttggcatca tgctgcagc                                                19

<210> SEQ ID NO 396
<211> LENGTH: 19
<212> TYPE: DNA
<213> ORGANISM: Homo sapiens

<400> SEQUENCE: 396
tggcatcatg ctgcagctc                                                19

<210> SEQ ID NO 397
<211> LENGTH: 19
<212> TYPE: DNA
<213> ORGANISM: Homo sapiens

<400> SEQUENCE: 397
catcatgctg cagctctac                                                19

<210> SEQ ID NO 398
<211> LENGTH: 19
<212> TYPE: DNA
```

-continued

<213> ORGANISM: Homo sapiens

<400> SEQUENCE: 398
tcatgctgca gctctacgc                                                    19

<210> SEQ ID NO 399
<211> LENGTH: 19
<212> TYPE: DNA
<213> ORGANISM: Homo sapiens

<400> SEQUENCE: 399
catgctgcag ctctacgcc                                                    19

<210> SEQ ID NO 400
<211> LENGTH: 19
<212> TYPE: DNA
<213> ORGANISM: Homo sapiens

<400> SEQUENCE: 400
gcagctctac gcccaaatc                                                    19

<210> SEQ ID NO 401
<211> LENGTH: 19
<212> TYPE: DNA
<213> ORGANISM: Homo sapiens

<400> SEQUENCE: 401
gctctacgcc caaatctgc                                                    19

<210> SEQ ID NO 402
<211> LENGTH: 19
<212> TYPE: DNA
<213> ORGANISM: Homo sapiens

<400> SEQUENCE: 402
ctctacgccc aaatctgcc                                                    19

<210> SEQ ID NO 403
<211> LENGTH: 19
<212> TYPE: DNA
<213> ORGANISM: Homo sapiens

<400> SEQUENCE: 403
cgcccaaatc tgccgcatc                                                    19

<210> SEQ ID NO 404
<211> LENGTH: 19
<212> TYPE: DNA
<213> ORGANISM: Homo sapiens

<400> SEQUENCE: 404
aatctgccgc atcgtctgc                                                    19

<210> SEQ ID NO 405
<211> LENGTH: 19
<212> TYPE: DNA
<213> ORGANISM: Homo sapiens

<400> SEQUENCE: 405
atctgccgca tcgtctgcc                                                    19

<210> SEQ ID NO 406
<211> LENGTH: 19

```
<212> TYPE: DNA
<213> ORGANISM: Homo sapiens

<400> SEQUENCE: 406
gcccagcaga ttgcccttc                                              19

<210> SEQ ID NO 407
<211> LENGTH: 19
<212> TYPE: DNA
<213> ORGANISM: Homo sapiens

<400> SEQUENCE: 407
ctggttgccc ttcactgtc                                              19

<210> SEQ ID NO 408
<211> LENGTH: 19
<212> TYPE: DNA
<213> ORGANISM: Homo sapiens

<400> SEQUENCE: 408
gttgcccttc actgtctac                                              19

<210> SEQ ID NO 409
<211> LENGTH: 19
<212> TYPE: DNA
<213> ORGANISM: Homo sapiens

<400> SEQUENCE: 409
gcccttcact gtctactgc                                              19

<210> SEQ ID NO 410
<211> LENGTH: 19
<212> TYPE: DNA
<213> ORGANISM: Homo sapiens

<400> SEQUENCE: 410
cccttcactg tctactgcc                                              19

<210> SEQ ID NO 411
<211> LENGTH: 19
<212> TYPE: DNA
<213> ORGANISM: Homo sapiens

<400> SEQUENCE: 411
ttcactgtct actgcctgc                                              19

<210> SEQ ID NO 412
<211> LENGTH: 19
<212> TYPE: DNA
<213> ORGANISM: Homo sapiens

<400> SEQUENCE: 412
actctccacc tctctacac                                              19

<210> SEQ ID NO 413
<211> LENGTH: 19
<212> TYPE: DNA
<213> ORGANISM: Homo sapiens

<400> SEQUENCE: 413
ctctccacct ctctacacc                                              19

<210> SEQ ID NO 414
```

```
<211> LENGTH: 19
<212> TYPE: DNA
<213> ORGANISM: Homo sapiens

<400> SEQUENCE: 414
ccacctctct acacctatc                                                      19

<210> SEQ ID NO 415
<211> LENGTH: 19
<212> TYPE: DNA
<213> ORGANISM: Homo sapiens

<400> SEQUENCE: 415
ctctctacac ctatcttac                                                      19

<210> SEQ ID NO 416
<211> LENGTH: 19
<212> TYPE: DNA
<213> ORGANISM: Homo sapiens

<400> SEQUENCE: 416
tctctacacc tatcttacc                                                      19

<210> SEQ ID NO 417
<211> LENGTH: 19
<212> TYPE: DNA
<213> ORGANISM: Homo sapiens

<400> SEQUENCE: 417
tacacctatc ttaccttgc                                                      19

<210> SEQ ID NO 418
<211> LENGTH: 19
<212> TYPE: DNA
<213> ORGANISM: Homo sapiens

<400> SEQUENCE: 418
cacctatctt accttgctc                                                      19

<210> SEQ ID NO 419
<211> LENGTH: 19
<212> TYPE: DNA
<213> ORGANISM: Homo sapiens

<400> SEQUENCE: 419
acctatctta ccttgctcc                                                      19

<210> SEQ ID NO 420
<211> LENGTH: 19
<212> TYPE: DNA
<213> ORGANISM: Homo sapiens

<400> SEQUENCE: 420
cctatcttac cttgctccc                                                      19

<210> SEQ ID NO 421
<211> LENGTH: 19
<212> TYPE: DNA
<213> ORGANISM: Homo sapiens

<400> SEQUENCE: 421
atcttacctt gctccctgc                                                      19
```

```
<210> SEQ ID NO 422
<211> LENGTH: 19
<212> TYPE: DNA
<213> ORGANISM: Homo sapiens

<400> SEQUENCE: 422
tcttaccttg ctccctgcc                                           19

<210> SEQ ID NO 423
<211> LENGTH: 19
<212> TYPE: DNA
<213> ORGANISM: Homo sapiens

<400> SEQUENCE: 423
ttaccttgct ccctgccac                                           19

<210> SEQ ID NO 424
<211> LENGTH: 19
<212> TYPE: DNA
<213> ORGANISM: Homo sapiens

<400> SEQUENCE: 424
gctccctgcc acctacaac                                           19

<210> SEQ ID NO 425
<211> LENGTH: 19
<212> TYPE: DNA
<213> ORGANISM: Homo sapiens

<400> SEQUENCE: 425
cacctacaac tccatgatc                                           19

<210> SEQ ID NO 426
<211> LENGTH: 19
<212> TYPE: DNA
<213> ORGANISM: Homo sapiens

<400> SEQUENCE: 426
ctacaactcc atgatcaac                                           19

<210> SEQ ID NO 427
<211> LENGTH: 19
<212> TYPE: DNA
<213> ORGANISM: Homo sapiens

<400> SEQUENCE: 427
tacaactcca tgatcaacc                                           19

<210> SEQ ID NO 428
<211> LENGTH: 19
<212> TYPE: DNA
<213> ORGANISM: Homo sapiens

<400> SEQUENCE: 428
acaactccat gatcaaccc                                           19

<210> SEQ ID NO 429
<211> LENGTH: 19
<212> TYPE: DNA
<213> ORGANISM: Homo sapiens

<400> SEQUENCE: 429
ctccatgatc aaccctatc                                           19
```

```
<210> SEQ ID NO 430
<211> LENGTH: 19
<212> TYPE: DNA
<213> ORGANISM: Homo sapiens

<400> SEQUENCE: 430
catgatcaac cctatcatc                                                    19

<210> SEQ ID NO 431
<211> LENGTH: 19
<212> TYPE: DNA
<213> ORGANISM: Homo sapiens

<400> SEQUENCE: 431
tcaaccctat catctacgc                                                    19

<210> SEQ ID NO 432
<211> LENGTH: 19
<212> TYPE: DNA
<213> ORGANISM: Homo sapiens

<400> SEQUENCE: 432
caaccctatc atctacgcc                                                    19

<210> SEQ ID NO 433
<211> LENGTH: 19
<212> TYPE: DNA
<213> ORGANISM: Homo sapiens

<400> SEQUENCE: 433
ccctatcatc tacgccttc                                                    19

<210> SEQ ID NO 434
<211> LENGTH: 19
<212> TYPE: DNA
<213> ORGANISM: Homo sapiens

<400> SEQUENCE: 434
cctatcatct acgccttcc                                                    19

<210> SEQ ID NO 435
<211> LENGTH: 19
<212> TYPE: DNA
<213> ORGANISM: Homo sapiens

<400> SEQUENCE: 435
tatcatctac gccttccgc                                                    19

<210> SEQ ID NO 436
<211> LENGTH: 19
<212> TYPE: DNA
<213> ORGANISM: Homo sapiens

<400> SEQUENCE: 436
catctacgcc ttccgcaac                                                    19

<210> SEQ ID NO 437
<211> LENGTH: 19
<212> TYPE: DNA
<213> ORGANISM: Homo sapiens

<400> SEQUENCE: 437
atctacgcct tccgcaacc                                                    19
```

<210> SEQ ID NO 438
<211> LENGTH: 19
<212> TYPE: DNA
<213> ORGANISM: Homo sapiens

<400> SEQUENCE: 438
caggatgtgc agaaagtgc                                              19

<210> SEQ ID NO 439
<211> LENGTH: 19
<212> TYPE: DNA
<213> ORGANISM: Homo sapiens

<400> SEQUENCE: 439
tgcagaaagt gctgtgggc                                              19

<210> SEQ ID NO 440
<211> LENGTH: 19
<212> TYPE: DNA
<213> ORGANISM: Homo sapiens

<400> SEQUENCE: 440
agtgctgtgg gctgtctgc                                              19

<210> SEQ ID NO 441
<211> LENGTH: 19
<212> TYPE: DNA
<213> ORGANISM: Homo sapiens

<400> SEQUENCE: 441
tgttcctctt ccaagatcc                                              19

<210> SEQ ID NO 442
<211> LENGTH: 19
<212> TYPE: DNA
<213> ORGANISM: Homo sapiens

<400> SEQUENCE: 442
gctaatgggt ctctggagc                                              19

<210> SEQ ID NO 443
<211> LENGTH: 19
<212> TYPE: DNA
<213> ORGANISM: Homo sapiens

<400> SEQUENCE: 443
atgggtctct ggagctgtc                                              19

<210> SEQ ID NO 444
<211> LENGTH: 19
<212> TYPE: DNA
<213> ORGANISM: Homo sapiens

<400> SEQUENCE: 444
tgggtctctg gagctgtcc                                              19

<210> SEQ ID NO 445
<211> LENGTH: 19
<212> TYPE: DNA
<213> ORGANISM: Homo sapiens

<400> SEQUENCE: 445

|  |  |
|---|---|
| gttcgtgctg gtaggcagc | 19 |

<210> SEQ ID NO 446
<211> LENGTH: 19
<212> TYPE: DNA
<213> ORGANISM: Homo sapiens

<400> SEQUENCE: 446

|  |  |
|---|---|
| catcttgcac tttgtgttc | 19 |

<210> SEQ ID NO 447
<211> LENGTH: 19
<212> TYPE: DNA
<213> ORGANISM: Homo sapiens

<400> SEQUENCE: 447

|  |  |
|---|---|
| atcttgcact ttgtgttcc | 19 |

<210> SEQ ID NO 448
<211> LENGTH: 19
<212> TYPE: DNA
<213> ORGANISM: Homo sapiens

<400> SEQUENCE: 448

|  |  |
|---|---|
| gcactttgtg ttccagtac | 19 |

<210> SEQ ID NO 449
<211> LENGTH: 19
<212> TYPE: DNA
<213> ORGANISM: Homo sapiens

<400> SEQUENCE: 449

|  |  |
|---|---|
| gtgttccagt acttggtgc | 19 |

<210> SEQ ID NO 450
<211> LENGTH: 19
<212> TYPE: DNA
<213> ORGANISM: Homo sapiens

<400> SEQUENCE: 450

|  |  |
|---|---|
| tgttccagta cttggtgcc | 19 |

<210> SEQ ID NO 451
<211> LENGTH: 19
<212> TYPE: DNA
<213> ORGANISM: Homo sapiens

<400> SEQUENCE: 451

|  |  |
|---|---|
| gttccagtac ttggtgccc | 19 |

<210> SEQ ID NO 452
<211> LENGTH: 19
<212> TYPE: DNA
<213> ORGANISM: Homo sapiens

<400> SEQUENCE: 452

|  |  |
|---|---|
| tccagtactt ggtgccctc | 19 |

<210> SEQ ID NO 453
<211> LENGTH: 19
<212> TYPE: DNA
<213> ORGANISM: Homo sapiens

<400> SEQUENCE: 453
ggagactgtg agtctgctc								19

<210> SEQ ID NO 454
<211> LENGTH: 19
<212> TYPE: DNA
<213> ORGANISM: Homo sapiens

<400> SEQUENCE: 454
agactgtgag tctgctcac								19

<210> SEQ ID NO 455
<211> LENGTH: 19
<212> TYPE: DNA
<213> ORGANISM: Homo sapiens

<400> SEQUENCE: 455
ctacctgtcc ctgtataac								19

<210> SEQ ID NO 456
<211> LENGTH: 19
<212> TYPE: DNA
<213> ORGANISM: Homo sapiens

<400> SEQUENCE: 456
acctgtccct gtataacgc								19

<210> SEQ ID NO 457
<211> LENGTH: 19
<212> TYPE: DNA
<213> ORGANISM: Homo sapiens

<400> SEQUENCE: 457
ctgtccctgt ataacgcgc								19

<210> SEQ ID NO 458
<211> LENGTH: 19
<212> TYPE: DNA
<213> ORGANISM: Homo sapiens

<400> SEQUENCE: 458
gtccctgtat aacgcgctc								19

<210> SEQ ID NO 459
<211> LENGTH: 19
<212> TYPE: DNA
<213> ORGANISM: Homo sapiens

<400> SEQUENCE: 459
ccctgtataa cgcgctcac								19

<210> SEQ ID NO 460
<211> LENGTH: 19
<212> TYPE: DNA
<213> ORGANISM: Homo sapiens

<400> SEQUENCE: 460
cctgtataac gcgctcacc								19

<210> SEQ ID NO 461
<211> LENGTH: 19
<212> TYPE: DNA
<213> ORGANISM: Homo sapiens

<400> SEQUENCE: 461
taacgcgctc acctattac                                            19

<210> SEQ ID NO 462
<211> LENGTH: 19
<212> TYPE: DNA
<213> ORGANISM: Homo sapiens

<400> SEQUENCE: 462
acgcgctcac ctattactc                                            19

<210> SEQ ID NO 463
<211> LENGTH: 19
<212> TYPE: DNA
<213> ORGANISM: Homo sapiens

<400> SEQUENCE: 463
gcgctcacct attactcgc                                            19

<210> SEQ ID NO 464
<211> LENGTH: 19
<212> TYPE: DNA
<213> ORGANISM: Homo sapiens

<400> SEQUENCE: 464
cgccttcttc atggtcttc                                            19

<210> SEQ ID NO 465
<211> LENGTH: 19
<212> TYPE: DNA
<213> ORGANISM: Homo sapiens

<400> SEQUENCE: 465
cttcttcatg gtcttcggc                                            19

<210> SEQ ID NO 466
<211> LENGTH: 19
<212> TYPE: DNA
<213> ORGANISM: Homo sapiens

<400> SEQUENCE: 466
cttcatggtc ttcggcatc                                            19

<210> SEQ ID NO 467
<211> LENGTH: 19
<212> TYPE: DNA
<213> ORGANISM: Homo sapiens

<400> SEQUENCE: 467
atggtcttcg gcatcatgc                                            19

<210> SEQ ID NO 468
<211> LENGTH: 19
<212> TYPE: DNA
<213> ORGANISM: Homo sapiens

<400> SEQUENCE: 468
gtcttcggca tcatgctgc                                            19

<210> SEQ ID NO 469
<211> LENGTH: 19
<212> TYPE: DNA
<213> ORGANISM: Homo sapiens

```
<400> SEQUENCE: 469
cttcggcatc atgctgcac                                                19

<210> SEQ ID NO 470
<211> LENGTH: 19
<212> TYPE: DNA
<213> ORGANISM: Homo sapiens

<400> SEQUENCE: 470
ttcggcatca tgctgcacc                                                19

<210> SEQ ID NO 471
<211> LENGTH: 19
<212> TYPE: DNA
<213> ORGANISM: Homo sapiens

<400> SEQUENCE: 471
catcatgctg cacctgtac                                                19

<210> SEQ ID NO 472
<211> LENGTH: 19
<212> TYPE: DNA
<213> ORGANISM: Homo sapiens

<400> SEQUENCE: 472
atgctgcacc tgtacgtgc                                                19

<210> SEQ ID NO 473
<211> LENGTH: 19
<212> TYPE: DNA
<213> ORGANISM: Homo sapiens

<400> SEQUENCE: 473
ccagaaaggg tgtgggtac                                                19

<210> SEQ ID NO 474
<211> LENGTH: 19
<212> TYPE: DNA
<213> ORGANISM: Homo sapiens

<400> SEQUENCE: 474 agaaaggtg tgggtacac                                                 19

<210> SEQ ID NO 475
<211> LENGTH: 19
<212> TYPE: DNA
<213> ORGANISM: Homo sapiens

<400> SEQUENCE: 475
agggtgtggg tacactggc                                                19

<210> SEQ ID NO 476
<211> LENGTH: 19
<212> TYPE: DNA
<213> ORGANISM: Homo sapiens

<400> SEQUENCE: 476
gcccttcgcc atctattgc                                                19

<210> SEQ ID NO 477
<211> LENGTH: 19
<212> TYPE: DNA
```

<213> ORGANISM: Homo sapiens

<400> SEQUENCE: 477
ctattgcgtg gtgggcagc                                                19

<210> SEQ ID NO 478
<211> LENGTH: 19
<212> TYPE: DNA
<213> ORGANISM: Homo sapiens

<400> SEQUENCE: 478
tacacttacg ccaccctgc                                                19

<210> SEQ ID NO 479
<211> LENGTH: 19
<212> TYPE: DNA
<213> ORGANISM: Homo sapiens

<400> SEQUENCE: 479
tacaactcca tgatcaatc                                                19

<210> SEQ ID NO 480
<211> LENGTH: 19
<212> TYPE: DNA
<213> ORGANISM: Homo sapiens

<400> SEQUENCE: 480
acaactccat gatcaatcc                                                19

<210> SEQ ID NO 481
<211> LENGTH: 19
<212> TYPE: DNA
<213> ORGANISM: Homo sapiens

<400> SEQUENCE: 481
caactccatg atcaatccc                                                19

<210> SEQ ID NO 482
<211> LENGTH: 19
<212> TYPE: DNA
<213> ORGANISM: Homo sapiens

<400> SEQUENCE: 482
ctccatgatc aatcccatc                                                19

<210> SEQ ID NO 483
<211> LENGTH: 19
<212> TYPE: DNA
<213> ORGANISM: Homo sapiens

<400> SEQUENCE: 483
catgatcaat cccatcatc                                                19

<210> SEQ ID NO 484
<211> LENGTH: 19
<212> TYPE: DNA
<213> ORGANISM: Homo sapiens

<400> SEQUENCE: 484
tcaatcccat catctatgc                                                19

<210> SEQ ID NO 485
<211> LENGTH: 19

```
<212> TYPE: DNA
<213> ORGANISM: Homo sapiens

<400> SEQUENCE: 485
caatcccatc atctatgcc                                                19

<210> SEQ ID NO 486
<211> LENGTH: 19
<212> TYPE: DNA
<213> ORGANISM: Homo sapiens

<400> SEQUENCE: 486
tcccatcatc tatgccttc                                                19

<210> SEQ ID NO 487
<211> LENGTH: 19
<212> TYPE: DNA
<213> ORGANISM: Homo sapiens

<400> SEQUENCE: 487
cccatcatct atgccttcc                                                19

<210> SEQ ID NO 488
<211> LENGTH: 19
<212> TYPE: DNA
<213> ORGANISM: Homo sapiens

<400> SEQUENCE: 488
catcatctat gccttccgc                                                19

<210> SEQ ID NO 489
<211> LENGTH: 19
<212> TYPE: DNA
<213> ORGANISM: Homo sapiens

<400> SEQUENCE: 489
catctatgcc ttccgcaac                                                19

<210> SEQ ID NO 490
<211> LENGTH: 19
<212> TYPE: DNA
<213> ORGANISM: Homo sapiens

<400> SEQUENCE: 490
atctatgcct tccgcaacc                                                19

<210> SEQ ID NO 491
<211> LENGTH: 19
<212> TYPE: DNA
<213> ORGANISM: Homo sapiens

<400> SEQUENCE: 491
cctgctctgt ggctgtttc                                                19

<210> SEQ ID NO 492
<211> LENGTH: 19
<212> TYPE: DNA
<213> ORGANISM: Homo sapiens

<400> SEQUENCE: 492
ctgctctgtg gctgtttcc                                                19

<210> SEQ ID NO 493
```

```
<211> LENGTH: 19
<212> TYPE: DNA
<213> ORGANISM: Homo sapiens

<400> SEQUENCE: 493
tctgtggctg tttccagtc                                                    19

<210> SEQ ID NO 494
<211> LENGTH: 19
<212> TYPE: DNA
<213> ORGANISM: Homo sapiens

<400> SEQUENCE: 494
ctgtggctgt ttccagtcc                                                    19

<210> SEQ ID NO 495
<211> LENGTH: 19
<212> TYPE: DNA
<213> ORGANISM: Homo sapiens

<400> SEQUENCE: 495
tgtttccagt ccaaagtgc                                                    19

<210> SEQ ID NO 496
<211> LENGTH: 19
<212> TYPE: DNA
<213> ORGANISM: Homo sapiens

<400> SEQUENCE: 496
gtttccagtc caaagtgcc                                                    19

<210> SEQ ID NO 497
<211> LENGTH: 19
<212> TYPE: DNA
<213> ORGANISM: Homo sapiens

<400> SEQUENCE: 497
tttccagtcc aaagtgccc                                                    19

<210> SEQ ID NO 498
<211> LENGTH: 19
<212> TYPE: DNA
<213> ORGANISM: Homo sapiens

<400> SEQUENCE: 498
cagtccaaag tgccctttc                                                    19

<210> SEQ ID NO 499
<211> LENGTH: 19
<212> TYPE: DNA
<213> ORGANISM: Homo sapiens

<400> SEQUENCE: 499
ccaaagtgcc ctttcgttc                                                    19

<210> SEQ ID NO 500
<211> LENGTH: 19
<212> TYPE: DNA
<213> ORGANISM: Homo sapiens

<400> SEQUENCE: 500
caaagtgccc tttcgttcc                                                    19
```

```
<210> SEQ ID NO 501
<211> LENGTH: 19
<212> TYPE: DNA
<213> ORGANISM: Homo sapiens

<400> SEQUENCE: 501
tgccctttcg ttccaggtc                                               19

<210> SEQ ID NO 502
<211> LENGTH: 19
<212> TYPE: DNA
<213> ORGANISM: Homo sapiens

<400> SEQUENCE: 502
ccctttcgtt ccaggtctc                                               19

<210> SEQ ID NO 503
<211> LENGTH: 19
<212> TYPE: DNA
<213> ORGANISM: Homo sapiens

<400> SEQUENCE: 503
tcgttccagg tctcccagc                                               19

<210> SEQ ID NO 504
<211> LENGTH: 19
<212> TYPE: DNA
<213> ORGANISM: Homo sapiens

<400> SEQUENCE: 504
gcctgagctc gtagtcaac                                               19

<210> SEQ ID NO 505
<211> LENGTH: 19
<212> TYPE: DNA
<213> ORGANISM: Homo sapiens

<400> SEQUENCE: 505
cctgagctcg tagtcaacc                                               19

<210> SEQ ID NO 506
<211> LENGTH: 19
<212> TYPE: DNA
<213> ORGANISM: Homo sapiens

<400> SEQUENCE: 506
gggacattgt cttgtgtac                                               19

<210> SEQ ID NO 507
<211> LENGTH: 19
<212> TYPE: DNA
<213> ORGANISM: Homo sapiens

<400> SEQUENCE: 507
ggacattgtc ttgtgtacc                                               19

<210> SEQ ID NO 508
<211> LENGTH: 19
<212> TYPE: DNA
<213> ORGANISM: Homo sapiens

<400> SEQUENCE: 508
acattgtctt gtgtacctc                                               19
```

```
<210> SEQ ID NO 509
<211> LENGTH: 19
<212> TYPE: DNA
<213> ORGANISM: Homo sapiens

<400> SEQUENCE: 509
tcttgtgtac ctcgggaac                                                19

<210> SEQ ID NO 510
<211> LENGTH: 19
<212> TYPE: DNA
<213> ORGANISM: Homo sapiens

<400> SEQUENCE: 510
cttgtgtacc tcgggaacc                                                19

<210> SEQ ID NO 511
<211> LENGTH: 19
<212> TYPE: DNA
<213> ORGANISM: Homo sapiens

<400> SEQUENCE: 511
ttgtgtacct cgggaaccc                                                19

<210> SEQ ID NO 512
<211> LENGTH: 19
<212> TYPE: DNA
<213> ORGANISM: Homo sapiens

<400> SEQUENCE: 512
gtgtacctcg ggaaccctc                                                19

<210> SEQ ID NO 513
<211> LENGTH: 19
<212> TYPE: DNA
<213> ORGANISM: Homo sapiens

<400> SEQUENCE: 513
tacctcggga accctcatc                                                19

<210> SEQ ID NO 514
<211> LENGTH: 19
<212> TYPE: DNA
<213> ORGANISM: Homo sapiens

<400> SEQUENCE: 514
cctcgggaac cctcatctc                                                19

<210> SEQ ID NO 515
<211> LENGTH: 19
<212> TYPE: DNA
<213> ORGANISM: Homo sapiens

<400> SEQUENCE: 515
tgccattgtg gtccttatc                                                19

<210> SEQ ID NO 516
<211> LENGTH: 19
<212> TYPE: DNA
<213> ORGANISM: Homo sapiens

<400> SEQUENCE: 516
cattgtggtc cttatcatc                                                19
```

```
<210> SEQ ID NO 517
<211> LENGTH: 19
<212> TYPE: DNA
<213> ORGANISM: Homo sapiens

<400> SEQUENCE: 517
gtggtcctta tcatcttcc                                                19

<210> SEQ ID NO 518
<211> LENGTH: 19
<212> TYPE: DNA
<213> ORGANISM: Homo sapiens

<400> SEQUENCE: 518
ggtccttatc atcttccac                                                19

<210> SEQ ID NO 519
<211> LENGTH: 19
<212> TYPE: DNA
<213> ORGANISM: Homo sapiens

<400> SEQUENCE: 519
ccttatcatc ttccacaac                                                19

<210> SEQ ID NO 520
<211> LENGTH: 19
<212> TYPE: DNA
<213> ORGANISM: Homo sapiens

<400> SEQUENCE: 520
cttatcatct tccacaacc                                                19

<210> SEQ ID NO 521
<211> LENGTH: 19
<212> TYPE: DNA
<213> ORGANISM: Homo sapiens

<400> SEQUENCE: 521
ttatcatctt ccacaaccc                                                19

<210> SEQ ID NO 522
<211> LENGTH: 19
<212> TYPE: DNA
<213> ORGANISM: Homo sapiens

<400> SEQUENCE: 522
catgttcctg ctaataggc                                                19

<210> SEQ ID NO 523
<211> LENGTH: 19
<212> TYPE: DNA
<213> ORGANISM: Homo sapiens

<400> SEQUENCE: 523
gttcctgcta ataggcagc                                                19

<210> SEQ ID NO 524
<211> LENGTH: 19
<212> TYPE: DNA
<213> ORGANISM: Homo sapiens

<400> SEQUENCE: 524
```

```
ttcctgctaa taggcagcc                                                19

<210> SEQ ID NO 525
<211> LENGTH: 19
<212> TYPE: DNA
<213> ORGANISM: Homo sapiens

<400> SEQUENCE: 525
ctaataggca gcctggctc                                                19

<210> SEQ ID NO 526
<211> LENGTH: 19
<212> TYPE: DNA
<213> ORGANISM: Homo sapiens

<400> SEQUENCE: 526
taggcagcct ggctcttgc                                                19

<210> SEQ ID NO 527
<211> LENGTH: 19
<212> TYPE: DNA
<213> ORGANISM: Homo sapiens

<400> SEQUENCE: 527
acctgcttca gtcagaagc                                                19

<210> SEQ ID NO 528
<211> LENGTH: 19
<212> TYPE: DNA
<213> ORGANISM: Homo sapiens

<400> SEQUENCE: 528
cctgcttcag tcagaagcc                                                19

<210> SEQ ID NO 529
<211> LENGTH: 19
<212> TYPE: DNA
<213> ORGANISM: Homo sapiens

<400> SEQUENCE: 529
tgcttcagtc agaagccac                                                19

<210> SEQ ID NO 530
<211> LENGTH: 19
<212> TYPE: DNA
<213> ORGANISM: Homo sapiens

<400> SEQUENCE: 530
gcttcagtca gaagccacc                                                19

<210> SEQ ID NO 531
<211> LENGTH: 19
<212> TYPE: DNA
<213> ORGANISM: Homo sapiens

<400> SEQUENCE: 531
cagtcagaag ccaccaagc                                                19

<210> SEQ ID NO 532
<211> LENGTH: 19
<212> TYPE: DNA
<213> ORGANISM: Homo sapiens

<400> SEQUENCE: 532
```
agaagccacc aagctggtc                                                19

<210> SEQ ID NO 533
<211> LENGTH: 19
<212> TYPE: DNA
<213> ORGANISM: Homo sapiens

<400> SEQUENCE: 533
aagccaccaa gctggtcac                                                19

<210> SEQ ID NO 534
<211> LENGTH: 19
<212> TYPE: DNA
<213> ORGANISM: Homo sapiens

<400> SEQUENCE: 534
cacgatcggc ctcattgtc                                                19

<210> SEQ ID NO 535
<211> LENGTH: 19
<212> TYPE: DNA
<213> ORGANISM: Homo sapiens

<400> SEQUENCE: 535
cctcattgtc gcctctttc                                                19

<210> SEQ ID NO 536
<211> LENGTH: 19
<212> TYPE: DNA
<213> ORGANISM: Homo sapiens

<400> SEQUENCE: 536
tcattgtcgc ctctttctc                                                19

<210> SEQ ID NO 537
<211> LENGTH: 19
<212> TYPE: DNA
<213> ORGANISM: Homo sapiens

<400> SEQUENCE: 537
ttgtcgcctc tttctctgc                                                19

<210> SEQ ID NO 538
<211> LENGTH: 19
<212> TYPE: DNA
<213> ORGANISM: Homo sapiens

<400> SEQUENCE: 538
tgtcgcctct ttctctgcc                                                19

<210> SEQ ID NO 539
<211> LENGTH: 19
<212> TYPE: DNA
<213> ORGANISM: Homo sapiens

<400> SEQUENCE: 539
tcgcctcttt ctctgcctc                                                19

<210> SEQ ID NO 540
<211> LENGTH: 19
<212> TYPE: DNA
<213> ORGANISM: Homo sapiens -continued

<400> SEQUENCE: 540
ctctttctct gcctctgtc                                          19

<210> SEQ ID NO 541
<211> LENGTH: 19
<212> TYPE: DNA
<213> ORGANISM: Homo sapiens

<400> SEQUENCE: 541
tttctctgcc tctgtctgc                                          19

<210> SEQ ID NO 542
<211> LENGTH: 19
<212> TYPE: DNA
<213> ORGANISM: Homo sapiens

<400> SEQUENCE: 542
ctctgcctct gtctgcagc                                          19

<210> SEQ ID NO 543
<211> LENGTH: 19
<212> TYPE: DNA
<213> ORGANISM: Homo sapiens

<400> SEQUENCE: 543
ctgcagcttg ctggctatc                                          19

<210> SEQ ID NO 544
<211> LENGTH: 19
<212> TYPE: DNA
<213> ORGANISM: Homo sapiens

<400> SEQUENCE: 544
gcagcttgct ggctatcac                                          19

<210> SEQ ID NO 545
<211> LENGTH: 19
<212> TYPE: DNA
<213> ORGANISM: Homo sapiens

<400> SEQUENCE: 545
gctggctatc actgttgac                                          19

<210> SEQ ID NO 546
<211> LENGTH: 19
<212> TYPE: DNA
<213> ORGANISM: Homo sapiens

<400> SEQUENCE: 546
ctggctatca ctgttgacc                                          19

<210> SEQ ID NO 547
<211> LENGTH: 19
<212> TYPE: DNA
<213> ORGANISM: Homo sapiens

<400> SEQUENCE: 547
ggctatcact gttgaccgc                                          19

<210> SEQ ID NO 548
<211> LENGTH: 19
<212> TYPE: DNA
<213> ORGANISM: Homo sapiens -continued

<400> SEQUENCE: 548
tatcactgtt gaccgctac                     19

<210> SEQ ID NO 549
<211> LENGTH: 19
<212> TYPE: DNA
<213> ORGANISM: Homo sapiens

<400> SEQUENCE: 549
atcactgttg accgctacc                     19

<210> SEQ ID NO 550
<211> LENGTH: 19
<212> TYPE: DNA
<213> ORGANISM: Homo sapiens

<400> SEQUENCE: 550
cactgttgac cgctacctc                     19

<210> SEQ ID NO 551
<211> LENGTH: 19
<212> TYPE: DNA
<213> ORGANISM: Homo sapiens

<400> SEQUENCE: 551
ctgttgaccg ctacctctc                     19

<210> SEQ ID NO 552
<211> LENGTH: 19
<212> TYPE: DNA
<213> ORGANISM: Homo sapiens

<400> SEQUENCE: 552
gttgaccgct acctctcac                     19

<210> SEQ ID NO 553
<211> LENGTH: 19
<212> TYPE: DNA
<213> ORGANISM: Homo sapiens

<400> SEQUENCE: 553
ccgctacctc tcactgtac                     19

<210> SEQ ID NO 554
<211> LENGTH: 19
<212> TYPE: DNA
<213> ORGANISM: Homo sapiens

<400> SEQUENCE: 554
ctacctctca ctgtactac                     19

<210> SEQ ID NO 555
<211> LENGTH: 19
<212> TYPE: DNA
<213> ORGANISM: Homo sapiens

<400> SEQUENCE: 555
acctctcact gtactacgc                     19

<210> SEQ ID NO 556
<211> LENGTH: 19
<212> TYPE: DNA

<213> ORGANISM: Homo sapiens

<400> SEQUENCE: 556
ctctcactgt actacgctc					19

<210> SEQ ID NO 557
<211> LENGTH: 19
<212> TYPE: DNA
<213> ORGANISM: Homo sapiens

<400> SEQUENCE: 557
cactgtacta cgctctgac					19

<210> SEQ ID NO 558
<211> LENGTH: 19
<212> TYPE: DNA
<213> ORGANISM: Homo sapiens

<400> SEQUENCE: 558
gtactacgct ctgacgtac					19

<210> SEQ ID NO 559
<211> LENGTH: 19
<212> TYPE: DNA
<213> ORGANISM: Homo sapiens

<400> SEQUENCE: 559
tactacgctc tgacgtacc					19

<210> SEQ ID NO 560
<211> LENGTH: 19
<212> TYPE: DNA
<213> ORGANISM: Homo sapiens

<400> SEQUENCE: 560
acgctctgac gtaccattc					19

<210> SEQ ID NO 561
<211> LENGTH: 19
<212> TYPE: DNA
<213> ORGANISM: Homo sapiens

<400> SEQUENCE: 561
cgtaccattc ggagaggac					19

<210> SEQ ID NO 562
<211> LENGTH: 19
<212> TYPE: DNA
<213> ORGANISM: Homo sapiens

<400> SEQUENCE: 562
ccattcggag aggacggtc					19

<210> SEQ ID NO 563
<211> LENGTH: 19
<212> TYPE: DNA
<213> ORGANISM: Homo sapiens

<400> SEQUENCE: 563
agaggacggt cacgtttac					19

<210> SEQ ID NO 564
<211> LENGTH: 19

```
<212> TYPE: DNA
<213> ORGANISM: Homo sapiens

<400> SEQUENCE: 564
gaggacggtc acgtttacc                                                19

<210> SEQ ID NO 565
<211> LENGTH: 19
<212> TYPE: DNA
<213> ORGANISM: Homo sapiens

<400> SEQUENCE: 565
ggtcacgttt acctatgtc                                                19

<210> SEQ ID NO 566
<211> LENGTH: 19
<212> TYPE: DNA
<213> ORGANISM: Homo sapiens

<400> SEQUENCE: 566
acgtttacct atgtcatgc                                                19

<210> SEQ ID NO 567
<211> LENGTH: 19
<212> TYPE: DNA
<213> ORGANISM: Homo sapiens

<400> SEQUENCE: 567
gtttacctat gtcatgctc                                                19

<210> SEQ ID NO 568
<211> LENGTH: 19
<212> TYPE: DNA
<213> ORGANISM: Homo sapiens

<400> SEQUENCE: 568
tacctatgtc atgctcgtc                                                19

<210> SEQ ID NO 569
<211> LENGTH: 19
<212> TYPE: DNA
<213> ORGANISM: Homo sapiens

<400> SEQUENCE: 569
tatgtcatgc tcgtcatgc                                                19

<210> SEQ ID NO 570
<211> LENGTH: 19
<212> TYPE: DNA
<213> ORGANISM: Homo sapiens

<400> SEQUENCE: 570
tgtcatgctc gtcatgctc                                                19

<210> SEQ ID NO 571
<211> LENGTH: 19
<212> TYPE: DNA
<213> ORGANISM: Homo sapiens

<400> SEQUENCE: 571
cagaccgctc accaagaac                                                19

<210> SEQ ID NO 572
```

```
<211> LENGTH: 19
<212> TYPE: DNA
<213> ORGANISM: Homo sapiens

<400> SEQUENCE: 572
accgctcacc aagaacaac                                              19

<210> SEQ ID NO 573
<211> LENGTH: 19
<212> TYPE: DNA
<213> ORGANISM: Homo sapiens

<400> SEQUENCE: 573
cgctcaccaa gaacaacgc                                              19

<210> SEQ ID NO 574
<211> LENGTH: 19
<212> TYPE: DNA
<213> ORGANISM: Homo sapiens

<400> SEQUENCE: 574
caagaacaac gcggccatc                                              19

<210> SEQ ID NO 575
<211> LENGTH: 19
<212> TYPE: DNA
<213> ORGANISM: Homo sapiens

<400> SEQUENCE: 575
gaacaacgcg gccatcctc                                              19

<210> SEQ ID NO 576
<211> LENGTH: 19
<212> TYPE: DNA
<213> ORGANISM: Homo sapiens

<400> SEQUENCE: 576
cctctcggtg tccttcctc                                              19

<210> SEQ ID NO 577
<211> LENGTH: 19
<212> TYPE: DNA
<213> ORGANISM: Homo sapiens

<400> SEQUENCE: 577
ctcggtgtcc ttcctcttc                                              19

<210> SEQ ID NO 578
<211> LENGTH: 19
<212> TYPE: DNA
<213> ORGANISM: Homo sapiens

<400> SEQUENCE: 578
ccttcctctt catgtttgc                                              19

<210> SEQ ID NO 579
<211> LENGTH: 19
<212> TYPE: DNA
<213> ORGANISM: Homo sapiens

<400> SEQUENCE: 579
ttcctcttca tgtttgcgc                                              19
```

```
<210> SEQ ID NO 580
<211> LENGTH: 19
<212> TYPE: DNA
<213> ORGANISM: Homo sapiens

<400> SEQUENCE: 580
cctcttcatg tttgcgctc                                                19

<210> SEQ ID NO 581
<211> LENGTH: 19
<212> TYPE: DNA
<213> ORGANISM: Homo sapiens

<400> SEQUENCE: 581
ttcatgtttg cgctcatgc                                                19

<210> SEQ ID NO 582
<211> LENGTH: 19
<212> TYPE: DNA
<213> ORGANISM: Homo sapiens

<400> SEQUENCE: 582
atgtttgcgc tcatgcttc                                                19

<210> SEQ ID NO 583
<211> LENGTH: 19
<212> TYPE: DNA
<213> ORGANISM: Homo sapiens

<400> SEQUENCE: 583
tttgcgctca tgcttcagc                                                19

<210> SEQ ID NO 584
<211> LENGTH: 19
<212> TYPE: DNA
<213> ORGANISM: Homo sapiens

<400> SEQUENCE: 584
tgcgctcatg cttcagctc                                                19

<210> SEQ ID NO 585
<211> LENGTH: 19
<212> TYPE: DNA
<213> ORGANISM: Homo sapiens

<400> SEQUENCE: 585
gctcatgctt cagctctac                                                19

<210> SEQ ID NO 586
<211> LENGTH: 19
<212> TYPE: DNA
<213> ORGANISM: Homo sapiens

<400> SEQUENCE: 586
catgcttcag ctctacatc                                                19

<210> SEQ ID NO 587
<211> LENGTH: 19
<212> TYPE: DNA
<213> ORGANISM: Homo sapiens

<400> SEQUENCE: 587
atgcttcagc tctacatcc                                                19
```

```
<210> SEQ ID NO 588
<211> LENGTH: 19
<212> TYPE: DNA
<213> ORGANISM: Homo sapiens

<400> SEQUENCE: 588
tcagctctac atccagatc                                        19

<210> SEQ ID NO 589
<211> LENGTH: 19
<212> TYPE: DNA
<213> ORGANISM: Homo sapiens

<400> SEQUENCE: 589
tgtaagattg tgatgaggc                                        19

<210> SEQ ID NO 590
<211> LENGTH: 19
<212> TYPE: DNA
<213> ORGANISM: Homo sapiens

<400> SEQUENCE: 590
taagattgtg atgaggcac                                        19

<210> SEQ ID NO 591
<211> LENGTH: 19
<212> TYPE: DNA
<213> ORGANISM: Homo sapiens

<400> SEQUENCE: 591
agattgtgat gaggcacgc                                        19

<210> SEQ ID NO 592
<211> LENGTH: 19
<212> TYPE: DNA
<213> ORGANISM: Homo sapiens

<400> SEQUENCE: 592
gattgtgatg aggcacgcc                                        19

<210> SEQ ID NO 593
<211> LENGTH: 19
<212> TYPE: DNA
<213> ORGANISM: Homo sapiens

<400> SEQUENCE: 593
attgtgatga ggcacgccc                                        19

<210> SEQ ID NO 594
<211> LENGTH: 19
<212> TYPE: DNA
<213> ORGANISM: Homo sapiens

<400> SEQUENCE: 594
gtgatgaggc acgcccatc                                        19

<210> SEQ ID NO 595
<211> LENGTH: 19
<212> TYPE: DNA
<213> ORGANISM: Homo sapiens

<400> SEQUENCE: 595
tcagatagcc ctgcagcac                                        19
```

<210> SEQ ID NO 596
<211> LENGTH: 19
<212> TYPE: DNA
<213> ORGANISM: Homo sapiens

<400> SEQUENCE: 596
cagatagccc tgcagcacc                                               19

<210> SEQ ID NO 597
<211> LENGTH: 19
<212> TYPE: DNA
<213> ORGANISM: Homo sapiens

<400> SEQUENCE: 597
agccctgcag caccacttc                                               19

<210> SEQ ID NO 598
<211> LENGTH: 19
<212> TYPE: DNA
<213> ORGANISM: Homo sapiens

<400> SEQUENCE: 598
cgtcgcacta tgtgaccac                                               19

<210> SEQ ID NO 599
<211> LENGTH: 19
<212> TYPE: DNA
<213> ORGANISM: Homo sapiens

<400> SEQUENCE: 599
gtcgcactat gtgaccacc                                               19

<210> SEQ ID NO 600
<211> LENGTH: 19
<212> TYPE: DNA
<213> ORGANISM: Homo sapiens

<400> SEQUENCE: 600
ctccaccctg gctatcatc                                               19

<210> SEQ ID NO 601
<211> LENGTH: 19
<212> TYPE: DNA
<213> ORGANISM: Homo sapiens

<400> SEQUENCE: 601
tccaccctgg ctatcatcc                                               19

<210> SEQ ID NO 602
<211> LENGTH: 19
<212> TYPE: DNA
<213> ORGANISM: Homo sapiens

<400> SEQUENCE: 602
tttgctgctt gctggatgc                                               19

<210> SEQ ID NO 603
<211> LENGTH: 19
<212> TYPE: DNA
<213> ORGANISM: Homo sapiens

<400> SEQUENCE: 603

| | |
|---|---|
| ttgctgcttg ctggatgcc | 19 |

<210> SEQ ID NO 604
<211> LENGTH: 19
<212> TYPE: DNA
<213> ORGANISM: Homo sapiens

<400> SEQUENCE: 604

| | |
|---|---|
| tgcttgctgg atgcctttc | 19 |

<210> SEQ ID NO 605
<211> LENGTH: 19
<212> TYPE: DNA
<213> ORGANISM: Homo sapiens

<400> SEQUENCE: 605

| | |
|---|---|
| ttgctggatg cctttcacc | 19 |

<210> SEQ ID NO 606
<211> LENGTH: 19
<212> TYPE: DNA
<213> ORGANISM: Homo sapiens

<400> SEQUENCE: 606

| | |
|---|---|
| cttgatagcg gattacacc | 19 |

<210> SEQ ID NO 607
<211> LENGTH: 19
<212> TYPE: DNA
<213> ORGANISM: Homo sapiens

<400> SEQUENCE: 607

| | |
|---|---|
| ctccatctat acctacgcc | 19 |

<210> SEQ ID NO 608
<211> LENGTH: 19
<212> TYPE: DNA
<213> ORGANISM: Homo sapiens

<400> SEQUENCE: 608

| | |
|---|---|
| catctatacc tacgccacc | 19 |

<210> SEQ ID NO 609
<211> LENGTH: 19
<212> TYPE: DNA
<213> ORGANISM: Homo sapiens

<400> SEQUENCE: 609

| | |
|---|---|
| atctatacct acgccaccc | 19 |

<210> SEQ ID NO 610
<211> LENGTH: 19
<212> TYPE: DNA
<213> ORGANISM: Homo sapiens

<400> SEQUENCE: 610

| | |
|---|---|
| tatacctacg ccaccctcc | 19 |

<210> SEQ ID NO 611
<211> LENGTH: 19
<212> TYPE: DNA
<213> ORGANISM: Homo sapiens

<400> SEQUENCE: 611
cgccacctac aattccatc                                          19

<210> SEQ ID NO 612
<211> LENGTH: 19
<212> TYPE: DNA
<213> ORGANISM: Homo sapiens

<400> SEQUENCE: 612
cacctacaat tccatcatc                                          19

<210> SEQ ID NO 613
<211> LENGTH: 19
<212> TYPE: DNA
<213> ORGANISM: Homo sapiens

<400> SEQUENCE: 613
tacaattcca tcatcaacc                                          19

<210> SEQ ID NO 614
<211> LENGTH: 19
<212> TYPE: DNA
<213> ORGANISM: Homo sapiens

<400> SEQUENCE: 614
ttccatcatc aaccctgtc                                          19

<210> SEQ ID NO 615
<211> LENGTH: 19
<212> TYPE: DNA
<213> ORGANISM: Homo sapiens

<400> SEQUENCE: 615
tttcagaaac caagagatc                                          19

<210> SEQ ID NO 616
<211> LENGTH: 19
<212> TYPE: DNA
<213> ORGANISM: Homo sapiens

<400> SEQUENCE: 616
accaagagat ccagaaagc                                          19

<210> SEQ ID NO 617
<211> LENGTH: 19
<212> TYPE: DNA
<213> ORGANISM: Homo sapiens

<400> SEQUENCE: 617
caagagatcc agaaagcgc                                          19

<210> SEQ ID NO 618
<211> LENGTH: 19
<212> TYPE: DNA
<213> ORGANISM: Homo sapiens

<400> SEQUENCE: 618
agcgctctgt ctcatttgc                                          19

<210> SEQ ID NO 619
<211> LENGTH: 19
<212> TYPE: DNA
<213> ORGANISM: Homo sapiens

```
<400> SEQUENCE: 619
gctctgtctc atttgctgc                                              19

<210> SEQ ID NO 620
<211> LENGTH: 19
<212> TYPE: DNA
<213> ORGANISM: Homo sapiens

<400> SEQUENCE: 620
atttgctgcg gctgcatcc                                              19
```